US009447444B2

(12) United States Patent
Winzer et al.

(10) Patent No.: US 9,447,444 B2
(45) Date of Patent: Sep. 20, 2016

(54) BIOSYNTHESIS OF OPIATE ALKALOIDS

(71) Applicant: Sun Pharmaceutical Industries (Australia) Pty Ltd, Notting HIll (AU)

(72) Inventors: Thilo Winzer, York (GB); Ian Alexander Graham, York (GB); Tracy Carol Walker, Latrobe (AU)

(73) Assignee: Sun Pharmaceutical Industries (Australia) Pty Ltd, Notting Hill (AU)

( * ) Notice: Subject to any disclaimer, the term of this patent is extended or adjusted under 35 U.S.C. 154(b) by 0 days.

(21) Appl. No.: 14/375,120

(22) PCT Filed: Mar. 12, 2013

(86) PCT No.: PCT/GB2013/050599
§ 371 (c)(1),
(2) Date: Jul. 28, 2014

(87) PCT Pub. No.: WO2013/136057
PCT Pub. Date: Sep. 19, 2013

(65) Prior Publication Data

US 2015/0004659 A1 Jan. 1, 2015

(30) Foreign Application Priority Data

Mar. 13, 2012 (GB) .................................. 1204407.9

(51) Int. Cl.

| | |
|---|---|
| ***C12P 17/18*** | (2006.01) |
| ***C12N 9/04*** | (2006.01) |
| ***C12N 9/10*** | (2006.01) |
| ***C12N 9/18*** | (2006.01) |
| ***C12N 5/04*** | (2006.01) |
| ***C12N 5/00*** | (2006.01) |
| ***C12P 19/34*** | (2006.01) |
| ***C12N 15/82*** | (2006.01) |
| ***A01H 5/00*** | (2006.01) |
| ***C07H 21/04*** | (2006.01) |
| ***C07K 14/415*** | (2006.01) |
| ***C12N 15/52*** | (2006.01) |

(52) U.S. Cl.
CPC ............ *C12P 17/188* (2013.01); *C07K 14/415* (2013.01); *C12N 15/52* (2013.01); *C12N 15/8243* (2013.01)

(58) Field of Classification Search
CPC . C12N 15/52; C12N 15/8243; C12P 17/188; C07K 14/415
USPC ...... 435/119, 190, 193, 197, 419, 410, 91.1; 800/278, 298; 536/23.1, 23.2
See application file for complete search history.

(56) References Cited

U.S. PATENT DOCUMENTS

| | | | | |
|---|---|---|---|---|
| 7,390,642 | B2 * | 6/2008 | Kutchan .............. | C12N 9/1029 435/193 |
| 2005/0106588 | A1 | 5/2005 | Kutchan et al. | |
| 2007/0199090 | A1 | 8/2007 | Apuya et al. | |
| 2008/0196123 | A1 | 8/2008 | Kutchan et al. | |
| 2009/0227796 | A1 | 9/2009 | Fist | |
| 2010/0075385 | A1 | 3/2010 | Kutchan et al. | |
| 2010/0184166 | A1 | 7/2010 | Sato et al. | |
| 2013/0104258 | A1 * | 4/2013 | Winzer ................ | C07K 14/415 800/278 |
| 2013/0133105 | A1 | 5/2013 | Winzer et al. | |

FOREIGN PATENT DOCUMENTS

| | | | |
|---|---|---|---|
| EP | 1 270 727 | A1 | 1/2003 |
| EP | 1 512 748 | A1 | 3/2005 |
| EP | 1 632 565 | A1 | 3/2006 |
| EP | 1 837 396 | A1 | 9/2007 |
| WO | WO 99/14351 | A1 | 3/1999 |
| WO | WO 02/101052 | A2 | 12/2002 |
| WO | WO 2006/081029 | A2 | 8/2006 |
| WO | WO 2006/138012 | A1 | 12/2006 |
| WO | WO 2008/069878 | A2 | 6/2008 |
| WO | WO 2009/005647 | A2 | 1/2009 |
| WO | WO 2009/064771 | A2 | 5/2009 |
| WO | WO 2011/161431 | A2 | 12/2011 |
| WO | WO 2012/010872 | A2 | 1/2012 |

OTHER PUBLICATIONS

Omura and Sato, "The Carbon Monoxide-Binding Pigment of Liver Microsomes. I. Evidence for Its Hemoprotein Nature," *J. Biol. Chem*. 239:2370-2378, 1964.
Accession No. AB126256, May 10, 2005.
Accession No. AB126257, May 10, 2005.
Accession No. AB374409, Jan. 10, 2008.
Accession No. A9ZT62, Feb. 26, 2008.
Accession No. GU325750, Jan. 28, 2010.
Accession No. D3JXF8, Mar. 23, 2010.
Chavez et al., "Characterization of Two Methylenedioxy Bridge-Forming Cytochrome P450-Dependent Enzymes of Alkaloid Formation in the Mexican Prickly Poppy Argemone mexica," *Arch. Biochem. Biophys*. 507:186-193, 2011.
Decker et al., "Characterization of Proteins in Latex of the Opium Poppy (Papaver somniferum) Using Two-Dimensional Gel Electrophoresis and Microsequencing," *Electrophoresis 21*:3500-3516, 2000.

(Continued)

*Primary Examiner* — Ganapathirama Raghu
(74) *Attorney, Agent, or Firm* — Klarquist Sparkman, LLP

(57) ABSTRACT

The disclosure relates to a nucleic acid molecule isolated from a *Papaver somniferum* cultivar that produces the opiate alkaloid noscapine which comprises 10 genes involved in the biosynthesis of opiate alkaloids.

6 Claims, 27 Drawing Sheets

(56) References Cited

OTHER PUBLICATIONS

Figure 1A:
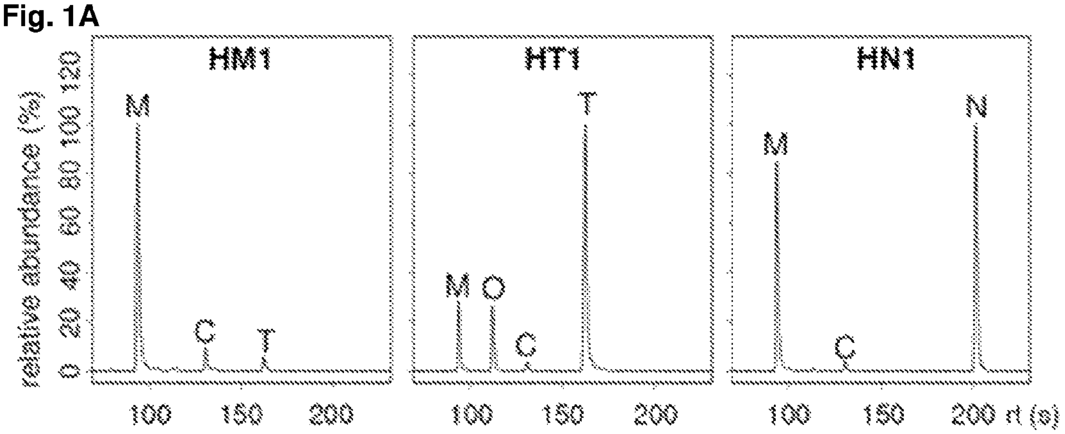

Facchini et al., "Developmental and Inducible Accumulation of Gene Transcripts Involved in Alkaloid Biosynthesis in Opium Poppy," *Phytochemistry 64*:177-186, 2003.
Facchini and De Luca, "Opium Poppy and Madagascar Periwinkle: Model Non-Model Systems to Investigate Alkaloid Biosynthesis in Plants," *Plant J. 54*:763-784, 2008.
Gesell et al., "CYP719B1 is Salutaridine Synthase, the C—C Phenol-Coupling Enzyme of Morphine Biosynthesis in Opium Poppy," *J. Biol. Chem.* 284:24432-24442, 2009.
Great Britain Search Report dated Oct. 15, 2010 for Great Britain Application No. GB1010471.9.
Great Britain Search Report dated Nov. 23, 2010 for Great Britain Application No. GB1012262.0.
Ikezawa et al., "Molecular Cloning and Characterization of Methylenedioxy Bridge-Forming Enzymes Involved in Stylopine Biosynthesis in Eschscholzia californica," *FEBS J. 274*:1019-1035, 2007.
Liscombe and Facchini, "Molecular Cloning and Characterization of Tetrahydroprotoberberine *cis*-N-Methyltransferase, an Enzyme Involved in Alkaloid Biosynthesis in Opium Poppy," *J. Biol. Chem. 282*:14741-14751, 2007.
Morishige et al., "Molecular Characterization of the *S*-adenosyl-L-methionine:3'-Hydroxy-*N*-methylcoclaurine 4'-*O*-Methyltransferase Involved in Isoquinoline Alkaloid Biosynthesis in Coptis japonica," *J. Biol. Chem. 275*:23398-23405, 2000.
Ounaroon et al., "(*R,S*)-Reticuline 7-*O*-methyltransferase and (*R,S*)-norcoclaurine 6-*O*-methyltransferase of Papaver somniferum—cDNA Cloning and Characterization of Methyl Transfer Enzymes of Alkaloid Biosynthesis in Opium Poppy," *Plant J. 36*:808-819, 2003.
Wesley et al., "Construct Design for Efficient, Effective and High-Throughput Gene Silencing in Plants," *Plant J. 27*:581-590, 2001.
Ziegler et al., "Comparative Macroarray Analysis of Morphine Containing Papaver somniferum and Eight Morphine Free Papaver Species Identifies an *O*-methyltransferase Involved in Benzylisoquinoline Biosynthesis," *Planta 222*:458-471, 2005.
Facchini et al., "Opium Poppy: Blueprint for an Alkaloid Factory," *Phytochem Rev. 6*:97-124, 2007.
NCBI accession No. XP_002284806 dated Mar. 20, 2009.
NCBI accession No. XP_002284810.2 dated Mar. 20, 2009.
NCBI accession No. XP_002284031.1 dated Mar. 20, 2009.
New Zealand Intellectual Property Office, Further Examination Report for NZ Application 604057, dated Oct. 17, 2014 (2 pages).
Sato et al., "S-Adenosyl-L-Methionine: Scoulerine-9-O-Methyltransferase from Cultured Coptis Japonica Cells" *Phytochem. 32*:659-664, 1993.
Allen et al., "Metabolic Engineering of Morphinan Alkaloids by Over-Expression and RNAi Suppression of Salutaridinol 7-*O*-acetyltransferase in Opium Poppy," *Plant Biotech J. 6*:22-30, 2008.
Evertsz et al., "Research Report Hybridization Cross-Reactivity within Homolo-gous Gene Families on Glass cDNA Microarrays," *Biotechniques 31*:1182-1192, 2001.
Gümüşçü et al., "Evaluation of Selected Poppy (Papaver somniferum L.) Lines by Their Morphine and Other Alkaloids Contents," *Eur Food Res Technol. 226*:1213-1220, 2008.
Pienkny et al., "Functional Characterization of a Novel Benzylisoquinoline *O*-Methyltransferase Suggests Its Involvement in Papaverine Biosynthesis in Opium Poppy (Papaver somniferum L)," *Plant J. 60*:56-67, 2009.
Schuler and Werck-Reichhart, "Functional Genomics of P450s," *Annu Rev Plant Biol. 54*:629-667, 2003.
Till et al., "Mismatch Cleavage by Single- Strand Specific Nucleases," *Nucleic Acids Res. 32*:2632-2641, 2004.
GenBank Accession No. CAG34222.1, Jun. 14, 2004.
Database UniProt [Online] Accession No. QOZPV6, Aug. 22, 2006.
Database UniProt [Online] Accession No. B9SK36, Mar. 24, 2009.
Chan et al., "Draft Genome Sequence of the Oilseed Species Ricinus communis," *Nat Biotechnol. 28*:951-959, 2010.
Chu et al., "From Hormones to Secondary Metabolism: The Emergence of Metabolic Gene Clusters in Plants," *Plant J. 66*:66-79, 2011.
Desgagné-Penix et al., "Integration of Deep Transcriptome and Proteome Analyses Reveals the Components of Alkaloid Metabolism in Opium Poppy Cell Cultures," *BMC Plant Biol. 10*:252, 2010.
Field et al., "Formation of Plant Metabolic Gene Clusters Within Dynamic Chromosomal Regions," *Proc Natl Acad Sci. 108*:16116-16121, 2011.
Frick et al., "Metabolic Engineering with a Morphine Biosynthetic P450 in Opium Poppy Surpasses Breeding," *Metabolic Eng. 9*:169-176, 2007.
Great Britain Search Report dated Jul. 2, 2012 for Great Britain Application No. GB1204407.9 (PSMT1).
Great Britain Search Report dated Oct. 1, 2012 for Great Britain Application No. GB1204407.9 (CYP82Y1).
Great Britain Search Report dated Oct. 1, 2012 for Great Britain Application No. GB1204407.9 (PSSDR1).
Great Britain Search Report dated Oct. 31, 2012 for Great Britain Application No. GB1204407.9 (PSATI).
Great Britain Search Report dated Oct. 31, 2012 for Great Britain Application No. GB1204407.9 (PSCXE1).
Hagel et al., "Quantitative $^1$H Nuclear Magnetic Resonance Metabolite Profiling as a Functional Genomics Platform to Investigate Alkaloid Biosynthesis in Opium Poppy," *Plant Physiol. 147*:1805-1821, 2008.
Hileman et al., "Virus-Induced Gene Silencing is an Effective Tool for Assaying Gene Function in the Basal Eudicot Species Papaver somniferum (Opium Poppy)," *Plant J. 44*:334-341, 2005.
Kleber da Rocha et al., "Effect of Different Culture Medium Components on Production of Alkaloid in Callus Tissues of Cereus Peruvianus (Cactaceae)," *Acta Scientiarum Biol. Sci. 27*:37-41, 2005.
Okada, "The Biosynthesis of Isoprenoids and the Mechanisms Regulating it in Plants," *Biosci Biotechol Biochem. 75*:1219-1225, 2011.
Takos et al., "Genomic Clustering of Cyanogenic Glucoside Biosynthetic Genes Aids Their Identification in Lotus japonicus and Suggests the Repeated Evolution of this Chemical Defence Pathway," *Plant J. 68*:273-286, 2011.
Wijekoon and Facchini, "Systematic Knockdown of Morphine Pathway Enzymes in Opium Poppy Using Virus-Induced Gene Silencing," *Plant J. 69*:1052-1063, 2012.
Winzer et al., "A Papaver somniferum 10-Gene Cluster for Synthesis of the Anticancer Alkaloid Noscapine," *Science 336*:1704-1708, 2012.
Ziegler et al., "Comparative Transcrpt and Alkaloid Profiling in Papaver Species Identifies a Short Chain Dehydrogenase/Reductase Involved in Morphine Biosynthesis," *Plant J. 48*:177-192, 2006.
Ziegler et al., "Evolution of Morphine Biosynthesis in Opium Poppy," *Phytochem. 70*:1696-1707, 2009.
International Search Report and Written Opinion of the International Searching Authority for corresponding PCT Application No. PCT/GB2011/051340, dated Feb. 8, 2012.
Sequence alignment showing alignment of *PSCYP3* (SEQ ID No. of U.S. Appl. No. 13/806,608) with NCBI accession No. XP_002284806, NCBI accession No. XP_002284810.2, and NCBI accession No. XP_002284031.1, retrieved from the internet Jan. 27, 2015. Provided by New Zealand Intellectual Property Office on Oct. 17, 2014.
Nucleic acid sequence alignment between GenBank Accession No. AK320249.1 and methyltransferase PSMT2 sequence of SEQ ID No. 2 in U.S. Appl. No. 13/806,310, Provided by New Zealand Intellectual Property Office on Sep. 15, 2014.
Nucleic acid sequence alignment between GenBank Accession No. BT096188.1 and methyltransferase PSMT2 sequence of SEQ ID No. 2 in U.S. Appl. No. 13/806,310, Provided by New Zealand Intellectual Property Office on Sep. 15, 2014.
Nucleic acid sequence alignment between GenBank Accession No. EU882980.1 and methyltransferase PSMT2 sequence of SEQ ID No. 2 in U.S. Appl. No. 13/806,310, Provided by New Zealand Intellectual Property Office on Sep. 15, 2014.

(56) References Cited

OTHER PUBLICATIONS

Amino acid sequence alignment between GenBank Accession No. AK320249.1 and methyltransferase PSMT2 sequence of SEQ ID No. 8 in U.S. Appl. No. 13/806,310 (obtained Oct. 10, 2014).

Amino acid sequence alignment between GenBank Accession No. BT096188.1 and methyltransferase PSMT2 sequence of SEQ ID No. 8 in U.S. Appl. No. 13/806,310 (obtained Oct. 10, 2014).

Amino acid sequence alignment between GenBank Accession No. EU882980.1 and methyltransferase PSMT2 sequence of SEQ ID No. 8 in U.S. Appl. No. 13/806,310 (obtained Oct. 10, 2014).

* cited by examiner

Fig. 4A PSMT1
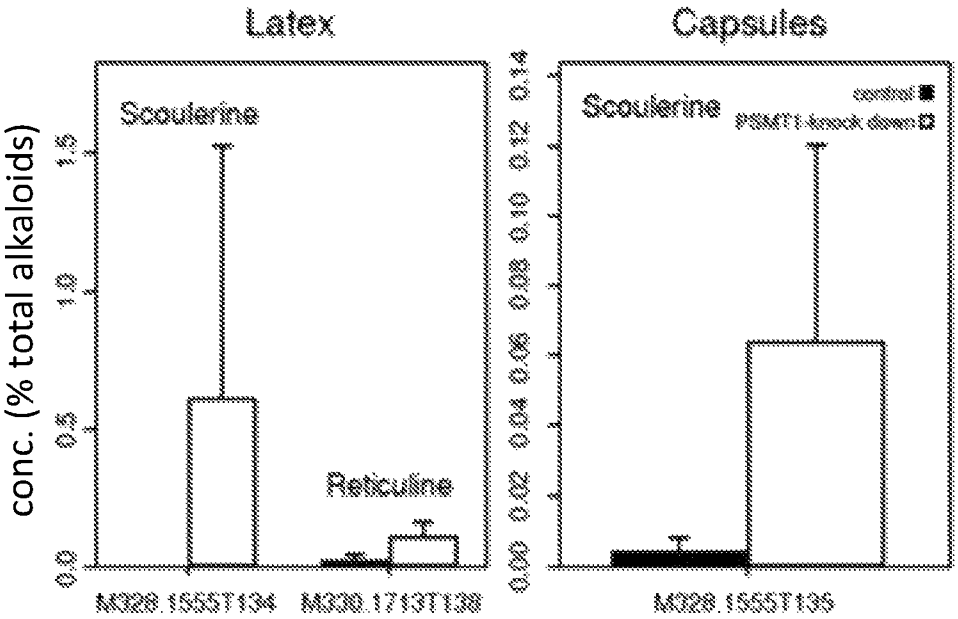
Fig. 4B CYP719A21
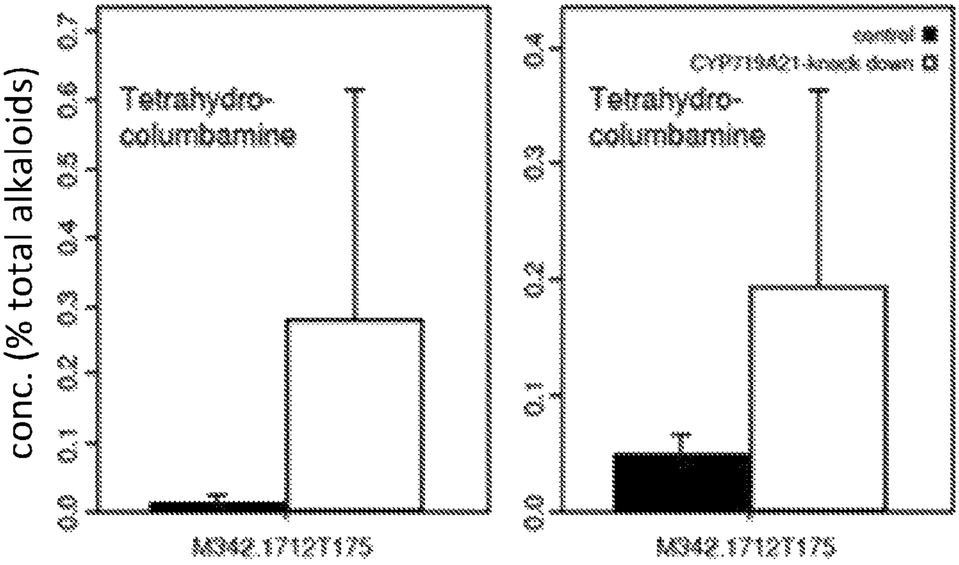

Fig. 4C CYP82X2
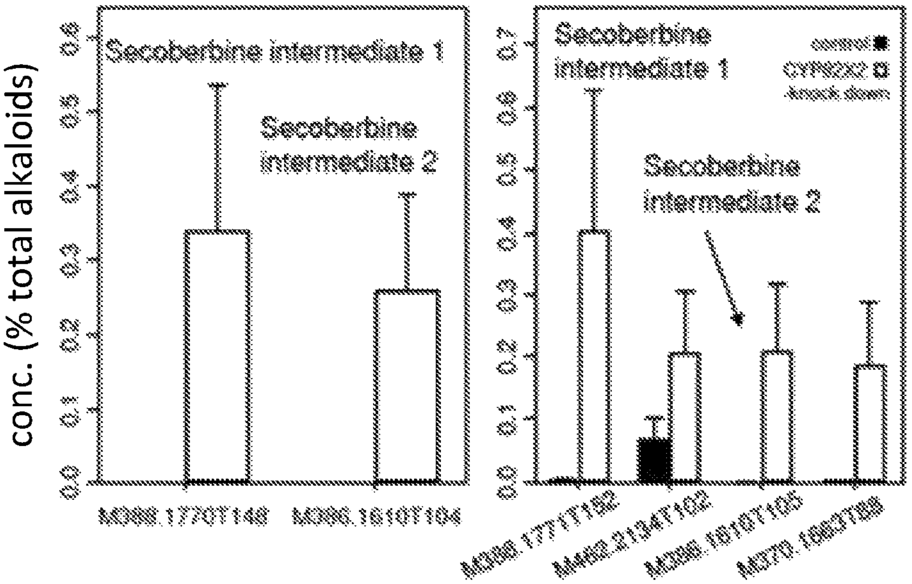
Fig. 4D PSCXE1
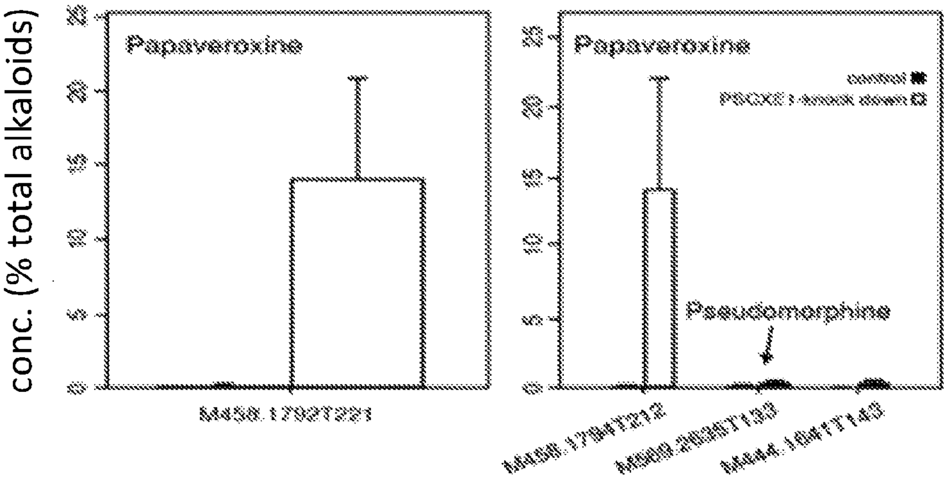

Scoulerine

Tetrahydrocolumbamine

Canadine

*N*-Methylcanadine

Secoberbine intermediates

Secoberbine intermediates

Secoberbine intermediates

Papaveroxine

Desmethylpapaveroxine

Narcotinehemiacetal

Narcotolinehemiacetal

Noscapine

Narcotoline

Fig. 7A

SEQ ID NO: 1 *PSMT1*

| Start | End | Feature |
|---|---|---|
| 1 | 66 | 5′ untranslated region |
| 67 | 877 | exon 1 |
| 878 | 993 | intron 1 |
| 994 | 1058 | exon 2 |
| 1059 | 1841 | intron 2 |
| 1842 | 2138 | exon 3 |
| 2139 | 2306 | 3′ untranslated region |

```
> PSMT1
CACACCAAACTTGATCATTGTCATAAAAAACAGTCCTAATTGTCATCAATCAAAAACAGTCCTAACATGGCTACC
AATGGCGAAATTTTCAATACCTATGGTCATAATCATCAATCAGCCACAGTCACTAAAATCACTGCTTCTAATGAA
AGCAGCAATGGTGTCTGTTATCTTTCAGAAACGGCTAACTTGGGGAAGTTAATATGCATTCCAATGGCACTAAGA
GCTGCGATGGAGCTAAATGTGTTCCAACTTATCTCAAAGTTCGGAACTGACGCAAAAGTTTCGGCTTCTGAAATT
GCCTCTAAAATGCCAAACGCGAAGAATAATCCTGAAGCAGCTATGTATTTGGATAGAATTCTTCGACTGCTCGGG
GCAAGTTCTATTCTTTCTGTTTCTACTACAAAAAAATCAATCAACAGAGGAGGAGATGATGTAGTAGTACATGAG
AAGCTTTATGGGTTAACAAATTCGTCGTGTTGTTTGGTCCCTCGACAAGAAGACGGGGTGTCATTAGTCGAAGAA
TTGCTATTCACATCTGACAAGGTTGTTGTGGATAGTTTTTTCAAACTGAAATGTGTGGTGGAAGAAAAAGACAGT
GTGCCATTTGAGGTTGCTCATGGTGCTAAAATCTTTGAGTATGCTGCTACAGAACCAAGAATGAATCAAGTATTT
AACGATGGAATGGCAGTTTTCTCTATTGTTGTTTTGAGGCTGTTTTTAGAGTTTACGATGGATTTCTTGATATG
AAAGAATTGTTAGATGTTGGTGGTGGTATTGGTACTTCGGTTAGTAAGATTGTTGCTAAATACCCTTTGATTCGC
GGTGTCAACTTCGACTTGCCTCATGTTATTTCTGTTGCCCCTCAATACCCAGGTATACCTTCTTCTTCTTTTTTC
TGAAAAGAACGGGTTCGAATTTTTACAGAATTTTTTTTCTCATTCGATACTCAAGCAACTCTATTAAAGTATACT
GTGTAATAATGCATGCAGGTGTAGAGCATGTTGCAGGAGATATGTTCGAGGAAGTCCCAAAGGGTCAAAACATGT
TGCTAAAAGTAAGCTAACCATACTCAATTTTCTTAATAATTAGGAAAATTGCAAAAACCGTCACAATATTATAAA
GGCATCTGAAGTGCCATCACTCAGATACCGATGCTATGTACTCTATACATTGACAAAATTCCATGGTATCAAGTC
TCAACCTGCCGGTTATAATAATTTTTTTCAGGCTTTCTTTAAAAGAAATTATTTTGAATGGTAAAAATCATCATT
ATATTGGAGAAAAGTGCAGATCTTGCTACATTAAAATTTATAATATAATAAAACATTTGTTTATGGTTGTTTGAA
AAAAAAAATCTCATTGTTAATGCATCTTTCTAAGTTAATGGTGATTAATGGTGAATAATATGATATCTTATTACC
GTCTTCACACTTTTTTTTTTGTCGTAGACAAAATATTTCCAACTTTTCTATATTAATAAAATCAGAAATATTTCA
TTTATATGAATATTAAAATAAGAAGGTGCATGAGTAATATTCCAAATTTCTTAAAGCGTTTTTTATAGCAGTACG
GCGTTTTCTCAAATCTTATTAACCCATAATTAAAGGGTTTCCGTAAATTAAATTGAGGGATATCAAAACAAAAAC
AAAAAATAGGGTTATTTTGCAGTAAAATCAATAACCCCTTATCATATGAAAAGGATAACTTAGTCTACCCCAATT
TGGAGAGATATGGGCAATTATTGTATTACTAGTTCGTTTGAGCATTGATAATATTTTTCATTAGATTTATACTCA
ATAAAATATATGAACTATATTGATAAAGATTAATAATGCAGTCGGTACTCCACGATTGGCGTGATGAACCATGTG
TGAAGCTGTTAAAGAATTGTTGGAACTCATTACCTGTGGGTGGAAAAGTTTTGATAATCGAGTTTGTTCTCCCGA
ATGAACTTGGTAACAATGCTGAATCATTCAATGCGTTGATTCCCGATTTACTCCTGATGGCTCTGAATCCAGGCG
GTAAAGAGCGAACGATTTCCGAATACGATGATTTAGGCAAAGCAGCTGGATTCATAAAAACTATACCTATCCCTA
TCTCCAATGGTCTTCATGTCATTGAGTTTCACAAATGAATGGTTATTGAGTGCTTTGGTAATTAAACTACCAAGA
TAACTACATCCATTTCATGCATTTGCTTTTTTTTTTTTCTTTTTTTTCTTTTTTTTTTCTTTTTGTTTTGTATTCCA
GGTGTGAACTAGTTAGTGTGTTGAGTGGACAAAAGTAAGTAATCGTATTTTGTGTT
```

Figure 7B

SEQ ID NO: 2 *PSMT2*

| Start | End | Feature |
|---|---|---|
| 1 | 74 | 5′ untranslated region |
| 75 | 851 | exon 1 |
| 852 | 938 | intron |
| 939 | 1232 | exon 2 |
| 1233 | 1440 | 3′ untranslated region |

```
> PSMT2
GAATCAGAAACTTTCTTCTAAAATCTTTCAATACCAGTACTGTTAGTTTCCGATAAGAGCCACACTAATCCATTA
TGGAAATTCATTTAGAAAGCCAAGAACAAGAAATGAAATATCAATCTCAAATCTGGAACCAAATATGTGGCACTG
TTGATACCTCTGTTCTGAGATGTGCAATTCAATTAGGTATATTTGATGCCATTCATAACTCTGGCAAACCAATGA
TTACCTTAACCGAATTATCAAGCATTGTTTCATCACCCTCTTCATCTTCAATCGAACCCTGCAACTTGTATAGAT
TAGTGAGATACTTATCCCAAATGGATCTCATTAGTATCGGAGAATGTTTGAATGAAGCAACTGTTTCATTAACAG
GCACATCCAAGTTACTACTTAGAAACCAAGAAAAGAGTTTAATTGATTGGGTATTGGCAATTTCTTGCGAAATGA
TGGTTGTTGTTTGGCACCAACTAAGTAGCTCTGTTTCAACTCCTGCGGATGAGCCTCCAATCTTCCAGAAGGTTC
ATGGTAAAAATGCTTTAGAATTAGCAGGGGAATTTCCAGAATGGAATGATCTGATCAACAATGCTATGACTAGTG
ATACTAGTGTAACTAAGCCAGCGCTAATACAAGGATGTGGCAAAATCCTGAACGGAGTTACATCGTTAATTGATG
TCGGTGGTGGTCACGGTGCCACTATGGCCTACATAGTTGAAGCTTTTCCTCACATAAAAGGTGCGGTAATCGATT
TACCACATGTTGTTGAAGCCGCTCCGGAGCGTCCAGGTGTTGAGTTCATCAGCGGTGATATATTCAAGTCCATTT
CTAACGCTGATGCTGTGTTGTTGAAGGTATGTAAAGAGTAGCTAACCTTAGTGCGTCTAATTTATTCCACAAATT
TTTCTGATGCATTTTATTCTTATTTTTGGTTTTTGCAGTATGTCCTGCACAATTGGGAAGATACGGAATGTGTGA
ATTTACTGAAGAGATGTAAGGAAGCAGTTCCGGCAGACAAAGGAAAAGTGATCATAATGGATTTAGTAATAGACG
ACGATGATAACAGTATTTTAACGCAGGCAAAGTTGAGCCTTGATCTCACTGTGATGAACCATGGAGGAGGTAGAG
AAAGGACTAAAGAAGATTGGAGAAATCTAATTGAGATGTCTGGATTTAGTAGGCATGAAATAATTCCAATATCTG
CCATGCCATCAATTATTGTTGCTTATCCTTAGTTAAGTCACCCGCATGTTTACTTGAACGGGAATAAGTTGGGGG
CGTGTTGAATCTGTTAACATCGCAATTGTGCCTTTACTTTATGCATTCTCATTCCGGTAGAAACTGTTTGGGGCA
TTCGGATTCTGCTGAGCCCTTTTATGTATGTTTGTTTGTTGGTTGGTTGGTTTTCAAGTAACTGAAGTTTCTTCT
CTGTTTTCAAGGCAT
```

Figure 7C

SEQ ID NO: 3   *PSMT3*

```
Start    End     Feature
   1     120     5' untranslated region
 121     846     exon 1
 847     994     intron
 995    1288     exon 2
1289    1436     3' untranslated region

> PSMT3
AAGTTGCAGGTAGGGTTATGAGCAAGCTCAATTATCTCTCCTATAAAAGCTAACATTAGAAAAACTAATAAGCAC
ACAAACCGTAAAAGTTCTGAAGATAGACAAAACAAGAGAAAAAAGATGGAAGTAGTAAGTAAGATTGATCAAGAA
AACCAAGCAAAAATTTGGAAACAAATTTTTGGTTTTGCAGAATCATTAGTTCTAAAATGTGCAGTTCAGTTAGAG
ATTGCTGAAACACTTCATAATAATGTAAAACCCATGTCTTTATCCGAGTTAGCATCTAAACTTCCGGCTCAACCC
GTTAATGAAGACCGTTTGTACCGAATTCTGCATTTCTTAGTTCACATGAAACTCTTCAACAAAGATGCTACCACA
CAGAAATATTCATTAGCTCCACCAGCAAAGTATTTGCTAAAAGGCTGGGAAAAATCAATGGTTCCTTCAATATTA
AGCGTGACTGATAAAGATTTTACAGCTCCATGGAATCATCTTGGGGACGGTTTAACCGGTAACTGTAACGCTTTT
GAGAAAGCGTTAGGAAAGGGCATTCGGGTTTATATGAGAGAAAATCCTGAAAAAGATCAATTGTTTAATGAAGGA
ATGGCTTGTGATACTAGATTATTTGCTTCAGCATTGGTTAACGAGTGCAAAAGTATTTTCAGTGACGGGATCAAT
ACACTTGCCGGTGTTGGCCGTGGTACTGGTACTGCAGTGAAAGCCATATCCAAAGCTTTTCCGGATATTAAGTGC
ACAATCCATGATCTTCCTGAAGTTACCAGTAAAAATAGTAAAATTCCAAGAGATGTTTTTAAGTCCGTTCCTAGT
GCAGACGCCATTTTTATGAAGGTAACTTCTAAGAAATTTTGTTTTAGAATATTCGTTGCAACTCTAATTGACAAC
ATTCATAAAAAATATGTTAATGGTCTTAATTTATTAATTCTAGTAGAGTTACTTAAATGATATACAAAAATTCAA
AATCATATAACATTTGCACAGCATTCTTCACGAATGGAACCATGAGGAATGTATTCAAATCTTGAAACGATGCAA
AGAAGCAATACCAAAAGGGGCAAAGTTATCATTGCGGATGTCGTAATAGACATGGACTCGACTCATCCGTATTC
AAAATCTAGACTCGCAATGGATTTGGCTATGATGCTCCACACGGGTGGAAAAGAGAGAACTGAAGAAGATTGGAA
AAAACTTATTGATGCTGCAGGTTTTGCTAGCTGTAAAATTACTAAACTATCTGCTCTCCAGTCTGTTATTGAGGC
TTACCCTCATTGAGGATAATTTTTATCCTTCTGTTTTCCCTTTGGTTAATTGTTGCCTTCTCTTTGCATCATGCT
TGCGTTTATAATAAATGCAGCGTTTCTTTCCTGGCGGTAAGTGCAAGAAAGAAAAAGCTTCCAGAAACTTCCTTG
AGTATGCCTGG
```

Figure 7D

SEQ ID NO: 4 *CYP82X1*

| Start | End | Feature |
|---|---|---|
| 1 | 130 | 5′ untranslated region |
| 131 | 800 | exon 1 |
| 801 | 881 | intron 1 |
| 882 | 1216 | exon 2 |
| 1217 | 1298 | intron 2 |
| 1299 | 1916 | exon 3 |
| 1917 | 1921 | 3′ untranslated region |

CTTGAGTCATGCCTTGATATGCTCATATTTTAGTTTGTCATATTCACTATAACTATAAATTTCAATACAATTTCT
AAAACTCATCATCATTCAAGACAGATACAAATACCTTGATATCCTTTTATCATCAATGCAGTTATTCATAAAGTT
ACCATTTATCCAACCAATTCCTTTCAGTATTATTCTTGTTACTACAGTTTCGATTGTTCTATTATACAGTGTCTT
CTTCTGGGTTACTGATAAGAAAAAGAAGAGGAAGAAAGCACCAAATGCTGCAGGGGCATGGCCGTTAATAGGTCA
TCTCCGTCTATTGATGAACGACAAGGAACCGTTGTATAGAGCACTAGGGAGCATGGCTGATAAGTACGGACCTGC
ATTCAACATCCGATTAGGTAACCAAGAAGTTCTTGTTGTGAGTAACTGGGAGATGGTAAAACAGTGTTTTGGTAA
TCAAAATGATAAGCTATTTTCGAATCGTCAAACTACATTAGCTGCAAAATACATGCTTAATCAAACAACTTCTAG
CGGATTCGCACCATATGGACCATATTGGAGAGAGCTACGAAAGATAATGGTGCAGCAATTACTCTCTAAACAATC
TTTAGAATCGTGGAAACATCTGAAAATCAAAGAGATGGATGCTTCATTTAGTAAACTTAACGAGTTATGCAACAA
CAACGGTACTGGAACAGCTACCCTAATTAGGATGGACGAATGGTTTGCTGAGTTGACGTTCAACGTGATCGCAAG
AAATGTCTTTGGCTACCAAAGTGGCGGAAGGTCGACAGCGCTTACGAACGGTAATATGATCATACTCCCTCAATC
TGTATCAATTTAAGGAAATCATTTTGGTCTTGTTATTAACTTGAATTTTCTATTAGGAGATACGGAATCAAAGGG
CGAGAGGTACAAGAAAACATTGGAAGAAGCACTTCATCTTATGTCAATTTTTGCAGTTTCAGACATATTTCCAAG
TCTAGAGTCGCTAGATCGGTTAAGAGGCCTTATAAGGAATATGAAACGCTTTGGAGATCAGCTAAATTCAATTGC
AGGGTGTCTTATTGAAGAGCACCGCCAAAAGAGATTACAATCCGTATCTAAAAGTGATAAAGGAGTTGGTGATGA
ACAAGACTTCGTTGATGTTCTCTTATCGGTTGCTGAAAAATCGCAACTTCCTGGAGATGACCCTGATTTGGTCAT
CAAGTCTATGATTCTGGTTAGGCTATTGATACCAAGTCTATTGCAATTTTGGTTTATGTGCTTGTTCTAACTTTC
GTTTACTGCATATGGATGTGCAGGAAATCGTATCAGGTGGGAGTGAGACCACATCGTCAACCTTAACTTGGGCCC
TCTGTCTGTTACTGAACCATCCGCATGTGTTAAAGAAGGCAAAAGAGGAATTAGATACGCACGTAGGAAAAGATA
GGCATGTACAAGAGTCAGATACCCCTAAGCTCGTCTACATTAATCCAATTATCAAAGAATCAATGCGATTCTATC
CAAACGGGGCAATGCTTGATCGGTTGGCGTTAGAAGAGTGCGAAGTTGGTGGATTTCATGTACCGGCCGGGGGAC
GCTTATTTGTCAATGTTTGGAAGATTCAGAGAGATCCGAGTGTTTGGGAGAATCCTCTGGAGTTTAAACCAGAGA
GGTGGTTTTTGAGTAATGGTGAAAAGATGGATGTGGATTACAAAGGTCACAATCATGAATTCATACCATTTGGGA
TAGGTCGGAGGATGTGCGCTGGTATGCTTTGGGCATCGGAGGTGATTCATTTGGTGCTGCCCCGTCTTATTCATG
GGTTTGATATTGAAAGCAGCAAGTGCCAATGGGAAAGTAGATATGGCAGAAATGGCAGGCATGGTGATTTGTTTTA
AGAAGACACCTCTTGAAGTTATGGTCAATCCTCCAGAGTAGATGTT

Figure 7E

SEQ ID NO: 5 *CYP719A21*

| Start | End | Feature |
|---|---|---|
| 1 | 69 | 5′ untranslated region |
| 70 | 1530 | ORF |
| 1531 | 1688 | 3′ untranslated region |

CATGAAATTCTTTATGCAAAGAGTCAATCTGACTCAAGCTAGCTAGAATATATACCAATCATAAAAGAAATGATC
ATGAGTAACTTATGGATTCTTACGCTCATTTCTACCATATTAGCAGTCTTTGCTGCTGTGTTAATCATTTTCAGG
AGAAGAATATCAGCATCCACAACGGAATGGCCTGTTGGCCCAAAAACATTACCAATCATAGGTAACTTGCACATT
CTTGGAGGCACTGCTCTCCATGTCGTCTTACATAAACTTGCTGAAGTTTACGGCAGTGTAATGACGATATGGATT
GGTAGTTGGAAACCTGTTATTATTGTTTCCGACTTTGATCGAGCCTGGGAAGTTCTTGTTAACAAATCGTCAGAT
TATTCAGCTCGTGAAATGCCTGAGATCACTAAAATCGGCACTGCAAATTGGAGAACAATTTCAAGTTCTGATTCT
GGTCCGTTTTGGGCCACTCTTCGAAAAGGTCTTCAGAGTGTAGCATTATCGCCTCAGCATTTAGCATCGCAAACT
GCACACCAAGAGAGAGATATAATAAAGTTGATCAAAAATTTGAAAGACGAAGCAGCTTCTGGAATGGTTAAACCA
CTTGATCATCTCAAGAAAGCAACTGTAAGATTAATCAGTCGGTTAATCTATGGTCAGGATTTTGATGACGATAAG
TATGTTGAAGATATGCATGACGTGATCGAGTTTTTGATTCGTATTAGTGGTTATGCTCAACTTGCTGAGGTATTC
TATTATGCTAAATATCTACCAGGTCATAAGAGAGCTGTAACTGGCGCCGAAGAAGCAAAAAGAAGAGTAATAGCT
CTGGTGCGTCCTTTTCTTCAGTCAAACCCTGCTACTAACACTTACTTGCATTTTCTCAAATCGCAACTGTATCCT
GAAGAGGTTATCATATTCGCTATATTCGAAGCTTATCTTTTAGGTGTTGATAGCACTTCTTCAACCACTGCATGG
GCACTCGCATTCTTAATACGCGAACCATCTGTTCAAGAGAAACTTTATCAAGAGCTTAAGAATTTCACAGCCAAT
AACAATCGCACAATGCTGAAAGTCGAAGACGTCAACAAATTACCATATTTACAAGCTGTTGTTAAAGAAACAATG
AGGATGAAACCAATTGCACCACTGGCGATTCCTCATAAAGCTTGTAAAGACACTTCATTGATGGGCAAGAAAGTT
GATAAGGGAACTAAAGTTATGGTTAACATTCATGCTTTACATCATACTGAAAAGGTTTGGAAAGAACCTTACAAA
TTCATACCAGAGAGGTTTCTGCAGAAGCACGATAAGGCGATGGAACAATCACTATTACCATTTAGTGCAGGTATG
AGAATTTGTGCAGGAATGGAATTAGGAAAACTTCAGTTTAGTTTTTCTCTTGCTAATCTTGTTAATGCTTTTAAA
TGGTCTTGTGTGTCTGATGGAGTGCTTCCTGATATGAGTGATTTACTGGGGTTTGTTCTGTTCATGAAAACCCCA
CTCGAAGCACGTATAGTTCCTCGTTTGTAGTGATGGAAATTTCATCTCATGTTGTTGTTTCTCTTCATGTTTACT
ATTTCGTACTCGTTTGGTTTTGGTGTAAAAAATAAGATCTAAACTTCCAAATATCATTAATGTTTACACAAATCG
AAATCAATCAACTATGTTATGAAAATTAGTGTTTTCTC

Figure 7F

SEQ ID NO: 6 *CYP82X2*

| Start | End | Feature |
|---|---|---|
| 1 | 783 | promoter sequence |
| 784 | 893 | 5′ untranslated region |
| 894 | 1581 | exon 1 |
| 1582 | 1694 | intron 1 |
| 1695 | 2050 | exon 2 |
| 2051 | 2170 | intron 2 |
| 2171 | 2791 | exon 3 |
| 2792 | 2918 | 3′ untranslated region |

```
>CYP82X2
AAGTGTGCCACTAATCTACTGCTAGTGCTACTGCTCACTGACACTTACACATATGATTGATTTATGGCTAAACAG
GATGACCACTAAATTTATTTTGGAAAGCGGAGTGAATTAATTAAGTGGCACATTTTCCATGAGAATTATTGATGG
CATGCATTTAGATGAACAAGATACACCAAATGTAGTGACTGAACAAGATGCTCGATCCTAACCCCACCTGCAACT
TTAGCTAAACTTTAATAATTACATGTCTTATCTTTTTATTGAATCATTTTATCTATCAATGGATGCTGATCAATA
ATATCATATATCTTTGCTTTTTCTTCAATCATTTAGATGAACAAAAAACACAATAAGTGTAGTGGTTGTTCATAA
CCCCACCTTCAACTCATTCTTCCCTTTAATAACAAATATCTTTGCTTTTTCTCCAATCATTTACTTGAACAACCA
ACACTAGTAAGTGTAGTGGTTTCTCATAACCCCACCTGCAATTTTTGCTTACCTTTAATAACATATATCTTTGAT
TTTCTTCGATCATTTTAGCTACCAATGGATGCTGATCCAAAAAGTTATGGCAAAAAGAGACAACGTGATCGAACA
CGAGCCTCTCGTGCACCACAGCATCAAGGTTTGTGGAAATTAACCGCTTGTAAAAAATGGAGTGCGTGATCATAA
TGAGGTATTGCTAAGATATAGTATCAACTTTAGTGAACTGGGCCAACAAAACTCACGAGTTGTTGAAAATTGGAG
ATTATATTTATAAGATAAAAGGGTCACTCCCTACACAACGACTTGCACTGCAAGTGAAAAAGAAAAAAAACAAAC
AACCTCAATCTAGCTAGAGTCGTGAAAAAGTTTTGTGCGACTGTTATTTAGTTAATTATAAAATTTCAATGAAGT
CGTTAATGATGAACAAGTTATTATTTCTCCAACGGATTACTGATTCTCCTTCGACCACCATTATCAGTACTTTTA
TTGTTACAATAATATCCATTGTTTTTCTCTACACTGTCTTGTTGATAAGGACGACTAAGAATAAGCAGAAGATAG
CAGCACCAAAAGCATCGGGGGCGTGGCCGTTCATAGGTCATCTCAAACTATTCATGAAACAAGATACTCAGTTTT
ACAGAACTCTAGGAACCATGTCTGATAAATACGGGTCGGTGTTCACACTTCGATTAGGAAACCAAGCAATCCTAG
TTGTGAGCAACTGGGAGATGGTAAAAGAATGTTTCACAACAAACGACAAGTCATTCTCGAATCGTCCAAGTACGT
TAAGCACTAAATACATGCTGAATGACACTAATTCTGTCGTGTTTTCACCTTACGGAACGTATTGGAGAGAAATGC
GGAAGATATTGGTGCAAAAACTACTGATCTCTAACCAAAGATCAGAGGCATTGAAAAATCTGAAAACGAAAGAAA
TCGACAACTCGTTTGTAAAGCTTAATGATTTATGCAACAACGATGTCAGTGGAGGAGGCACAAAAGTTAGGATGG
ACGAATGGTTGGCTGACATGATGTTCAACATTATTGCTAGGATTACATTTGGTTACCAAAGCGGAGGAGGCGATG
CACCTGGTATGTGATCATCAAATTTTCGTTAAAACCAAATTAACTTGTACTATATCTTATGTTTACATGTTATAT
TGATCACTTTGACACGTTCTGATCATTTTCACAAATCGAATTAGGCGCTTCTACAACATCCAAGAATGTCGAGAG
ATACAAGAAAACGTTGGACGAGATGTTTGTTGTTTTAGCGACGAGGTTTGCAGTTTCAGATATATTTCCATCTCT
GGAGTTTATAGACCGATTGAGAGGTCTTGTAAAGGATATGAAAATCTTGGGAGACGAATTAAACTCCATTGCTGG
ATGTTTTATTGAAGAACATCGTCAAAAGAGACGAGAATCATTATCCTCATTGTTATCTTTGTCAAATGAATCCGT
TGGTGATGAACAAGATTTCATTGATGTTCTCTTGTCAATAATGGATCAGTCACGGCTTCCCGGAGATGACCCAGA
TTTTATTATCAAAATTATGATCCTGGTAACATATATTACAACAGTATTTCTTTAAGTTATGGATTAATGGATGTC
GTAACCATGAATATTTTTCTGATCTGGATAAATGTAATCCGGAACTAATATATGAATATTGTTGACGCAGGAAGC
TTTTGCAGGTGGGACGGACAGTTTAAGTGCAACCTTAACTTGGGTCCTCTCTCTACTGCTGAACCACCCAAACGT
GTTAAAGAGGGCAAGGGAGGAAATAGATAGGCATGTGGAAAACGGTAAGCAAGTGGAAGTGTCTGATATTCCGAA
GCTCGGATACATTGATGCAATAATCAAAGAGACGATGAGATTGTATCCAGTCGGAGCATTAAGCGAACGATACAC
GACTGAAGAATGCGAGGTTGGTCGGTTTAACGTACCCGCTGGCACACGCTTACTGGTGAATATATGGAAGATCCA
CAGAGACCCAAGTGTGTGGGAGAATCCATCAGATTTTCAACCAGAGAGGTTTTTGTGCAGCGATAAGGTGGGTGT
GGATTTATATGGCCAGAATTATGAGCTGATACCATTTGGGGCCGGTAGGAGGGTATGTCCGGCTATAGTTTCATC
ACTGCAGACGATGCATTATGCGTTGGCGCGTCTTATTCAAGGATATGAAATGAAATCAGCCAGCCTCGATGGGAA
GGTGAATATGGAAGAAATGATAGCCATGTCGTGCCACAAGATGAGCCCTCTTGAAGTTATTATCAGTCCTCGGGA
GCCGAGGCGGAGTTAAATCTTATGTTCCAATTTTACATTAGCATCTTTGATTATGAAATGTATTGCTCTTAAGTT
TCTTTTTTGTTTTTTATATTTTTAAGCTTGTATGTGATCATCAGCGAAAATGATGATGACAGAATCGT
```

Figure 7G

SEQ ID NO: 7 *CYP82Y1*

| Start | End | Feature |
|---|---|---|
| 1 | 12 | 5′ untranslated region |
| 13 | 718 | exon 1 |
| 719 | 815 | intron 1 |
| 816 | 1153 | exon 2 |
| 1154 | 1237 | intron 2 |
| 1238 | 1864 | exon 3 |
| 1865 | 1915 | 3′ untranslated region |

```
> CYP82Y1
TTCAGTTCATTCATGGCGTATTTGATGATCAAGAAGTCTATCTATTTGTTTTTTGATCAACCAACTGCAGTTGGC
ACTCTTATACTTGCTTTTCTGCTGACACTTTCGCCTGTTATTATTTACTATGAACAGAAGAAGAGGGGTTTGAGG
CGAAATCGCACCGCAATTACAACGACTCCATTACCAGAGGCATCAGGTGCATGGCCAGTGATAGGTCATCTTCTT
CTTTTCATGAACGAAAACGATCTAAATCATGTAACTCTTGGTCACATGGCTGATAAATATGGACCTATTTTCAGC
TTAAGATTCGGTAGACATAGAACTCTAGTTGTTAGTAGTTGGGAGATGGTAAAGGAGTGTTTTACAGGTACCAAT
GACAAGTTGTTCTCAAATCGTCCTTCCTCCTTGGCGGTTAAACTTATGTTTTATGACACTGAATCTTATGGTTTT
GCACCTTATGGGAAATACTGGAGAGAGTTGCGAAAGATATCTACACACAAACTCCTCTCTAATCAGCAATTAGAG
AAGTTCAAGCACTTGCGGATTTCTGAAGTCGATAACTCCTTTAAAAAGCTTCATGAGTTATGCAGCAACAACAAA
CAGGGAGGTGATACTACATATGTGGCTAGTCTTGTGAGAATGGATGATTGGTTCGCGTACTTGACATTTAACGTA
ATAGGACGGATCCTCACCGGATTCCAATCAAATGCAGTGGCAGCTCACCTCATATAGCTAGGTTTTTATATGTTT
GGTTTGTACACACACACCTCATTCATATTCTAAACTGAATTATATCTTATAATTGAACAACATAGGTGCCACAAA
CAGCCAGGAAAAATACAACCTTGCAATCGATGAAGTGTCAAATCTTATGCCAACGTTTGCCGTTTCAGATGTGGT
TCCACGGCTTCGCTCGATTGATCGATTGACTGGTCTTACAGCAAACATGAACAATTGTGGTAAAAAATTAGATGC
AGTAGTTGGGCATGCACTCGAGCATCATCGCCAAAAGAAACTCAAAATTTCTACAAATAACACAGGAGCACTTAC
GGAGCACGAAGAAGAAGACTTTATCGATGTTTGCTTGTCGATTATGGAGCAGTCACAGATTCCGGGAAACCACCC
CGAAATCTCTGTCAAATCTATTGCCTTGGTAATACGTCTCATAAGCATGTTAGCAGATTTTACCTCTATATATAC
TTACATATTATTTTTTATCAATCACACATATGTGCAGGACATGTTATCGGGTGGGAGTGACACTACAAAATTGAT
AATGACATGGACCCTTTCTTTGCTGTTGAACCATCCAGACATATTGGACAAGGCTAAAGAAGAAGTAGATACATA
CTTCGGGAAGAAAAAGATATCGGATAACACACCTGTGGTTGATGCTGCCGATGTTCCTAACCTCGTCTACATCCA
AGCAATCATCAAAGAATCAATGCGGTTATACCCTGCTAGCACATTGATGGAGCGAATGACAAGTGATGATTGTGA
TGTTGGTGGCTTCCACGTACCAGCTGGGACACGATTATGGGTTAACGTATGGAAGATGCAACGGGACCCAAGGGT
GTGGAAAGATCCACTGGTATTTCTACCTGAGAGATTCTTGAGCAATGACAAAGGGATGGTAGATGTGAAGGGTCA
GAATTATGAACTGATACCATTTGGAACAGGCAGGCGGATATGTCCTGGTGCATCTTTTGCCTTGGAAGTCTTGCA
TTTGGTTCTTACTCGTCTTATTCTTGAGTTCGAGATGAAGGCACCAGAGGGGAAAATTGACATGAGGGCAAGACC
AGGTTTTTTCCACAACAAGGTGGTGCCACTAGATGTTCAACTCACCCCACGCACACTAGATTAAGATTCCTATAT
ATGCTAATTAATTAGATGAATAAAATCTGTGGTCGAGTAA
```

Figure 7H

SEQ ID NO: 8 *PSCXE1*

| Start | End | Feature |
|---|---|---|
| 1 | 15 | 5′ untranslated region |
| 16 | 978 | ORF |
| 979 | 1333 | 3′ untranslated region |

>PSCXE1
AATAAAAATCCAACAATGGCAGATCCTTATGAATTCCTAATGTGCATTCACAATCCTGAAGAAGATACCCTAACA
AGAAATTTTCCGATTCCTGCTACTCCCTTAGATCAAAACACCAAAGACATTTCTTTAAATCCTGATAGGAAAACC
TCACTTCGAATCTTTCGGCCACCAACCAAAGAACCTCCTGTAACAAAGAATAAGCTGCTTCCTATCATAATTTAT
TTCCATGGTGGAGGTTTCATTCTTTTCAATGCAGATTCAACTATGAACCATGACTTTTGTCAATCGATTGCTACA
CATATACCCGCGCTGGTCGTTTCTGTAGACTACCGTCTTGCTCCTGAAAACCGACTTCCCGCTGCCTATGATGAT
GCTGTTGATGCTTTAAACTGGGTCAAAGACCAAGGTTTAGGCAAACTAAATAATAGTGAAGTATGGTTAAAAGAG
TATGGTGACTTCTCAAAGTGTTTCATTATGGGGTGCAGCTCAGGTGCTAATGTTGCATATCATGCCAGTTTAAGA
GCAATAGAAATGGATCTTGAACCAGCTAAGATTAATGGATTAATATTACACTGCCCTTTTTTTGGTAGTCTTGAG
AGAACTGAATCAGATTCAAAAGTGATCAACAATCAGGACTTGCCGCTTGCCGTAAGGGATGTCATGTGGGAACTG
GCGTTGCCGCTTGGGTCTACTCGTGATCACGTTTATTGTAATCCGAATATTGATCATGATGGATCATCATCTGGA
AATATGGTGGGGTTAATCGAGAGATGTTTTGTGGTAGGATTTTATGGGGATCCACTTATTGATCGACAAATTCAG
CTGGTGAAGATGCTGGAGGAAAAAGGTGTGAAGGTTGAAACTTGGATTGAACAAGGAGGGTATCATGGGGTGCTA
TGCTTTGACCCTATGATACGTGAAACCTTTTTGGAAAAACTAAAACATTTTATTTTAAACGACGAATTTATATAC
TAAAATATATTATTAGTATTAAACAATGAAATTCTTATTTTTTCTAAAATGAGCTTTTGGACGAAACATTGTGTA
CGAACTAGCTGATGTAATTTTTCGTTTTACCGGATTTTTCATTTTTTTTGCTTTCTTTCTGCTCTCTTTTATAAG
TCGTTCTT

Figure 7I

SEQ ID NO: 9 *PSSDR1*

| Start | End | Feature |
|---|---|---|
| 1 | 254 | 5′ untranslated region |
| 255 | 423 | exon 1 |
| 424 | 635 | intron 1 |
| 636 | 1178 | exon 2 |
| 1179 | 1953 | intron 2 |
| 1954 | 2146 | exon 3 |
| 2147 | 2236 | intron 3 |
| 2237 | 2378 | exon 4 |
| 2379 | 2488 | 3′ untranslated region |

```
>PSSDR1
CTAACAGGCAAACAATAACAGGTTGCACCTACAACATTCAATTTTTATTTTGGTAAATGAAGTTCAGTTGGAGAGTAACCACA
TCTTTGTTGTCGGCATTGCCCCCACAATACTGAGTGTTTTGGCTGAGTGTAGTCTGACTGTAGGTAAGCTACAACTGCATGTT
GCAGATAATAATCACTAACTGATTATTCATGCATACCTAACAGTCATATTGTTATAGTTCCCAAAAAAAATTCTCGAACTATA
AACGCATGCATGCACAGAAAAATATATCAGAGACATATCAGAAATTCAAAGAGATGGAACCAACACGGAACATACTATGTCTA
ACAGGTGGAGCTGGATACTTGGCATCTTGGCTGATCATGAGATTGCTTGAACGTGGTTACTCTGTTCGGACCACCGTTCGGTC
TGACCCAAGTACGTAATAAATTAAATTTCCTGGCATCATTTTCTTCAATATAAATTTCTTATTATCTAGTTCATCATTCTTTA
TTGTTCCAATCATGTCCCCCCAAGTCTAAAAGAAGTAGTAATCTAAAAATAGCTAATTTATGTACGAAATTGTAACAATGATC
TCCTAGCTTATGAGGCTCACCTAATTTCGTTTCTATCATTTTGTGTCTTGAAAGAATTTAGGGAAGATGTGAGCCACCTTAAA
GCTCTTCCTGAACCTACACAGAACCTTCAAATTTTTGAAGCAGATCTTGAAAACCCAGAAAGTTTCGACCATGCCATCAACGG
TTGTGTCGGTGTCTTTCTCGTTGCTCAAGGAATGAATTTTGCCGAAGAATATACTCTTGAAAAAATAATCAAAACATGCGTGG
AAGGAACTCTTAGAATTCTACAGTCATGCTTGAAATCTAAAACAGTGAAAAAGGTTGTGTACACATCTTCTGCTGATGCAGCA
ATGATGATAAGTAATCTCAAAGCTGTTAAAGAAATTGACGAGACAATATGGTCAGAAGTTGACAATTTCATTAGCAAACCGGA
ACAAGTTATTCCTGGATTGCCCTCATATGTGGTTTCAAAGGTACTGACAGAAAGAGCTTGCCTAAAGTTTTCTGAAGAACATG
GTTTGGATGTTGTTACTATACTTCCTCCGTTGGTTGTTGGACCTTTTATCACTCCCCATCCTCCTCCCAGTGTATCTATAGCT
CTTTCGATAATTTCAGGTATCCTCTCCATCCGAAAAATATGCCAATTCCTAAACTTAAAAGGCATATTGATATTTAATAATAC
CTCCATACCTAAAAAAAGAGTTGCTATATAACATTTTTAATTTTCGCCCATTTTTAGGCCTAATTGAAAAAGTTATAATAACA
TTTTAGCAAGGACGGAGAATGATTTTTCAGCAAACCTTAGAACTCTGTGCTGACATTTGTCCGTTATCATTGTTCCTATAACT
GTGTATATCATGGTTTTTAAAAGCGCCGCTCACGCTACGCTTCGTACGGTTCGGTCTAGATTTTTTAATTCGCTCCGAAGCG
TAGTTATGAAGCTACCATGAAGCGCCGCTTCACGCTACGTTTCGTACGCTTCGCTTCAGATTTTTCAAATTCGCTCCGAGGCG
AATCTACCATGAAGTGGAAGATTCCTTTAATTGATTCACTTTTTTACTTAGTCAAGTCTTTTTTAGGGGGTTTCGAAAACTAA
AGTGAACCACTGCGCCTCGCTACTGTTTTTGAAATTAACTAGACTTATATTAAATTGATACAATTATTATATCTTCCTAAATA
TTAAATTATTAATAACAAACTACTACTATTTATAGGAAAAAATTCGCTTCAAATATCAATCATAAAACGACGCTTCACATTTC
AACATGCGCATCGCTTCGTATAAAAAAAAAACGCTTCACGCTTTCAATACCTTGGTGTACATAGATTAATACTTCCTCCTCTG
CGCTGGTGTTAACATTTCTGTGTTTCGTTTATATATATGACCAGGTGATGTGTCGATGATGCTTGGTGTTAGACTTGAAAATG
CCCTACATATAGATGATCTTGCTTTAGCACACATATTCGTTTTTCAATGTGAAAAAGCAAAAGCAAGACATATTTCTTCTTCA
GTTGATTTTCCAATGCATGATCTGCCTAAATTTATATCTGAGAATTATCCGGAATTCAACGTACCGACTGAGTGAGTTTATCT
TTCACCACCTTCTTTATTATTATTCATCAAGTCACTTTGGGTATTTTAACCTTATTGTTTTTACTGAATTATCATCAGTTTAC
TAAAGGATATTGAGGAACAAGAACCAGTTCATCTTTCCTCAGATAAGCTGTTGAGTATGGGATTTCAGTTCAAATATGATTTT
GCAGAGATTTTCGGTGATGCAATACGATGTGCCAAAGAGAAGGGTTTCCTTTAGAGACCAACTATAGTTTGGTTCGGAGGAGA
TGTGGGAGTAGCTAGCCCAAAATGCCCTGCTCGCACTAGCTTATATTATTGTTATTGTTTTTCAAATGAATAAACGGGCAG
```

Figure 7J

**SEQ ID NO: 10 *PSAT1***

| Start | End | Feature |
|---|---|---|
| 1 | 53 | 5′ untranslated region |
| 54 | 1469 | ORF |
| 1470 | 1572 | 3′ untranslated region |

```
> PSAT1
CGCATATAATCCAATTTGCATTGTTTATCGACCTTGAGGAACAATTAGGGGATATGGCAACAATGTCTAGTGCTG
CTGTAGAAGTGATCTCGAAAGAAACGATTAAACCAAGAAATCCAACACCATATCAACTTAGAAACTACAATATGT
CACTTCTCGACCAATATTCTTCTCTAGTTTATGTTCCGATCATTCTTTTCTACCCTGCTGCCTCCGACGCTAATA
GTACCGGAAGTAAGCACCATGATGATCTTCACTTGCTTAAGAGGTCTCTTTCTGAAACGCTAGTTCACTTTTATC
CAATGGCTGGTAGGATGAAAGACAACATGACTGTTGACTGTAACGACGAAGGTATTGACTTTTTCGAAGTAAGAA
TCAAAGGTAGAATGTGTGACTTCATGATGAAATCAGATGCACACTTAAGTCTGCTTCTTCCGTCTGAAGTCGCTT
CCACGAACTTCGTGAAGGAAGCACAGGTGATTGTTCAAGTGAACATGTTTGATTGCGGTGGAACTGCCATTTGTT
TCTGTATATCAAACAAGATTGCAGATGCATGCACCATGATTACCTTCATTCGTAGTTTGGCAGGCACCACCAACA
TAGCTCGTCGTGGGAGCTCTATTGCTGCACCAACCACAAATCAGAATTTGGTTCCTTCTTTCGATTCGACATCAC
TCTTTCCACCTAGTGAACAATTGGCATCTCAAGTTTCCTATCCTACACAGGATAGTACCAGCGTAGATAAACTTG
TCAGCAAAAGATTTGTGTTTGATGCGGCAAAGATTACATCTGCACGTGAAAAATTGCAATCCTTGATGCATGATA
AATACAAATGCCATAGGCCGACAAGGGTTGAGGTAGTTTCCGCTTTGATATGGAAGTCAGCAGTGAAATCTGCTC
CGCCCGGTTCTATATCCACTGTAACCCATGCCATGAACTTTAGAAAGAAAATGGATCCACCATTACAAGATGCGT
CATTCGGGAATCTTTGTGTGGTTGTTACAGCAGTATTACCAGCAACAACGGCGACAACAACAAATCCAGCAACCA
AAAAAGTTAGTAGTACGAGTAATGAAGAGCAAGTGGCACTTGATGAGTTAAGTGATTTTGTAGCCCTATTGAGGC
GCGAAATAGATAAGCTAAACGGTGATAAACGTTGCATCGAGAAAATCATTCAAAAGTTCATCTATGGTCATGATG
CTTCCGTAGCGAAAGACAGTGATGTTGAAGATAAGGTGACAGCTTTGTTTATGACTAGCTGGTGCAAGTTTGGAT
TCTACGAAGCTGATTTTGGTTGGGGAACGCCAGTTTGGGTAACTACTGTTCCATTAATTGAGCCAAAGTACAAGA
ACATGGTTTTCATGAACGATATGAAATGTGGTGAAGGAATTGAAGTGTGGGTGAATTTTCTGGAGGATGATATGA
CCAAGTTCGAACACCACCTAAGAGAGATCCTCCAACTGTTTTGATTTTCAACCGTTTCCCTAATAGAGGTCAATT
GTCGTGTTTCTCCATCTTAACTACCATCTTTATTCTCTTGTTTTCATACTTGTATTTGTCTTACTCCCGTAA
```

SEQ ID NO: 11PSMT1

```
MATNGEIFNTYGHNHQSATVTKTTASNESSNGVCYLSETANLGKLICIPMALRAAMELNVFQLISKFGTDAKVSA
SETASKMPNAKNNPEAAMYLDRTLRLLGASSILSVSTTKKSINRGGDDVVVHEKLYGLTNSSCCLVPRQEDGVSL
VEELLFTSDKVVVDSFFKLKCVVEEKDSVPFEVAHGAKIFEYAATEPRMNQVFNDGMAVFSIVVFEAVFRVYDGF
LDMKELLDVGGGTGTSVSKIVAKYPLIRGVNFDLPHVISVAPQYPGVEHVAGDMFEEVPKGQNMLLKWVLHDWGD
ERCVKLLKNCWNSLPVGGKVLITEFVLPNELGNNAESFNALIPDLLLMALNPGGKERTISEYDDLGKAAGFIKTI
PIPISNGLHVIEFHK.
```

SEQ ID NO: 12 PSMT2

```
MEIHLESQEQEMKYQSQIWNQICGTVDTSVLRCATQLGIFDAIHNSGKPMITLTELSSIVSSPSSSSTEPCNLYR
LVRYLSQMDLISIGECLNEATVSLTGTSKLLLRNQEKSLTDWVLAISCEMMVVVWHELSSSVSTPADEPPIFQKV
HGKNALELAGEFPEWNDLINNAMTSDTSVTKPALTQGCGKILNGVTSLIDVGGGHGATMAYIVEAFPHIKGAVID
LPHVVEAAPERPGVEFISGDIFKSTSNADAVLLKYVLHNWEDTECVNLLKRCKEAVPADKGKVIIMDLVIDDDDN
SILTQAKLSLDLTVMNHGGGRERTKEDWRNLIEMSGFSRHEIIPISAMPSIIVAYP.
```

Figure 7K

SEQ ID NO: 13 PSMT3

MEVVSKIDQENQAKIWKQIFGFAESLVLKCAVQLEIAETLHNNVKPMSLSELASKLPAQPVNEDRLYRILHFLVH
MKLFNKDATTQKYSLAPPAKYLLKGWEKSMVPSILSVTDKDFTAPWNHLGDGLTGNCNAFEKALGKGIRVYMREN
PEKDQLFNEGMACDTRLFASALVNECKSIFSDGINTLAGVGRGTGTAVKAISKAFPDIKCTIHDLPEVTSKNSKI
PRDVFKSVPSADAIFMKSILHEWNDEECIQILKRCKEAIPKGGKVIIADVVIDMDSTHPYSKSRLAMDLAMMLHT
GGKERTEEDWKKLIDAAGFASCKITKLSALQSVIEAYPH.

SEQ ID NO: 14 CYP82X1

MELFIKLPFIQPIPFSIILVTTVSIVLLYSVFFWVTDKKKKRKKAPNAAGAWPLIGHLRLLMNDKEPLYRALGSM
ADKYGPAFNIRLGNQEVLVVSNWEMVKQCFGNQNDKLFSNRQTTLAAKYMLNQTTSSGFAPYGPYWRELRKIMVQ
QLLSKQSLESWKHLKIKEMDASFSKLNELCNNNGTGTATLIRMDEWFAELIFNVIARNVFGYQSGGRSTALINGD
TESKGERYKKTLEEALHLMSIFAVSDIFPSLEWVDRLRGLIRNMKRFGDELNSIAGCLIEEHRQKRLQSVSKSDK
GVGDEQDFVDVLLSVAEKSQLPGDDPDLVIKSMILEIVSGGSETISSTLTWALCLLLNHPHVLKKAKEELDIHVG
KDRHVEESDTPKLVYINAIIKESMRLYPNGAMLDRLALEECEVGGFHVPAGGRLFVNVWKIQRDPSVWENPLEFK
PERWFLSNGEKMDVDYKGHNHEFIPFGIGRRMCAGMLWASEVIHLVLPRLIHGFDMKAASANGKVDMAEMAGMVI
CFKKTPLEVMVNPRE.

SEQ ID NO: 15 CYP719A21

MIMSNLWILTLISTILAVFAAVLIIFRRRISASTTEWPVGPKTLPIIGNLHILGGTALHVVLHKLAEVYGSVMTI
WIGSWKPVIIVSDFDRAWEVLVNKSSDYSAREMPEITKIGTANWRTISSSDSGPFWATLRKGLQSVALSPQHLAS
QTAHQERDIIKLIKNLKDEAASGMVKPLDHLKKATVRLISRLIYGQDFDDDKYVEDMHDVIEFLIRISGYAQLAE
VFYYAKYLPGHKRAVTGAEEAKRRVIALVRPFLQSNPATNTYLHFLKSQLYPEEVIIFAIFEAYLLGVDSTSSTT
AWALAFLIREPSVQEKLYQELKNFTANNNRTMLKVEDVNKLPYLQAVVKETMRMKPIAPLAIPHKACKDTSLMGK
KVDKGTKVMVNIHALHHTEKVWKEPYKFIPERFLQKHDKAMEQSLLPFSAGMRICAGMELGKLQFSFSLANLVNA
FKWSCVSDGVLPDMSDLLGFVLFMKTPLEARIVPRL.

SEQ ID NO: 16 CYP82X2

MKSLMMNKLLFLQRITDSPSTTIISTFIVTIISIVFLYTVLLIRTTKNKQKIAAPKASGAWPFIGHLKLFMKQDT
QFYRILGTMSDKYGSVFTLRLGNQAILVVSNWEMVKECFITNDKSFSNRPSTLSTKYMLNDTNSVVFSPYGTYWR
EMRKILVQKLLISNQRSEALKNLKTKEIDNSFVKLNDLCNNDVSGGGTKVRMDEWLADMMFNIIARITFGYQSGG
GDAPGASTTISKNVERYKKTLDEMFVVLATRFAVSDIFPSLEFIDRLRGLVKDMKILGDELNSIAGCFIEEHRQKR
RESLSSLLSLSNESVGDEQDFIDVLLSIMDQSRLPGDDPDFIIKIMILEAFAGGTDSLSAILIWVLSLLLNHPNV
LKRAREEIDRHVENGKQVEVSDIPKLGYIDAIIKETMRLYPVGALSERYTTEECEVGRFNVPAGTRLLVNIWKIH
RDPSVWENPSDFQPERFLCSDKVGVDLYGQNYELIPFGAGRRVCPAIVSSLQTMHYALARLIQGYEMKSASLDGK
VNMEEMIAMSCHKMSPLEVIISPREPRRS.

SEQ ID NO: 17 CYP82Y1

MAYLMIKKSIYLFFDQPTAVGTLILAFLLTLSPVIIYYEQKKRGLRRNRTAITTTPLPEASGAWPVIGHLLLFMN
ENDLNHVTLGHMADKYGPIFSLRFGRHRTLVVSSWEMVKECFTGTNDKLFSNRPSSLAVKLMFYDTESYGFAPYG
KYWRELRKISTHKLLSNQQLEKFKHLRISEVDNSFKKLHELCSNNKQGGDTTYVASLVRMDDWFAYLTFNVIGRI
VSGFQSNAVAGATNSQEKYKLAIDEVSNLMATFAVSDVVPRLGWIDRLTGLTGKMKNCGKKLDAVVGDAVEDHRQ
KKLKISRNNTGALTEHEEEDFIDVCLSIMEQSQIPGNHPEISVKSIALDMLSGGSDTTKLIMIWILSLLLNHPDI
LDKAKEEVDTYFGKKKISDNTPVVDAADVPNLVYIQAIIKESMRLYPASTLMERMTSDDCDVGGFHVPAGTRLWV
NVWKMQRDPRVWKDPLVFLPERFLSNDKGMVDVKGQNYELIPFGTGRRICPGASFALEVLHLVLTRLILEFEMKA
PEGKIDMRARPGFFHNKVVPLDVQLTPRTLD.

Figure 7L

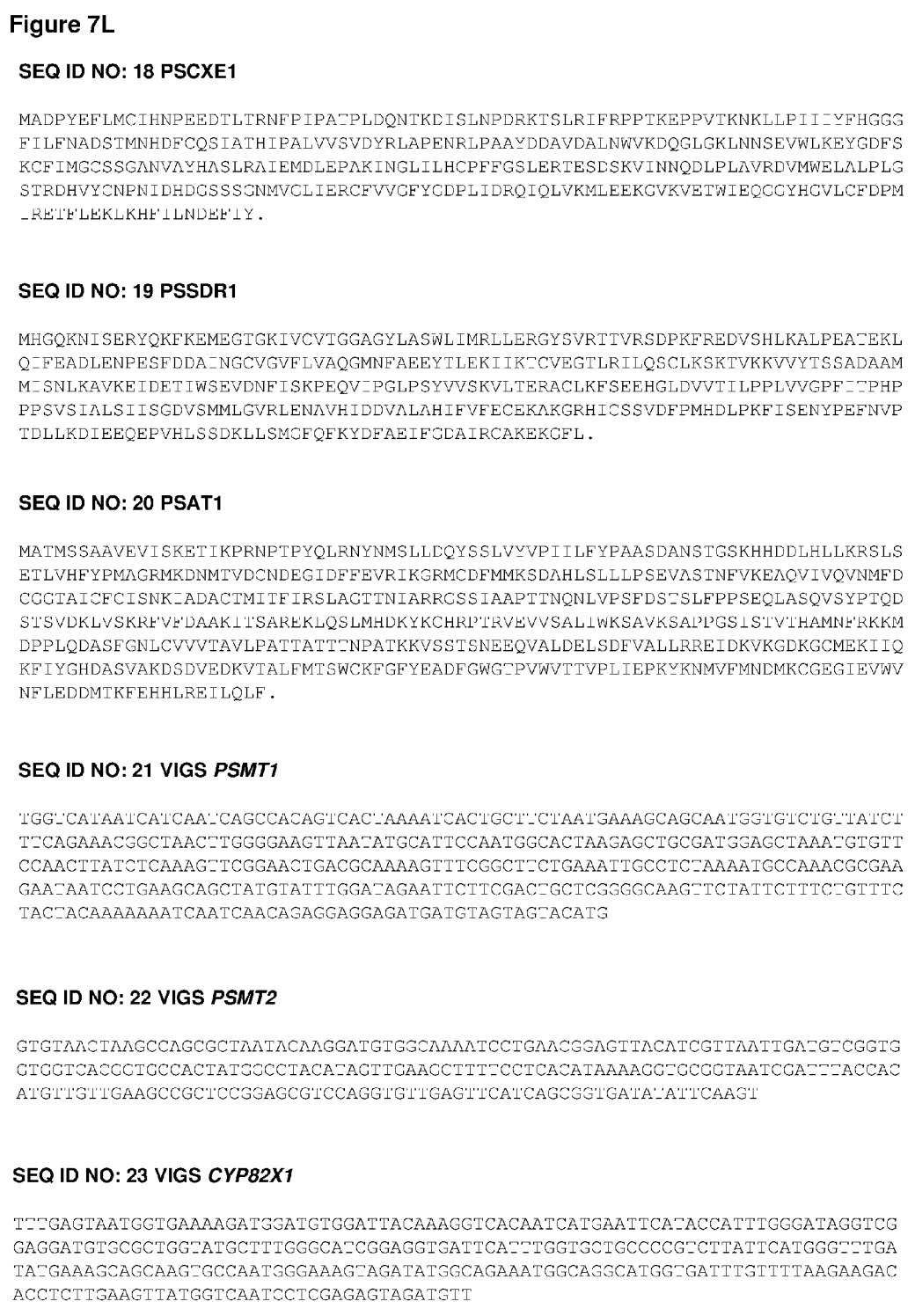

SEQ ID NO: 18 PSCXE1

MADPYEFLMCIHNPEEDTLTRNFPIPATPLDQNTKDISLNPDRKTSLRIFRPPTKEPPVTKNKLLPIIIIYFHGGG
FILFNADSTMNHDFCQSIATHIPALVVSVDYRLAPENRLPAAYDDAVDALNWVKDQGLGKLNNSEVWLKEYGDFS
KCFIMGCSSGANVAYHASLRAIEMDLEPAKINGLILHCPFFGSLERTESDSKVINNQDLPLAVRDVMWELALPLG
STRDHVYCNPNIDHDGSSSGNMVGLIERCFVVGFYCDPLIDRQIQLVKMLEEKGVKVETWIEQCCYHGVLCFDPM
IRETFLEKLKHFILNDEFIY.

SEQ ID NO: 19 PSSDR1

MHGQKNISERYQKFKEMEGTGKIVCVTGGAGYLASWLIMRLLERGYSVRTTVRSDPKFREDVSHLKALPEATEKL
QIFEADLENPESFDDAINGCVGVFLVAQGMNFAEEYTLEKIIKTCVEGTLRILQSCLKSKTVKKVVYTSSADAAM
MISNLKAVKEIDETIWSEVDNFISKPEQVIPGLPSYVVSKVLTERACLKFSEEHGLDVVTILPPLVVGPFIIPHP
PPSVSIALSIISGDVSMMLGVRLENAVHIDDVALAHIFVFECEKAKGRHICSSVDFPMHDLPKFISENYPEFNVP
TDLLKDIEEQEPVHLSSDKLLSMGFQFKYDFAEIFGDAIRCAKEKGFL.

SEQ ID NO: 20 PSAT1

MATMSSAAVEVISKETIKPRNPTPYQLRNYNMSLLDQYSSLVYVPIILFYPAASDANSTGSKHHDDLHLLKRSLS
ETLVHFYPMAGRMKDNMTVDCNDEGIDFFEVRIKGRMCDFMMKSDAHLSLLLPSEVASTNFVKEAQVIVQVNMFD
CGGTAICFCISNKIADACTMITFIRSLAGTTNIARRGSSIAAPTTNQNLVPSFDSTSLFPPSEQLASQVSYPTQD
STSVDKLVSKRFVFDAAKITSAREKLQSLMHDKYKCHRPTRVEVVSALIWKSAVKSAPPGSISTVTHAMNFRKKM
DPPLQDASFGNLCVVVTAVLPATTATTTNPATKKVSSTSNEEQVALDELSDFVALLRREIDKVKGDKGCMEKIIQ
KFIYGHDASVAKDSDVEDKVTALFMTSWCKFGFYEADFGWGTPVWVTTVPLIEPKYKNMVFMNDMKCGEGIEVWV
NFLEDDMTKFEHHLREILQLF.

**SEQ ID NO: 21 VIGS *PSMT1***

TGGTCATAATCATCAATCAGCCACAGTCACTAAAATCACTGCTTCTAATGAAAGCAGCAATGGTGTCTGTTATCT
TTCAGAAACGGCTAACTTGGGGAAGTTAATATGCATTCCAATGGCACTAAGAGCTGCGATGGAGCTAAATGTGTT
CCAACTTATCTCAAAGTTCGGAACTGACGCAAAAGTTTCGGCTTCTGAAATTGCCTCTAAAATGCCAAACGCGAA
GAATAATCCTGAAGCAGCTATGTATTTGGATAGAATTCTTCGACTGCTCGGGGCAAGTTCTATTCTTTCTGTTTC
TACTACAAAAAAATCAATCAACAGAGGAGGAGATGATGTAGTAGTACATG

**SEQ ID NO: 22 VIGS *PSMT2***

GTGTAACTAAGCCAGCGCTAATACAAGGATGTGGCAAAATCCTGAACGGAGTTACATCGTTAATTGATGTCGGTG
GTGGTCACCGTGCCACTATGGCCTACATAGTTGAACCTTTTCCTCACATAAAAGGTGCGGTAATCGATTTACCAC
ATGTTGTTGAAGCCGCTCCGGAGCGTCCAGGTGTTGAGTTCATCAGCGGTGATATATTCAAGT

**SEQ ID NO: 23 VIGS *CYP82X1***

TTTGAGTAATGGTGAAAAGATGGATGTGGATTACAAAGGTCACAATCATGAATTCATACCATTTGGGATAGGTCG
GAGGATGTGCGCTGGTATGCTTTGGGCATCGGAGGTGATTCATTTGGTGCTGCCCCGTCTTATTCATGGGTTTGA
TATGAAAGCAGCAAGTGCCAATGGGAAAGTAGATATGGCAGAAATGGCAGGCATGGTGATTTGTTTTAAGAAGAC
ACCTCTTGAAGTTATGGTCAATCCTCGAGAGTAGATGTT

Figure 7M

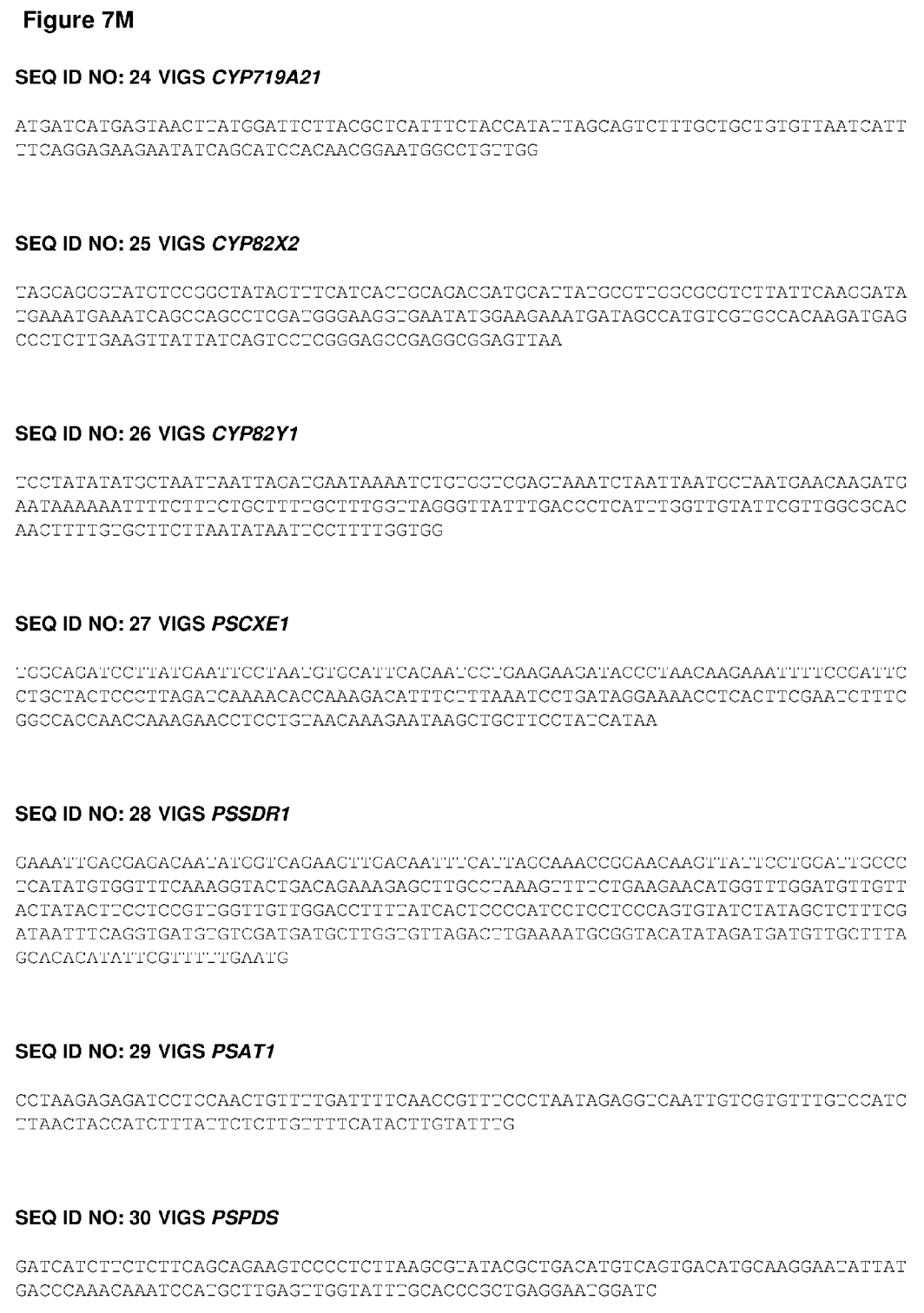

**SEQ ID NO: 24 VIGS *CYP719A21***

ATGATCATGAGTAACTTATGGATTCTTACGCTCATTTCTACCATATTAGCAGTCTTTGCTGCTGTGTTAATCATT
TTCAGGAGAAGAATATCAGCATCCACAACGGAATGGCCTGTTGG

**SEQ ID NO: 25 VIGS *CYP82X2***

TAGCAGCGTATCTCCGGCTATACTTTCATCACTGCAGACGATGCATTATGCCTTCGCGCCTCTTATTCAACGATA
TGAAATGAAATCAGCCAGCCTCGATGGGAAGGTGAATATGGAAGAAATGATAGCCATGTCGTGCCACAAGATGAG
CCCTCTTGAAGTTATTATCAGTCCTCGGGAGCCGAGGCGGAGTTAA

**SEQ ID NO: 26 VIGS *CYP82Y1***

TCCTATATATGCTAATTAATTACATGAATAAAATCTGTCGTCGAGTAAATCTAATTAATCCTAATGAACAAGATG
AATAAAAAATTTTCTTTCTGCTTTTGCTTTGGTTAGGGTTATTTGACCCTCATTTGGTTGTATTCGTTGGCGCAC
AACTTTTGTGCTTCTTAATATAATTCCTTTTGGTGG

**SEQ ID NO: 27 VIGS *PSCXE1***

TGGCAGATCCTTATCAATTCCTAATGTCCATTCACAATCCTGAAGAAGATACCCTAACAAGAAATTTTCCCATTC
CTGCTACTCCCTTAGATCAAAACACCAAAGACATTTCTTTAAATCCTGATAGGAAAACCTCACTTCGAATCTTTC
GGCCACCAACCAAAGAACCTCCTGTAACAAAGAATAAGCTGCTTCCTATCATAA

**SEQ ID NO: 28 VIGS *PSSDR1***

GAAATTCACGACACAATATCGTCAGAACTTCACAATTTCATTACCAAACCGCAACAAGTTATTCCTGCATTGCCC
TCATATGTGGTTTCAAAGGTACTGACAGAAAGAGCTTGCCTAAAGTTTTCTGAAGAACATGGTTTGGATGTTGTT
ACTATACTTCCTCCGTTGGTTGTTGGACCTTTTATCACTCCCCATCCTCCTCCCAGTGTATCTATAGCTCTTTCG
ATAATTTCAGGTGATGTGTCGATGATGCTTGGTGTTAGACTTGAAAATGCGGTACATATAGATGATGTTGCTTTA
GCACACATATTCGTTTTTGAATG

**SEQ ID NO: 29 VIGS *PSAT1***

CCTAAGAGAGATCCTCCAACTGTTTTGATTTTCAACCGTTTCCCTAATAGAGGTCAATTGTCGTGTTTGTCCATC
TTAACTACCATCTTTATTCTCTTGTTTTCATACTTGTATTTG

**SEQ ID NO: 30 VIGS *PSPDS***

GATCATCTTCTCTTCAGCAGAAGTCCCCTCTTAAGCGTATACGCTGACATGTCAGTGACATGCAAGGAATATTAT
GACCCAAACAAATCCATGCTTGAGTTGGTATTTGCACCCGCTGAGGAATGGATC

SEQUENCE LISTING

```
<160> NUMBER OF SEQ ID NOS: 194

<210> SEQ ID NO 1
<211> LENGTH: 2306
<212> TYPE: DNA
<213> ORGANISM: Papaver somniferum

<400> SEQUENCE: 1

cacaccaaac ttgatcattg tcataaaaaa cagtcctaat tgtcatcaat caaaaacagt      60

cctaacatgg ctaccaatgg cgaaattttc aatacctatg gtcataatca tcaatcagcc     120

acagtcacta aaatcactgc ttctaatgaa agcagcaatg gtgtctgtta tctttcagaa     180

acggctaact tggggaagtt aatatgcatt ccaatggcac taagagctgc gatggagcta     240

aatgtgttcc aacttatctc aaagttcgga actgacgcaa aagtttcggc ttctgaaatt     300

gcctctaaaa tgccaaacgc gaagaataat cctgaagcag ctatgtattt ggatagaatt     360

cttcgactgc tcggggcaag ttctattctt tctgtttcta ctacaaaaaa atcaatcaac     420

agaggaggag atgatgtagt agtacatgag aagctttatg ggttaacaaa ttcgtcgtgt     480

tgtttggtcc ctcgacaaga agacggggtg tcattagtcg aagaattgct attcacatct     540

gacaaggttg ttgtggatag ttttttcaaa ctgaaatgtg tggtggaaga aaaagacagt     600

gtgccatttg aggttgctca tggtgctaaa atctttgagt atgctgctac agaaccaaga     660

atgaatcaag tatttaacga tggaatggca gttttctcta ttgttgtttt tgaggctgtt     720

tttagagttt acgatggatt tcttgatatg aaagaattgt tagatgttgg tggtggtatt     780

ggtacttcgg ttagtaagat tgttgctaaa taccctttga ttcgcggtgt caacttcgac     840

ttgcctcatg ttatttctgt tgcccctcaa tacccaggta taccttcttc ttcttttttc     900

tgaaaagaac gggttcgaat ttttacagaa ttttttttct cattcgatac tcaagcaact     960

ctattaaagt atactgtgta ataatgcatg caggtgtaga gcatgttgca ggagatatgt    1020

tcgaggaagt cccaaagggt caaaacatgt tgctaaaagt aagctaacca tactcaattt    1080

tcttaataat taggaaaatt gcaaaaaccg tcacaatatt ataaaggcat ctgaagtgcc    1140

atcactcaga taccgatgct atgtactcta tacattgaca aaattccatg gtatcaagtc    1200

tcaacctgcc ggttataata atttttttca ggctttcttt aaaagaaatt attttgaatg    1260

gtaaaaatca tcattatatt ggagaaaagt gcagatcttg ctacattaaa atttataata    1320

taataaaaca tttgtttatg gttgtttgaa aaaaaaaatc tcattgttaa tgcatctttc    1380

taagttaatg gtgattaatg gtgaataata tgatatctta ttaccgtctt gacacttttt    1440
```

-continued

```
tttttgtcgt agacaaaata tttccaactt ttctatatta ataaaatcag aaatatttca   1500
tttatatgaa tattaaaata agaaggtgca tgagtaatat tccaaatttc ttaaagcgtt   1560
ttttatagca gtacggcgtt ttctcaaatc ttattaaccc ataattaaag ggtttccgta   1620
aattaaattg agggatatca aaacaaaaac aaaaaatagg gttattttgc agtaaaatca   1680
ataacccctt atcatatgaa aaggataact tagtctaccc caatttggag agatatgggc   1740
aattattgta ttactagttc gtttgagcat tgataatatt tttcattaga tttatactca   1800
ataaaatata tgaactatat tgataaagat taataatgca gtgggtactg cacgattggg   1860
gtgatgaacg atgtgtgaag ctgttaaaga attgttggaa ctcattacct gtgggtggaa   1920
aagttttgat aatcgagttt gttctcccga atgaacttgg taacaatgct gaatcattca   1980
atgcgttgat tcccgattta ctcctgatgg ctctgaatcc aggcggtaaa gagcgaacga   2040
tttccgaata cgatgattta ggcaaagcag ctggattcat aaaaactata cctatcccta   2100
tctccaatgg tcttcatgtc attgagtttc acaaatgaat ggttattgag tgctttggta   2160
attaaactac caagataact acatccattt catgcatttg cttttttttt ttcttttttt   2220
tctttttttt tctttttgtt ttgtattcca ggtgtgaact agttagtgtg ttgagtggac   2280
aaaagtaagt aatcgtattt tgtgtt                                        2306
```

<210> SEQ ID NO 2
<211> LENGTH: 1440
<212> TYPE: DNA
<213> ORGANISM: Papaver somniferum

<400> SEQUENCE: 2

```
gaatcagaaa ctttcttcta aaatctttca ataccagtac tgttagtttc cgataagagc     60
cacactaatc cattatggaa attcatttag aaagccaaga acaagaaatg aaatatcaat    120
ctcaaatctg gaaccaaata tgtggcactg ttgatacctc tgttctgaga tgtgcaattc    180
aattaggtat atttgatgcc attcataact ctggcaaacc aatgattacc ttaaccgaat    240
tatcaagcat tgtttcatca ccctcttcat cttcaatcga accctgcaac ttgtatagat    300
tagtgagata cttatcccaa atggatctca ttagtatcgg agaatgtttg aatgaagcaa    360
ctgtttcatt aacaggcaca tccaagttac tacttagaaa ccaagaaaag agtttaattg    420
attgggtatt ggcaatttct tgcgaaatga tggttgttgt ttggcacgaa ctaagtagct    480
ctgtttcaac tcctgcggat gagcctccaa tcttccagaa ggttcatggt aaaaatgctt    540
tagaattagc aggggaattt ccagaatgga atgatctgat caacaatgct atgactagtg    600
atactagtgt aactaagcca gcgctaatac aaggatgtgg caaaatcctg aacggagtta    660
catcgttaat tgatgtcggt ggtggtcacg gtgccactat ggcctacata gttgaagctt    720
ttcctcacat aaaaggtgcg gtaatcgatt taccacatgt tgttgaagcc gctccggagc    780
gtccaggtgt tgagttcatc agcggtgata tattcaagtc catttctaac gctgatgctg    840
tgttgttgaa ggtatgtaaa gagtagctaa ccttagtgcg tctaatttat tccacaaatt    900
tttctgatgc attttattct tatttttggt ttttgcagta tgtcctgcac aattgggaag    960
atacggaatg tgtgaattta ctgaagagat gtaaggaagc agttccggca gacaaaggaa   1020
aagtgatcat aatggattta gtaatagacg acgatgataa cagtatttta acgcaggcaa   1080
agttgagcct tgatctcact gtgatgaacc atggaggagg tagagaaagg actaaagaag   1140
attggagaaa tctaattgag atgtctggat ttagtaggca tgaaataatt ccaatatctg   1200
```

-continued ccatgccatc aattattgtt gcttatcctt agttaagtca cccgcatgtt tacttgaacg 1260
ggaataagtt gggggcgtgt tgaatctgtt aacatcgcaa ttgtgccttt actttatgca 1320
ttctcattcc ggtagaaact gtttggggca ttcggattct gctgagccct tttatgtatg 1380
tttgtttgtt ggttggttgg ttttcaagta actgaagttt cttctctgtt ttcaaggcat 1440

<210> SEQ ID NO 3
<211> LENGTH: 1436
<212> TYPE: DNA
<213> ORGANISM: Papaver somniferum

<400> SEQUENCE: 3
aagttgcagg tagggttatg agcaagctca attatctctc ctataaaagc taacattaga 60
aaaactaata agcacacaaa ccgtaaaagt tctgaagata gacaaaacaa gagaaaaaag 120
atggaagtag taagtaagat tgatcaagaa aaccaagcaa aaatttggaa acaaattttt 180
ggttttgcag aatcattagt tctaaaatgt gcagttcagt tagagattgc tgaaacactt 240
cataataatg taaaacccat gtctttatcc gagttagcat ctaaacttcc ggctcaaccc 300
gttaatgaag accgtttgta ccgaattctg catttcttag ttcacatgaa actcttcaac 360
aaagatgcta ccacacagaa atattcatta gctccaccag caaagtattt gctaaaaggc 420
tgggaaaaat caatggttcc ttcaatatta agcgtgactg ataaagattt tacagctcca 480
tggaatcatc ttggggacgg tttaaccggt aactgtaacg cttttgagaa agcgttagga 540
aagggcattc gggtttatat gagagaaaat cctgaaaaag atcaattgtt taatgaagga 600
atggcttgtg atactagatt atttgcttca gcattggtta acgagtgcaa aagtattttc 660
agtgacggga tcaatacact tgccggtgtt ggccgtggta ctggtactgc agtgaaagcc 720
atatccaaag cttttccgga tattaagtgc acaatccatg atcttcctga agttaccagt 780
aaaaatagta aaattccaag agatgttttt aagtccgttc ctagtgcaga cgccatcttt 840
atgaaggtaa cttctaagaa attttgtttt agaatattcg ttgcaactct aattgacaac 900
attcataaaa aatatgttaa tggtcttaat ttattaattc tagtagagtt acttaaatga 960
tatacaaaaa ttcaaaatca tataacattt gcagagcatt cttcacgaat ggaacgatga 1020
ggaatgtatt caaatcttga aacgatgcaa agaagcaata ccaaaagggg gcaaagttat 1080
cattgcggat gtcgtaatag acatggactc gactcatccg tattcaaaat ctagactcgc 1140
aatggatttg gctatgatgc tccacacggg tggaaaagag agaactgaag aagattggaa 1200
aaaacttatt gatgctgcag gttttgctag ctgtaaaatt actaaactat ctgctctcca 1260
gtctgttatt gaggcttacc ctcattgagg ataattttta tccttctgtt ttccctttgg 1320
ttaattgttg ccttctcttt ggatcatggt tgcgtttata ataaatgcag cgtttctttc 1380
ctggcggtaa gtgcaagaaa gaaaaagctt ccagaaactt ccttgagtat gcctgg 1436

<210> SEQ ID NO 4
<211> LENGTH: 1921
<212> TYPE: DNA
<213> ORGANISM: Papaver somniferum

<400> SEQUENCE: 4
cttgagtcat gccttgatat gctcatattt tagtttgtca tattcactat aactataaat 60
ttcaatacaa tttctaaaac tcatcatcat tcaagagaga tacaaatacc ttgatatcct 120
tttatcatca atggagttat tcataaagtt accatttatc caaccaattc ctttcagtat 180
tattcttgtt actacagttt cgattgttct attatacagt gtcttcttct gggttactga 240

-continued

```
taagaaaaag aagaggaaga aagcaccaaa tgctgcaggg gcatggccgt taataggtca    300

tctccgtcta ttgatgaacg acaaggaacc gttgtataga gcactaggga gcatggctga    360

taagtacgga cctgcattca acatccgatt aggtaaccaa gaagttcttg ttgtgagtaa    420

ctgggagatg gtaaaacagt gttttggtaa tcaaaatgat aagctatttt cgaatcgtca    480

aactacatta gctgcaaaat acatgcttaa tcaaacaact tctagcggat tcgcaccata    540

tggaccatat tggagagagc tacgaaagat aatggtgcag caattactct ctaaacaatc    600

tttagaatcg tggaaacatc tgaaaatcaa agagatggat gcttcattta gtaaacttaa    660

cgagttatgc aacaacaacg gtactggaac agctacccta attaggatgg acgaatggtt    720

tgctgagttg acgttcaacg tgatcgcaag aaatgtcttt ggctaccaaa gtggcggaag    780

gtcgacagcg cttacgaacg gtaatatgat catactccct caatctgtat caatttaagg    840

aaatcatttt ggtcttgtta ttaacttgaa ttttctatta ggagatacgg aatcaaaggg    900

cgagaggtac aagaaaacat tggaagaagc acttcatctt atgtcaattt ttgcagtttc    960

agacatattt ccaagtctag agtgggtaga tcggttaaga ggccttataa ggaatatgaa   1020

acgctttgga gatgagctaa attcaattgc agggtgtctt attgaagagc accgccaaaa   1080

gagattacaa tccgtatcta aaagtgataa aggagttggt gatgaacaag acttcgttga   1140

tgttctctta tcggttgctg aaaaatcgca acttcctgga gatgaccctg atttggtcat   1200

caagtctatg attctggtta ggctattgat accaagtcta ttgcaatttt ggtttatgtg   1260

cttgttctaa ctttcgttta ctgcatatgg atgtgcagga aatcgtatca ggtgggagtg   1320

agaccacatc gtcaacctta acttgggccc tctgtctgtt actgaaccat ccgcatgtgt   1380

taaagaaggc aaaagaggaa ttagatacgc acgtaggaaa agataggcat gtagaagagt   1440

cagatacccc taagctcgtg tacattaatg caattatcaa agaatcaatg cgattgtatc   1500

caaacggggc aatgcttgat cggttggcgt tagaagagtg cgaagttggt ggatttcatg   1560

taccggccgg gggacgctta tttgtcaatg tttggaagat tcagagagat ccgagtgttt   1620

gggagaatcc tctggagttt aaaccagaga ggtggttttt gagtaatggt gaaaagatgg   1680

atgtggatta caaaggtcac aatcatgaat tcataccatt tgggataggt cggaggatgt   1740

gcgctggtat gctttgggca tcggaggtga ttcatttggt gctgccccgt cttattcatg   1800

ggtttgatat gaaagcagca agtgccaatg ggaaagtaga tatggcagaa atggcaggca   1860

tggtgatttg ttttaagaag acacctcttg aagttatggt caatcctcga gagtagatgt   1920

t                                                                   1921
```

<210> SEQ ID NO 5
<211> LENGTH: 1688
<212> TYPE: DNA
<213> ORGANISM: Papaver somniferum

<400> SEQUENCE: 5

```
catgaaattc tttatgcaaa gagtcaatct gactcaagct agctagaata tataccaatc     60

ataaaagaaa tgatcatgag taacttatgg attcttacgc tcatttctac catattagca    120

gtctttgctg ctgtgttaat cattttcagg agaagaatat cagcatccac aacggaatgg    180

cctgttggcc caaaaacatt accaatcata ggtaacttgc acattcttgg aggcactgct    240

ctccatgtcg tcttacataa acttgctgaa gtttacggca gtgtaatgac gatatggatt    300

ggtagttgga aacctgttat tattgtttcc gactttgatc gagcctggga agttcttgtt    360
```

-continued

```
aacaaatcgt cagattattc agctcgtgaa atgcctgaga tcactaaaat cggcactgca    420

aattggagaa caatttcaag ttctgattct ggtccgtttt gggccactct tcgaaaaggt    480

cttcagagtg tagcattatc gcctcagcat ttagcatcgc aaactgcaca ccaagagaga    540

gatataataa agttgatcaa aaatttgaaa gacgaagcag cttctggaat ggttaaacca    600

cttgatcatc tcaagaaagc aactgtaaga ttaatcagtc ggttaatcta tggtcaggat    660

tttgatgacg ataagtatgt tgaagatatg catgacgtga tcgagttttt gattcgtatt    720

agtggttatg ctcaacttgc tgaggtattc tattatgcta aatatctacc aggtcataag    780

agagctgtaa ctggcgccga agaagcaaaa agaagagtaa tagctctggt gcgtcctttt    840

cttcagtcaa accctgctac taacacttac ttgcattttc tcaaatcgca actgtatcct    900

gaagaggtta tcatattcgc tatattcgaa gcttatcttt taggtgttga tagcacttct    960

tcaaccactg catgggcact cgcattctta atacgcgaac catctgttca agagaaactt   1020

tatcaagagc ttaagaattt cacagccaat aacaatcgca caatgctgaa agtcgaagac   1080

gtcaacaaat taccatattt acaagctgtt gttaaagaaa caatgaggat gaaaccaatt   1140

gcaccactgg cgattcctca taaagcttgt aaagacactt cattgatggg caagaaagtt   1200

gataagggaa ctaaagttat ggttaacatt catgctttac atcatactga aaaggtttgg   1260

aaagaacctt acaaattcat accagagagg tttctgcaga agcacgataa ggcgatggaa   1320

caatcactat taccatttag tgcaggtatg agaatttgtg caggaatgga attaggaaaa   1380

cttcagttta gtttttctct tgctaatctt gttaatgctt ttaaatggtc ttgtgtgtct   1440

gatggagtgc ttcctgatat gagtgattta ctggggtttg ttctgttcat gaaaacccca   1500

ctcgaagcac gtatagttcc tcgtttgtag tgatggaaat ttcatctcat gttgttgttt   1560

ctcttcatgt ttactatttc gtactcgttt ggttttggtg taaaaaataa gatctaaact   1620

tccaaatatc attaatgttt acacaaatcg aaatcaatca actatgttat gaaaattagt   1680

gttttctc                                                            1688
```

<210> SEQ ID NO 6
<211> LENGTH: 2918
<212> TYPE: DNA
<213> ORGANISM: Papaver somniferum

<400> SEQUENCE: 6

```
aagtgtgcca ctaatctact gctagtgcta ctgctcactg acacttacac atatgattga     60

tttatggcta aacaggatga ccactaaatt tattttggaa agcggagtga attaattaag    120

tggcacattt tccatgagaa ttattgatgg catgcattta gatgaacaag atacaccaaa    180

tgtagtgact gaacaagatg ctcgatccta accccacctg caactttagc taaactttaa    240

taattacatg tcttatcttt ttattgaatc attttatcta tcaatggatg ctgatcaata    300

atatcatata tctttgcttt ttcttcaatc atttagatga acaaaaaaca caataagtgt    360

agtggttgtt cataacccca ccttcaactc attcttccct ttaataacaa atatctttgc    420

tttttctcca atcatttact tgaacaacca acactagtaa gtgtagtggt ttctcataac    480

cccacctgca atttttgctt acctttaata acatatatct ttgattttct tcgatcattt    540

tagctaccaa tggatgctga tccaaaaagt tatggcaaaa agagacaacg tgatcgaaca    600

cgagcctctc gtgcaccaca gcatcaaggt ttgtggaaat taaccgcttg taaaaaatgg    660

agtgcgtgat cataatgagg tattgctaag atatagtatc aactttagtg aactgggcca    720

acaaaactca cgagttgttg aaaattggag attatattta taagataaaa gggtcactcc    780
```

-continued

```
ctacacaacg acttgcactg caagtgaaaa agaaaaaaaa caaacaacct caatctagct    840
agagtcgtga aaaagttttg tgcgactgtt atttagttaa ttataaaatt tcaatgaagt    900
cgttaatgat gaacaagtta ttatttctcc aacggattac tgattctcct tcgaccacca    960
ttatcagtac ttttattgtt acaataatat ccattgtttt tctctacact gtcttgttga   1020
taaggacgac taagaataag cagaagatag cagcaccaaa agcatcgggg gcgtggccgt   1080
tcataggtca tctcaaacta ttcatgaaac aagatactca gttttacaga actctaggaa   1140
ccatgtctga taaatacggg tcggtgttca cacttcgatt aggaaaccaa gcaatcctag   1200
ttgtgagcaa ctgggagatg gtaaaagaat gtttcacaac aaacgacaag tcattctcga   1260
atcgtccaag tacgttaagc actaaataca tgctgaatga cactaattct gtcgtgtttt   1320
caccttacgg aacgtattgg agagaaatgc ggaagatatt ggtgcaaaaa ctactgatct   1380
ctaaccaaag atcagaggca ttgaaaaatc tgaaaacgaa agaaatcgac aactcgtttg   1440
taaagcttaa tgatttatgc aacaacgatg tcagtggagg aggcacaaaa gttaggatgg   1500
acgaatggtt ggctgacatg atgttcaaca ttattgctag gattacattt ggttaccaaa   1560
gcggaggagg cgatgcacct ggtatgtgat catcaaattt tcgttaaaac caaattaact   1620
tgtactatat cttatgttta catgttatat tgatcacttt gacacgttct gatcattttc   1680
acaaatcgaa ttaggcgctt ctacaacatc caagaatgtc gagagataca agaaaacgtt   1740
ggacgagatg tttgttgttt tagcgacgag gtttgcagtt tcagatatat ttccatctct   1800
ggagtttata gaccgattga gaggtcttgt aaaggatatg aaaatcttgg gagacgaatt   1860
aaactccatt gctggatgtt ttattgaaga acatcgtcaa aagagacgag aatcattatc   1920
ctcattgtta tctttgtcaa atgaatccgt tggtgatgaa caagatttca ttgatgttct   1980
cttgtcaata atggatcagt cacggcttcc cggagatgac ccagatttta ttatcaaaat   2040
tatgatcctg gtaacatata ttacaacagt atttctttaa gttatggatt aatggatgtc   2100
gtaaccatga atatttttct gatctggata aatgtaatcc ggaactaata tatgaatatt   2160
gttgacgcag gaagcttttg caggtgggac ggacagttta agtgcaacct taacttgggt   2220
cctctctcta ctgctgaacc acccaaacgt gttaaagagg gcaagggagg aaatagatag   2280
gcatgtggaa aacggtaagc aagtggaagt gtctgatatt ccgaagctcg gatacattga   2340
tgcaataatc aaagagacga tgagattgta tccagtcgga gcattaagcg aacgatacac   2400
gactgaagaa tgcgaggttg gtcggtttaa cgtacccgct ggcacacgct tactggtgaa   2460
tatatggaag atccacagag acccaagtgt gtgggagaat ccatcagatt ttcaaccaga   2520
gaggtttttg tgcagcgata aggtgggtgt ggatttatat ggccagaatt atgagctgat   2580
accatttggg gccggtagga gggtatgtcc ggctatagtt tcatcactgc agacgatgca   2640
ttatgcgttg gcgcgtctta ttcaaggata tgaaatgaaa tcagccagcc tcgatgggaa   2700
ggtgaatatg gaagaaatga tagccatgtc gtgccacaag atgagccctc ttgaagttat   2760
tatcagtcct cgggagccga ggcggagtta aatcttatgt tccaatttta cattagcatc   2820
tttgattatg aaatgtattg ctcttaagtt tcttttttgt tttttatatt tttaagcttg   2880
tatgtgatca tcagcgaaaa tgatgatgac agaatcgt                            2918
```

<210> SEQ ID NO 7
<211> LENGTH: 1915
<212> TYPE: DNA
<213> ORGANISM: Papaver somniferum -continued

<400> SEQUENCE: 7
ttcagttcat tcatggcgta tttgatgatc aagaagtcta tctatttgtt ttttgatcaa 60
ccaactgcag ttggcactct tatacttgct tttctgctga cactttcgcc tgttattatt 120
tactatgaac agaagaagag gggtttgagg cgaaatcgca ccgcaattac aacgactcca 180
ttaccagagg catcaggtgc atggccagtg ataggtcatc ttcttctttt catgaacgaa 240
aacgatctaa atcatgtaac tcttggtcac atggctgata aatatggacc tattttcagc 300
ttaagattcg gtagacatag aactctagtt gttagtagtt gggagatggt aaaggagtgt 360
tttacaggta ccaatgacaa gttgttctca aatcgtcctt cctccttggc ggttaaactt 420
atgttttatg acactgaatc ttatggtttt gcaccttatg ggaaatactg gagagagttg 480
cgaaagatat ctacacacaa actcctctct aatcagcaat tagagaagtt caagcacttg 540
cggatttctg aagtcgataa ctcctttaaa aagcttcatg agttatgcag caacaacaaa 600
cagggaggtg atactacata tgtggctagt cttgtgagaa tggatgattg gttcgcgtac 660
ttgacattta acgtaatagg acggatcgtc agcggattcc aatcaaatgc agtggcaggt 720
gagctcatat agctaggttt ttatatgttt ggtttgtaca cacacagctc attcatattc 780
taaactgaat tatatgttat aattgaacaa cataggtgcc acaaacagcc aggaaaaata 840
caagcttgca atcgatgaag tgtcaaatct tatggcaacg tttgccgttt cagatgtggt 900
tccacggctt gggtggattg atcgattgac tggtcttaca ggaaagatga agaattgtgg 960
taaaaaatta gatgcagtag ttggggatgc agtggaggat catcgccaaa agaaactcaa 1020
aatttctaga aataacacag gagcacttac ggagcacgaa gaagaagact ttatcgatgt 1080
ttgcttgtcg attatggagc agtcacagat tccgggaaac caccccgaaa tctctgtcaa 1140
atctattgcc ttggtaatac gtctcataag catgttagca gattttacct ctatatatac 1200
ttacatatta ttttttatca atcacacata tgtgcaggac atgttatcgg gtgggagtga 1260
cactacaaaa ttgataatga catggaccct ttctttgctg ttgaaccatc cagacatatt 1320
ggacaaggct aaagaagaag tagatacata cttcgggaag aaaaagatat cggataacac 1380
acctgtggtt gatgctgccg atgttcctaa cctcgtctac atccaagcaa tcatcaaaga 1440
atcaatgcgg ttataccctg ctagcacatt gatggagcga atgacaagtg atgattgtga 1500
tgttggtggc ttccacgtac cagctgggac acgattatgg gttaacgtat ggaagatgca 1560
acgggaccca agggtgtgga aagatccact ggtatttcta cctgagagat tcttgagcaa 1620
tgacaaaggg atggtagatg tgaagggtca gaattatgaa ctgataccat ttggaacagg 1680
caggcggata tgtcctggtg catcttttgc cttggaagtc ttgcatttgg ttcttactcg 1740
tcttattctt gagttcgaga tgaaggcacc agaggggaaa attgacatga gggcaagacc 1800 aggtttttc cacaacaagg tggtgccact agatgttcaa ctcaccccac gcacactaga 1860
ttaagattcc tatatatgct aattaattag atgaataaaa tctgtggtcg agtaa 1915

<210> SEQ ID NO 8
<211> LENGTH: 1133
<212> TYPE: DNA
<213> ORGANISM: Papaver somniferum

<400> SEQUENCE: 8
aataaaaatc caacaatggc agatccttat gaattcctaa tgtgcattca caatcctgaa 60
gaagataccc taacaagaaa ttttccgatt cctgctactc ccttagatca aaacaccaaa 120
gacatttctt taaatcctga taggaaaacc tcacttcgaa tctttcggcc accaaccaaa 180

-continued

```
gaacctcctg taacaaagaa taagctgctt cctatcataa tttatttcca tggtggaggt    240
ttcattcttt tcaatgcaga ttcaactatg aaccatgact tttgtcaatc gattgctaca    300
catatacccg cgctggtcgt ttctgtagac taccgtcttg ctcctgaaaa ccgacttccc    360
gctgcctatg atgatgctgt tgatgcttta aactgggtca aagaccaagg tttaggcaaa    420
ctaaataata gtgaagtatg gttaaaagag tatggtgact tctcaaagtg tttcattatg    480
gggtgcagct caggtgctaa tgttgcatat catgccagtt taagagcaat agaaatggat    540
cttgaaccag ctaagattaa tggattaata ttacactgcc ctttttttgg tagtcttgag    600
agaactgaat cagattcaaa agtgatcaac aatcaggact tgccgcttgc cgtaagggat    660
gtcatgtggg aactggcgtt gccgcttggg tctactcgtg atcacgttta ttgtaatccg    720
aatattgatc atgatggatc atcatctgga aatatggtgg ggttaatcga gagatgtttt    780
gtggtaggat tttatgggga tccacttatt gatcgacaaa ttcagctggt gaagatgctg    840
gaggaaaaag gtgtgaaggt tgaaacttgg attgaacaag gagggtatca tggggtgcta    900
tgctttgacc ctatgatacg tgaaaccttt ttggaaaaac taaaacattt tattttaaac    960
gacgaattta tatactaaaa tatattatta gtattaaaca atgaaattct tatttttttct   1020
aaaatgagct tttggacgaa acattgtgta cgaactagct gatgtaattt ttcgttttac   1080
cggatttttc atttttttttg ctttctttct gctctctttt ataagtcgtt ctt          1133
```

<210> SEQ ID NO 9
<211> LENGTH: 2488
<212> TYPE: DNA
<213> ORGANISM: Papaver somniferum

<400> SEQUENCE: 9

```
ctaacaggca aacaataaca ggttgcacct acaacattca atttttattt tggtaaatga     60
agttcagttg gagagtaacc acatctttgt tgtcggcatt gcccccacaa tactgagtgt    120
tttggctgag tgtagtctga ctgtaggtaa gctacaactg catgttgcag ataataatca    180
ctaactgatt attcatgcat acctaacagt catattgtta tagttcccaa aaaaaattct    240
cgaactataa aggcatgcat ggacagaaaa atatatcaga gagatatcag aaattcaaag    300
agatggaagg aacagggaag atagtatgtg taacaggtgg agctggatac ttggcatctt    360
ggctgatcat gagattgctt gaacgtggtt actctgttcg gaccaccgtt cggtctgacc    420
caagtacgta ataaattaaa tttcctggca tcattttctt caatataaat ttcttattat    480
ctagttcatc attctttatt gttccaatca tgtcccccca agtctaaaag aagtagtaat    540
ctaaaaatag ctaatttatg tacgaaattg taacaatgat ctcctagctt atgaggctca    600
cctaatttcg tttctatcat tttgtgtctt gaaagaattt agggaagatg tgagccacct    660
taaagctctt cctgaagcta cagagaagct tcaaattttt gaagcagatc ttgaaaaccc    720
agaaagtttc gacgatgcga tcaacggttg tgtcggtgtc tttctcgttg ctcaaggaat    780
gaattttgcc gaagaatata ctcttgaaaa aataatcaaa acatgcgtgg aaggaactct    840
tagaattcta cagtcatgct tgaaatctaa aacagtgaaa aaggttgtgt acacatcttc    900
tgctgatgca gcaatgatga taagtaatct caaagctgtt aaagaaattg acgagacaat    960
atggtcagaa gttgacaatt tcattagcaa accggaacaa gttattcctg gattgccctc   1020
atatgtggtt tcaaaggtac tgacagaaag agcttgccta aagttttctg aagaacatgg   1080
tttggatgtt gttactatac ttcctccgtt ggttgttgga ccttttatca ctccccatcc   1140
```

-continued

```
tcctcccagt gtatctatag ctctttcgat aatttcaggt atcctctcca tccgaaaaat   1200

atgccaattc ctaaacttaa aaggcatatt gatatttaat aatacctcca tacctaaaaa   1260

aagagttgct atataacatt tttaattttc gcccattttt aggcctaatt gaaaaagtta   1320

taataacatt ttaggaagga gggagaatga tttttgagca aaccttagaa ctgtgtggtg   1380

agatttgtcc gttatcattg ttggtataac tgtgtatatc atggttttta aaagcgccgc   1440

tcacgctacg cttcgtacgg ttcggtctag atttttttaa ttcgctccga agcgtagtta   1500

tgaagctacc atgaagcgcc gcttcacgct acgtttcgta cgcttcgctt cagatttttc   1560

aaattcgctc cgaggcgaat ctaccatgaa gtggaagatt cctttaattg attcactttt   1620

ttacttagtc aagtcttttt tagggggttt cgaaaactaa agtgaaccac tgcgcctcgc   1680

tactgttttt gaaattaact agacttatat taaattgata caattattat atcttcctaa   1740

atattaaatt attaataaca aactactact atttatagga aaaaattcgc ttcaaatatc   1800

aatcataaaa cgacgcttca catttcaaca tgcgcatcgc ttcgtataaa aaaaaaacgc   1860

ttcacgcttt caataccttg gtgtacatag attaatactt cctcctctgc gctggtgtta   1920

acatttctgt gtttcgttta tatatatgac caggtgatgt gtcgatgatg cttggtgtta   1980

gacttgaaaa tgcggtacat atagatgatg ttgctttagc acacatattc gtttttgaat   2040

gtgaaaaagc aaaaggaaga catatttgtt cttcagttga ttttccaatg catgatctgc   2100

ctaaatttat atctgagaat tatccggaat tcaacgtacc gactgagtga gtttatcttt   2160

caccaccttc tttattatta ttcatcaagt cactttgggt attttaacct tattgttttt   2220

actgaattat catcagttta ctaaaggata ttgaggaaca agaaccagtt catctttcct   2280

cagataagct gttgagtatg ggatttcagt tcaaatatga ttttgcagag attttcggtg   2340

atgcaatacg atgtgccaaa gagaagggtt tcctttagag accaactata gtttggttcg   2400

gaggagatgt gggagtagct agcccaaaat gccctgctcg cactagctta tattattgtt   2460

attgtttttc aaatgaataa acgggcag                                      2488


<210> SEQ ID NO 10
<211> LENGTH: 1572
<212> TYPE: DNA
<213> ORGANISM: Papaver somniferum

<400> SEQUENCE: 10

cgcatataat ccaatttgca ttgtttatcg accttgagga acaattaggg gatatggcaa     60

caatgtctag tgctgctgta gaagtgatct cgaaagaaac gattaaacca agaaatccaa    120

caccatatca acttagaaac tacaatatgt cacttctcga ccaatattct tctctagttt    180

atgttccgat cattcttttc taccctgctg cctccgacgc taatagtacc ggaagtaagc    240

accatgatga tcttcacttg cttaagaggt ctctttctga aacgctagtt cacttttatc    300

caatggctgg taggatgaaa gacaacatga ctgttgactg taacgacgaa ggtattgact    360

ttttcgaagt aagaatcaaa ggtagaatgt gtgacttcat gatgaaatca gatgcacact    420

taagtctgct tcttccgtct gaagtcgctt ccacgaactt cgtgaaggaa gcacaggtga    480

ttgttcaagt gaacatgttt gattgcggtg gaactgccat ttgtttctgt atatcaaaca    540

agattgcaga tgcatgcacc atgattacct tcattcgtag tttggcaggc accaccaaca    600

tagctcgtcg tgggagctct attgctgcac caaccacaaa tcagaatttg gttccttctt    660

tcgattcgac atcactcttt ccacctagtg aacaattggc atctcaagtt tcctatccta    720

cacaggatag taccagcgta gataaacttg tcagcaaaag atttgtgttt gatgcggcaa    780
```

-continued

```
agattacatc tgcacgtgaa aaattgcaat ccttgatgca tgataaatac aaatgccata    840

ggccgacaag ggttgaggta gtttccgctt tgatatggaa gtcagcagtg aaatctgctc    900

cgcccggttc tatatccact gtaacccatg ccatgaactt tagaaagaaa atggatccac    960

cattacaaga tgcgtcattc gggaatcttt gtgtggttgt tacagcagta ttaccagcaa   1020

caacggcgac aacaacaaat ccagcaacca aaaaagttag tagtacgagt aatgaagagc   1080

aagtggcact tgatgagtta agtgattttg tagccctatt gaggcgcgaa atagataagg   1140

taaagggtga taaaggttgc atggagaaaa tcattcaaaa gttcatctat ggtcatgatg   1200

cttccgtagc gaaagacagt gatgttgaag ataaggtgac agctttgttt atgactagct   1260

ggtgcaagtt tggattctac gaagctgatt ttggttgggg aacgccagtt tgggtaacta   1320

ctgttccatt aattgagcca aagtacaaga acatggtttt catgaacgat atgaaatgtg   1380

gtgaaggaat tgaagtgtgg gtgaattttc tggaggatga tatgaccaag ttcgaacacc   1440

acctaagaga gatcctccaa ctgttttgat tttcaaccgt ttccctaata gaggtcaatt   1500

gtcgtgtttg tccatcttaa ctaccatctt tattctcttg ttttcatact tgtatttgtc   1560

ttactccggt aa                                                       1572
```

```
<210> SEQ ID NO 11
<211> LENGTH: 390
<212> TYPE: PRT
<213> ORGANISM: Papaver somniferum

<400> SEQUENCE: 11

Met Ala Thr Asn Gly Glu Ile Phe Asn Thr Tyr Gly His Asn His Gln
1               5                   10                  15

Ser Ala Thr Val Thr Lys Ile Thr Ala Ser Asn Glu Ser Ser Asn Gly
            20                  25                  30

Val Cys Tyr Leu Ser Glu Thr Ala Asn Leu Gly Lys Leu Ile Cys Ile
        35                  40                  45

Pro Met Ala Leu Arg Ala Ala Met Glu Leu Asn Val Phe Gln Leu Ile
    50                  55                  60

Ser Lys Phe Gly Thr Asp Ala Lys Val Ser Ala Ser Glu Ile Ala Ser
65                  70                  75                  80

Lys Met Pro Asn Ala Lys Asn Asn Pro Glu Ala Ala Met Tyr Leu Asp
                85                  90                  95

Arg Ile Leu Arg Leu Leu Gly Ala Ser Ser Ile Leu Ser Val Ser Thr
            100                 105                 110

Thr Lys Lys Ser Ile Asn Arg Gly Gly Asp Asp Val Val Val His Glu
        115                 120                 125

Lys Leu Tyr Gly Leu Thr Asn Ser Ser Cys Cys Leu Val Pro Arg Gln
    130                 135                 140

Glu Asp Gly Val Ser Leu Val Glu Glu Leu Leu Phe Thr Ser Asp Lys
145                 150                 155                 160

Val Val Val Asp Ser Phe Phe Lys Leu Lys Cys Val Val Glu Glu Lys
                165                 170                 175

Asp Ser Val Pro Phe Glu Val Ala His Gly Ala Lys Ile Phe Glu Tyr
            180                 185                 190

Ala Ala Thr Glu Pro Arg Met Asn Gln Val Phe Asn Asp Gly Met Ala
        195                 200                 205

Val Phe Ser Ile Val Val Phe Glu Ala Val Phe Arg Val Tyr Asp Gly
    210                 215                 220
```

-continued

Phe Leu Asp Met Lys Glu Leu Leu Asp Val Gly Gly Gly Ile Gly Thr
225 230 235 240

Ser Val Ser Lys Ile Val Ala Lys Tyr Pro Leu Ile Arg Gly Val Asn
245 250 255

Phe Asp Leu Pro His Val Ile Ser Val Ala Pro Gln Tyr Pro Gly Val
260 265 270

Glu His Val Ala Gly Asp Met Phe Glu Glu Val Pro Lys Gly Gln Asn
275 280 285

Met Leu Leu Lys Trp Val Leu His Asp Trp Gly Asp Glu Arg Cys Val
290 295 300

Lys Leu Leu Lys Asn Cys Trp Asn Ser Leu Pro Val Gly Gly Lys Val
305 310 315 320

Leu Ile Ile Glu Phe Val Leu Pro Asn Glu Leu Gly Asn Asn Ala Glu
325 330 335

Ser Phe Asn Ala Leu Ile Pro Asp Leu Leu Leu Met Ala Leu Asn Pro
340 345 350

Gly Gly Lys Glu Arg Thr Ile Ser Glu Tyr Asp Asp Leu Gly Lys Ala
355 360 365

Ala Gly Phe Ile Lys Thr Ile Pro Ile Pro Ile Ser Asn Gly Leu His
370 375 380

Val Ile Glu Phe His Lys
385 390

<210> SEQ ID NO 12
<211> LENGTH: 356
<212> TYPE: PRT
<213> ORGANISM: Papaver somniferum

<400> SEQUENCE: 12

Met Glu Ile His Leu Glu Ser Gln Glu Gln Glu Met Lys Tyr Gln Ser
1 5 10 15

Gln Ile Trp Asn Gln Ile Cys Gly Thr Val Asp Thr Ser Val Leu Arg
20 25 30

Cys Ala Ile Gln Leu Gly Ile Phe Asp Ala Ile His Asn Ser Gly Lys
35 40 45

Pro Met Ile Thr Leu Thr Glu Leu Ser Ser Ile Val Ser Ser Pro Ser
50 55 60

Ser Ser Ser Ile Glu Pro Cys Asn Leu Tyr Arg Leu Val Arg Tyr Leu
65 70 75 80

Ser Gln Met Asp Leu Ile Ser Ile Gly Glu Cys Leu Asn Glu Ala Thr
85 90 95

Val Ser Leu Thr Gly Thr Ser Lys Leu Leu Leu Arg Asn Gln Glu Lys
100 105 110

Ser Leu Ile Asp Trp Val Leu Ala Ile Ser Cys Glu Met Met Val Val
115 120 125

Val Trp His Glu Leu Ser Ser Ser Val Ser Thr Pro Ala Asp Glu Pro
130 135 140

Pro Ile Phe Gln Lys Val His Gly Lys Asn Ala Leu Glu Leu Ala Gly
145 150 155 160

Glu Phe Pro Glu Trp Asn Asp Leu Ile Asn Asn Ala Met Thr Ser Asp
165 170 175

Thr Ser Val Thr Lys Pro Ala Leu Ile Gln Gly Cys Gly Lys Ile Leu
180 185 190

Asn Gly Val Thr Ser Leu Ile Asp Val Gly Gly Gly His Gly Ala Thr
195 200 205

-continued

```
Met Ala Tyr Ile Val Glu Ala Phe Pro His Ile Lys Gly Ala Val Ile
    210                 215                 220

Asp Leu Pro His Val Val Glu Ala Ala Pro Glu Arg Pro Gly Val Glu
225                 230                 235                 240

Phe Ile Ser Gly Asp Ile Phe Lys Ser Ile Ser Asn Ala Asp Ala Val
                245                 250                 255

Leu Leu Lys Tyr Val Leu His Asn Trp Glu Asp Thr Glu Cys Val Asn
            260                 265                 270

Leu Leu Lys Arg Cys Lys Glu Ala Val Pro Ala Asp Lys Gly Lys Val
        275                 280                 285

Ile Ile Met Asp Leu Val Ile Asp Asp Asp Asp Asn Ser Ile Leu Thr
    290                 295                 300

Gln Ala Lys Leu Ser Leu Asp Leu Thr Val Met Asn His Gly Gly Gly
305                 310                 315                 320

Arg Glu Arg Thr Lys Glu Asp Trp Arg Asn Leu Ile Glu Met Ser Gly
                325                 330                 335

Phe Ser Arg His Glu Ile Ile Pro Ile Ser Ala Met Pro Ser Ile Ile
            340                 345                 350

Val Ala Tyr Pro
        355


<210> SEQ ID NO 13
<211> LENGTH: 339
<212> TYPE: PRT
<213> ORGANISM: Papaver somniferum

<400> SEQUENCE: 13

Met Glu Val Val Ser Lys Ile Asp Gln Glu Asn Gln Ala Lys Ile Trp
1               5                   10                  15

Lys Gln Ile Phe Gly Phe Ala Glu Ser Leu Val Leu Lys Cys Ala Val
            20                  25                  30

Gln Leu Glu Ile Ala Glu Thr Leu His Asn Asn Val Lys Pro Met Ser
        35                  40                  45

Leu Ser Glu Leu Ala Ser Lys Leu Pro Ala Gln Pro Val Asn Glu Asp
    50                  55                  60

Arg Leu Tyr Arg Ile Leu His Phe Leu Val His Met Lys Leu Phe Asn
65                  70                  75                  80

Lys Asp Ala Thr Thr Gln Lys Tyr Ser Leu Ala Pro Pro Ala Lys Tyr
                85                  90                  95

Leu Leu Lys Gly Trp Glu Lys Ser Met Val Pro Ser Ile Leu Ser Val
            100                 105                 110

Thr Asp Lys Asp Phe Thr Ala Pro Trp Asn His Leu Gly Asp Gly Leu
        115                 120                 125

Thr Gly Asn Cys Asn Ala Phe Glu Lys Ala Leu Gly Lys Gly Ile Arg
    130                 135                 140

Val Tyr Met Arg Glu Asn Pro Glu Lys Asp Gln Leu Phe Asn Glu Gly
145                 150                 155                 160

Met Ala Cys Asp Thr Arg Leu Phe Ala Ser Ala Leu Val Asn Glu Cys
                165                 170                 175

Lys Ser Ile Phe Ser Asp Gly Ile Asn Thr Leu Ala Gly Val Gly Arg
            180                 185                 190

Gly Thr Gly Thr Ala Val Lys Ala Ile Ser Lys Ala Phe Pro Asp Ile
        195                 200                 205

Lys Cys Thr Ile His Asp Leu Pro Glu Val Thr Ser Lys Asn Ser Lys
```

```
    210                 215                 220

Ile Pro Arg Asp Val Phe Lys Ser Val Pro Ser Ala Asp Ala Ile Phe
225                 230                 235                 240

Met Lys Ser Ile Leu His Glu Trp Asn Asp Glu Glu Cys Ile Gln Ile
                245                 250                 255

Leu Lys Arg Cys Lys Glu Ala Ile Pro Lys Gly Gly Lys Val Ile Ile
            260                 265                 270

Ala Asp Val Val Ile Asp Met Asp Ser Thr His Pro Tyr Ser Lys Ser
        275                 280                 285

Arg Leu Ala Met Asp Leu Ala Met Met Leu His Thr Gly Gly Lys Glu
    290                 295                 300

Arg Thr Glu Glu Asp Trp Lys Lys Leu Ile Asp Ala Ala Gly Phe Ala
305                 310                 315                 320

Ser Cys Lys Ile Thr Lys Leu Ser Ala Leu Gln Ser Val Ile Glu Ala
                325                 330                 335

Tyr Pro His


<210> SEQ ID NO 14
<211> LENGTH: 540
<212> TYPE: PRT
<213> ORGANISM: Papaver somniferum

<400> SEQUENCE: 14

Met Glu Leu Phe Ile Lys Leu Pro Phe Ile Gln Pro Ile Pro Phe Ser
1               5                   10                  15

Ile Ile Leu Val Thr Thr Val Ser Ile Val Leu Leu Tyr Ser Val Phe
            20                  25                  30

Phe Trp Val Thr Asp Lys Lys Lys Lys Arg Lys Lys Ala Pro Asn Ala
        35                  40                  45

Ala Gly Ala Trp Pro Leu Ile Gly His Leu Arg Leu Leu Met Asn Asp
    50                  55                  60

Lys Glu Pro Leu Tyr Arg Ala Leu Gly Ser Met Ala Asp Lys Tyr Gly
65                  70                  75                  80

Pro Ala Phe Asn Ile Arg Leu Gly Asn Gln Glu Val Leu Val Val Ser
                85                  90                  95

Asn Trp Glu Met Val Lys Gln Cys Phe Gly Asn Gln Asn Asp Lys Leu
            100                 105                 110

Phe Ser Asn Arg Gln Thr Thr Leu Ala Ala Lys Tyr Met Leu Asn Gln
        115                 120                 125

Thr Thr Ser Ser Gly Phe Ala Pro Tyr Gly Pro Tyr Trp Arg Glu Leu
    130                 135                 140

Arg Lys Ile Met Val Gln Gln Leu Leu Ser Lys Gln Ser Leu Glu Ser
145                 150                 155                 160

Trp Lys His Leu Lys Ile Lys Glu Met Asp Ala Ser Phe Ser Lys Leu
                165                 170                 175

Asn Glu Leu Cys Asn Asn Asn Gly Thr Gly Thr Ala Thr Leu Ile Arg
            180                 185                 190

Met Asp Glu Trp Phe Ala Glu Leu Thr Phe Asn Val Ile Ala Arg Asn
        195                 200                 205

Val Phe Gly Tyr Gln Ser Gly Gly Arg Ser Thr Ala Leu Thr Asn Gly
    210                 215                 220

Asp Thr Glu Ser Lys Gly Glu Arg Tyr Lys Lys Thr Leu Glu Glu Ala
225                 230                 235                 240

Leu His Leu Met Ser Ile Phe Ala Val Ser Asp Ile Phe Pro Ser Leu
```

```
                245                 250                 255

Glu Trp Val Asp Arg Leu Arg Gly Leu Ile Arg Asn Met Lys Arg Phe
            260                 265                 270

Gly Asp Glu Leu Asn Ser Ile Ala Gly Cys Leu Ile Glu Glu His Arg
        275                 280                 285

Gln Lys Arg Leu Gln Ser Val Ser Lys Ser Asp Lys Gly Val Gly Asp
    290                 295                 300

Glu Gln Asp Phe Val Asp Val Leu Leu Ser Val Ala Glu Lys Ser Gln
305                 310                 315                 320

Leu Pro Gly Asp Asp Pro Asp Leu Val Ile Lys Ser Met Ile Leu Glu
                325                 330                 335

Ile Val Ser Gly Gly Ser Glu Thr Thr Ser Ser Thr Leu Thr Trp Ala
            340                 345                 350

Leu Cys Leu Leu Leu Asn His Pro His Val Leu Lys Lys Ala Lys Glu
        355                 360                 365

Glu Leu Asp Thr His Val Gly Lys Asp Arg His Val Glu Glu Ser Asp
    370                 375                 380

Thr Pro Lys Leu Val Tyr Ile Asn Ala Ile Ile Lys Glu Ser Met Arg
385                 390                 395                 400

Leu Tyr Pro Asn Gly Ala Met Leu Asp Arg Leu Ala Leu Glu Glu Cys
                405                 410                 415

Glu Val Gly Gly Phe His Val Pro Ala Gly Gly Arg Leu Phe Val Asn
            420                 425                 430

Val Trp Lys Ile Gln Arg Asp Pro Ser Val Trp Glu Asn Pro Leu Glu
        435                 440                 445

Phe Lys Pro Glu Arg Trp Phe Leu Ser Asn Gly Glu Lys Met Asp Val
    450                 455                 460

Asp Tyr Lys Gly His Asn His Glu Phe Ile Pro Phe Gly Ile Gly Arg
465                 470                 475                 480

Arg Met Cys Ala Gly Met Leu Trp Ala Ser Glu Val Ile His Leu Val
                485                 490                 495

Leu Pro Arg Leu Ile His Gly Phe Asp Met Lys Ala Ala Ser Ala Asn
            500                 505                 510

Gly Lys Val Asp Met Ala Glu Met Ala Gly Met Val Ile Cys Phe Lys
        515                 520                 525

Lys Thr Pro Leu Glu Val Met Val Asn Pro Arg Glu
    530                 535                 540


<210> SEQ ID NO 15
<211> LENGTH: 486
<212> TYPE: PRT
<213> ORGANISM: Papaver somniferum

<400> SEQUENCE: 15

Met Ile Met Ser Asn Leu Trp Ile Leu Thr Leu Ile Ser Thr Ile Leu
1               5                   10                  15

Ala Val Phe Ala Ala Val Leu Ile Ile Phe Arg Arg Arg Ile Ser Ala
            20                  25                  30

Ser Thr Thr Glu Trp Pro Val Gly Pro Lys Thr Leu Pro Ile Ile Gly
        35                  40                  45

Asn Leu His Ile Leu Gly Gly Thr Ala Leu His Val Val Leu His Lys
    50                  55                  60

Leu Ala Glu Val Tyr Gly Ser Val Met Thr Ile Trp Ile Gly Ser Trp
65                  70                  75                  80
```

-continued

```
Lys Pro Val Ile Ile Val Ser Asp Phe Asp Arg Ala Trp Glu Val Leu
                85                  90                  95

Val Asn Lys Ser Ser Asp Tyr Ser Ala Arg Glu Met Pro Glu Ile Thr
            100                 105                 110

Lys Ile Gly Thr Ala Asn Trp Arg Thr Ile Ser Ser Ser Asp Ser Gly
        115                 120                 125

Pro Phe Trp Ala Thr Leu Arg Lys Gly Leu Gln Ser Val Ala Leu Ser
    130                 135                 140

Pro Gln His Leu Ala Ser Gln Thr Ala His Gln Glu Arg Asp Ile Ile
145                 150                 155                 160

Lys Leu Ile Lys Asn Leu Lys Asp Glu Ala Ala Ser Gly Met Val Lys
                165                 170                 175

Pro Leu Asp His Leu Lys Lys Ala Thr Val Arg Leu Ile Ser Arg Leu
            180                 185                 190

Ile Tyr Gly Gln Asp Phe Asp Asp Asp Lys Tyr Val Glu Asp Met His
        195                 200                 205

Asp Val Ile Glu Phe Leu Ile Arg Ile Ser Gly Tyr Ala Gln Leu Ala
    210                 215                 220

Glu Val Phe Tyr Tyr Ala Lys Tyr Leu Pro Gly His Lys Arg Ala Val
225                 230                 235                 240

Thr Gly Ala Glu Glu Ala Lys Arg Arg Val Ile Ala Leu Val Arg Pro
                245                 250                 255

Phe Leu Gln Ser Asn Pro Ala Thr Asn Thr Tyr Leu His Phe Leu Lys
            260                 265                 270

Ser Gln Leu Tyr Pro Glu Glu Val Ile Ile Phe Ala Ile Phe Glu Ala
        275                 280                 285

Tyr Leu Leu Gly Val Asp Ser Thr Ser Ser Thr Thr Ala Trp Ala Leu
    290                 295                 300

Ala Phe Leu Ile Arg Glu Pro Ser Val Gln Glu Lys Leu Tyr Gln Glu
305                 310                 315                 320

Leu Lys Asn Phe Thr Ala Asn Asn Asn Arg Thr Met Leu Lys Val Glu
                325                 330                 335

Asp Val Asn Lys Leu Pro Tyr Leu Gln Ala Val Val Lys Glu Thr Met
            340                 345                 350

Arg Met Lys Pro Ile Ala Pro Leu Ala Ile Pro His Lys Ala Cys Lys
        355                 360                 365

Asp Thr Ser Leu Met Gly Lys Lys Val Asp Lys Gly Thr Lys Val Met
    370                 375                 380

Val Asn Ile His Ala Leu His His Thr Glu Lys Val Trp Lys Glu Pro
385                 390                 395                 400

Tyr Lys Phe Ile Pro Glu Arg Phe Leu Gln Lys His Asp Lys Ala Met
                405                 410                 415

Glu Gln Ser Leu Leu Pro Phe Ser Ala Gly Met Arg Ile Cys Ala Gly
            420                 425                 430

Met Glu Leu Gly Lys Leu Gln Phe Ser Phe Ser Leu Ala Asn Leu Val
        435                 440                 445

Asn Ala Phe Lys Trp Ser Cys Val Ser Asp Gly Val Leu Pro Asp Met
    450                 455                 460

Ser Asp Leu Leu Gly Phe Val Leu Phe Met Lys Thr Pro Leu Glu Ala
465                 470                 475                 480

Arg Ile Val Pro Arg Leu
                485
```

-continued

<210> SEQ ID NO 16
<211> LENGTH: 554
<212> TYPE: PRT
<213> ORGANISM: Papaver somniferum

<400> SEQUENCE: 16

```
Met Lys Ser Leu Met Met Asn Lys Leu Leu Phe Leu Gln Arg Ile Thr
1               5                   10                  15

Asp Ser Pro Ser Thr Thr Ile Ile Ser Thr Phe Ile Val Thr Ile Ile
            20                  25                  30

Ser Ile Val Phe Leu Tyr Thr Val Leu Leu Ile Arg Thr Thr Lys Asn
        35                  40                  45

Lys Gln Lys Ile Ala Ala Pro Lys Ala Ser Gly Ala Trp Pro Phe Ile
    50                  55                  60

Gly His Leu Lys Leu Phe Met Lys Gln Asp Thr Gln Phe Tyr Arg Thr
65                  70                  75                  80

Leu Gly Thr Met Ser Asp Lys Tyr Gly Ser Val Phe Thr Leu Arg Leu
                85                  90                  95

Gly Asn Gln Ala Ile Leu Val Val Ser Asn Trp Glu Met Val Lys Glu
            100                 105                 110

Cys Phe Thr Thr Asn Asp Lys Ser Phe Ser Asn Arg Pro Ser Thr Leu
        115                 120                 125

Ser Thr Lys Tyr Met Leu Asn Asp Thr Asn Ser Val Val Phe Ser Pro
    130                 135                 140

Tyr Gly Thr Tyr Trp Arg Glu Met Arg Lys Ile Leu Val Gln Lys Leu
145                 150                 155                 160

Leu Ile Ser Asn Gln Arg Ser Glu Ala Leu Lys Asn Leu Lys Thr Lys
                165                 170                 175

Glu Ile Asp Asn Ser Phe Val Lys Leu Asn Asp Leu Cys Asn Asn Asp
            180                 185                 190

Val Ser Gly Gly Gly Thr Lys Val Arg Met Asp Glu Trp Leu Ala Asp
        195                 200                 205

Met Met Phe Asn Ile Ile Ala Arg Ile Thr Phe Gly Tyr Gln Ser Gly
    210                 215                 220

Gly Gly Asp Ala Pro Gly Ala Ser Thr Thr Ser Lys Asn Val Glu Arg
225                 230                 235                 240

Tyr Lys Lys Thr Leu Asp Glu Met Phe Val Val Leu Ala Thr Arg Phe
                245                 250                 255

Ala Val Ser Asp Ile Phe Pro Ser Leu Glu Phe Ile Asp Arg Leu Arg
            260                 265                 270

Gly Leu Val Lys Asp Met Lys Ile Leu Gly Asp Glu Leu Asn Ser Ile
        275                 280                 285

Ala Gly Cys Phe Ile Glu Glu His Arg Gln Lys Arg Arg Glu Ser Leu
    290                 295                 300

Ser Ser Leu Leu Ser Leu Ser Asn Glu Ser Val Gly Asp Glu Gln Asp
305                 310                 315                 320

Phe Ile Asp Val Leu Leu Ser Ile Met Asp Gln Ser Arg Leu Pro Gly
                325                 330                 335

Asp Asp Pro Asp Phe Ile Ile Lys Ile Met Ile Leu Glu Ala Phe Ala
            340                 345                 350

Gly Gly Thr Asp Ser Leu Ser Ala Thr Leu Thr Trp Val Leu Ser Leu
        355                 360                 365

Leu Leu Asn His Pro Asn Val Leu Lys Arg Ala Arg Glu Glu Ile Asp
    370                 375                 380
```

-continued

```
Arg His Val Glu Asn Gly Lys Gln Val Glu Val Ser Asp Ile Pro Lys
385                 390                 395                 400

Leu Gly Tyr Ile Asp Ala Ile Ile Lys Glu Thr Met Arg Leu Tyr Pro
                405                 410                 415

Val Gly Ala Leu Ser Glu Arg Tyr Thr Thr Glu Glu Cys Glu Val Gly
            420                 425                 430

Arg Phe Asn Val Pro Ala Gly Thr Arg Leu Leu Val Asn Ile Trp Lys
        435                 440                 445

Ile His Arg Asp Pro Ser Val Trp Glu Asn Pro Ser Asp Phe Gln Pro
    450                 455                 460

Glu Arg Phe Leu Cys Ser Asp Lys Val Gly Val Asp Leu Tyr Gly Gln
465                 470                 475                 480

Asn Tyr Glu Leu Ile Pro Phe Gly Ala Gly Arg Arg Val Cys Pro Ala
                485                 490                 495

Ile Val Ser Ser Leu Gln Thr Met His Tyr Ala Leu Ala Arg Leu Ile
            500                 505                 510

Gln Gly Tyr Glu Met Lys Ser Ala Ser Leu Asp Gly Lys Val Asn Met
        515                 520                 525

Glu Glu Met Ile Ala Met Ser Cys His Lys Met Ser Pro Leu Glu Val
    530                 535                 540

Ile Ile Ser Pro Arg Glu Pro Arg Arg Ser
545                 550


<210> SEQ ID NO 17
<211> LENGTH: 556
<212> TYPE: PRT
<213> ORGANISM: Papaver somniferum

<400> SEQUENCE: 17

Met Ala Tyr Leu Met Ile Lys Lys Ser Ile Tyr Leu Phe Phe Asp Gln
1               5                   10                  15

Pro Thr Ala Val Gly Thr Leu Ile Leu Ala Phe Leu Leu Thr Leu Ser
            20                  25                  30

Pro Val Ile Ile Tyr Tyr Glu Gln Lys Lys Arg Gly Leu Arg Arg Asn
        35                  40                  45

Arg Thr Ala Ile Thr Thr Thr Pro Leu Pro Glu Ala Ser Gly Ala Trp
    50                  55                  60

Pro Val Ile Gly His Leu Leu Leu Phe Met Asn Glu Asn Asp Leu Asn
65                  70                  75                  80

His Val Thr Leu Gly His Met Ala Asp Lys Tyr Gly Pro Ile Phe Ser
                85                  90                  95

Leu Arg Phe Gly Arg His Arg Thr Leu Val Val Ser Ser Trp Glu Met
            100                 105                 110

Val Lys Glu Cys Phe Thr Gly Thr Asn Asp Lys Leu Phe Ser Asn Arg
        115                 120                 125

Pro Ser Ser Leu Ala Val Lys Leu Met Phe Tyr Asp Thr Glu Ser Tyr
    130                 135                 140

Gly Phe Ala Pro Tyr Gly Lys Tyr Trp Arg Glu Leu Arg Lys Ile Ser
145                 150                 155                 160

Thr His Lys Leu Leu Ser Asn Gln Gln Leu Glu Lys Phe Lys His Leu
                165                 170                 175

Arg Ile Ser Glu Val Asp Asn Ser Phe Lys Lys Leu His Glu Leu Cys
            180                 185                 190

Ser Asn Asn Lys Gln Gly Gly Asp Thr Thr Tyr Val Ala Ser Leu Val
        195                 200                 205
```

```
Arg Met Asp Asp Trp Phe Ala Tyr Leu Thr Phe Asn Val Ile Gly Arg
    210                 215                 220

Ile Val Ser Gly Phe Gln Ser Asn Ala Val Ala Gly Ala Thr Asn Ser
225                 230                 235                 240

Gln Glu Lys Tyr Lys Leu Ala Ile Asp Glu Val Ser Asn Leu Met Ala
                245                 250                 255

Thr Phe Ala Val Ser Asp Val Val Pro Arg Leu Gly Trp Ile Asp Arg
            260                 265                 270

Leu Thr Gly Leu Thr Gly Lys Met Lys Asn Cys Gly Lys Lys Leu Asp
        275                 280                 285

Ala Val Val Gly Asp Ala Val Glu Asp His Arg Gln Lys Lys Leu Lys
    290                 295                 300

Ile Ser Arg Asn Asn Thr Gly Ala Leu Thr Glu His Glu Glu Glu Asp
305                 310                 315                 320

Phe Ile Asp Val Cys Leu Ser Ile Met Glu Gln Ser Gln Ile Pro Gly
                325                 330                 335

Asn His Pro Glu Ile Ser Val Lys Ser Ile Ala Leu Asp Met Leu Ser
            340                 345                 350

Gly Gly Ser Asp Thr Thr Lys Leu Ile Met Thr Trp Thr Leu Ser Leu
        355                 360                 365

Leu Leu Asn His Pro Asp Ile Leu Asp Lys Ala Lys Glu Glu Val Asp
    370                 375                 380

Thr Tyr Phe Gly Lys Lys Lys Ile Ser Asp Asn Thr Pro Val Val Asp
385                 390                 395                 400

Ala Ala Asp Val Pro Asn Leu Val Tyr Ile Gln Ala Ile Ile Lys Glu
                405                 410                 415

Ser Met Arg Leu Tyr Pro Ala Ser Thr Leu Met Glu Arg Met Thr Ser
            420                 425                 430

Asp Asp Cys Asp Val Gly Gly Phe His Val Pro Ala Gly Thr Arg Leu
        435                 440                 445

Trp Val Asn Val Trp Lys Met Gln Arg Asp Pro Arg Val Trp Lys Asp
    450                 455                 460

Pro Leu Val Phe Leu Pro Glu Arg Phe Leu Ser Asn Asp Lys Gly Met
465                 470                 475                 480

Val Asp Val Lys Gly Gln Asn Tyr Glu Leu Ile Pro Phe Gly Thr Gly
                485                 490                 495

Arg Arg Ile Cys Pro Gly Ala Ser Phe Ala Leu Glu Val Leu His Leu
            500                 505                 510

Val Leu Thr Arg Leu Ile Leu Glu Phe Glu Met Lys Ala Pro Glu Gly
        515                 520                 525

Lys Ile Asp Met Arg Ala Arg Pro Gly Phe Phe His Asn Lys Val Val
    530                 535                 540

Pro Leu Asp Val Gln Leu Thr Pro Arg Thr Leu Asp
545                 550                 555


<210> SEQ ID NO 18
<211> LENGTH: 320
<212> TYPE: PRT
<213> ORGANISM: Papaver somniferum

<400> SEQUENCE: 18

Met Ala Asp Pro Tyr Glu Phe Leu Met Cys Ile His Asn Pro Glu Glu
1               5                   10                  15

Asp Thr Leu Thr Arg Asn Phe Pro Ile Pro Ala Thr Pro Leu Asp Gln
```

```
            20                  25                  30

Asn Thr Lys Asp Ile Ser Leu Asn Pro Asp Arg Lys Thr Ser Leu Arg
        35                  40                  45

Ile Phe Arg Pro Pro Thr Lys Glu Pro Pro Val Thr Lys Asn Lys Leu
    50                  55                  60

Leu Pro Ile Ile Ile Tyr Phe His Gly Gly Gly Phe Ile Leu Phe Asn
65                  70                  75                  80

Ala Asp Ser Thr Met Asn His Asp Phe Cys Gln Ser Ile Ala Thr His
                85                  90                  95

Ile Pro Ala Leu Val Val Ser Val Asp Tyr Arg Leu Ala Pro Glu Asn
            100                 105                 110

Arg Leu Pro Ala Ala Tyr Asp Asp Ala Val Asp Ala Leu Asn Trp Val
        115                 120                 125

Lys Asp Gln Gly Leu Gly Lys Leu Asn Asn Ser Glu Val Trp Leu Lys
    130                 135                 140

Glu Tyr Gly Asp Phe Ser Lys Cys Phe Ile Met Gly Cys Ser Ser Gly
145                 150                 155                 160

Ala Asn Val Ala Tyr His Ala Ser Leu Arg Ala Ile Glu Met Asp Leu
                165                 170                 175

Glu Pro Ala Lys Ile Asn Gly Leu Ile Leu His Cys Pro Phe Phe Gly
            180                 185                 190

Ser Leu Glu Arg Thr Glu Ser Asp Ser Lys Val Ile Asn Asn Gln Asp
        195                 200                 205

Leu Pro Leu Ala Val Arg Asp Val Met Trp Glu Leu Ala Leu Pro Leu
    210                 215                 220

Gly Ser Thr Arg Asp His Val Tyr Cys Asn Pro Asn Ile Asp His Asp
225                 230                 235                 240

Gly Ser Ser Ser Gly Asn Met Val Gly Leu Ile Glu Arg Cys Phe Val
                245                 250                 255

Val Gly Phe Tyr Gly Asp Pro Leu Ile Asp Arg Gln Ile Gln Leu Val
            260                 265                 270

Lys Met Leu Glu Glu Lys Gly Val Lys Val Glu Thr Trp Ile Glu Gln
        275                 280                 285

Gly Gly Tyr His Gly Val Leu Cys Phe Asp Pro Met Ile Arg Glu Thr
    290                 295                 300

Phe Leu Glu Lys Leu Lys His Phe Ile Leu Asn Asp Glu Phe Ile Tyr
305                 310                 315                 320


<210> SEQ ID NO 19
<211> LENGTH: 348
<212> TYPE: PRT
<213> ORGANISM: Papaver somniferum

<400> SEQUENCE: 19

Met His Gly Gln Lys Asn Ile Ser Glu Arg Tyr Gln Lys Phe Lys Glu
1               5                   10                  15

Met Glu Gly Thr Gly Lys Ile Val Cys Val Thr Gly Gly Ala Gly Tyr
            20                  25                  30

Leu Ala Ser Trp Leu Ile Met Arg Leu Leu Glu Arg Gly Tyr Ser Val
        35                  40                  45

Arg Thr Thr Val Arg Ser Asp Pro Lys Phe Arg Glu Asp Val Ser His
    50                  55                  60

Leu Lys Ala Leu Pro Glu Ala Thr Glu Lys Leu Gln Ile Phe Glu Ala
65                  70                  75                  80
```

-continued

```
Asp Leu Glu Asn Pro Glu Ser Phe Asp Asp Ala Ile Asn Gly Cys Val
                85                  90                  95

Gly Val Phe Leu Val Ala Gln Gly Met Asn Phe Ala Glu Glu Tyr Thr
            100                 105                 110

Leu Glu Lys Ile Ile Lys Thr Cys Val Glu Gly Thr Leu Arg Ile Leu
        115                 120                 125

Gln Ser Cys Leu Lys Ser Lys Thr Val Lys Lys Val Val Tyr Thr Ser
    130                 135                 140

Ser Ala Asp Ala Ala Met Met Ile Ser Asn Leu Lys Ala Val Lys Glu
145                 150                 155                 160

Ile Asp Glu Thr Ile Trp Ser Glu Val Asp Asn Phe Ile Ser Lys Pro
                165                 170                 175

Glu Gln Val Ile Pro Gly Leu Pro Ser Tyr Val Val Ser Lys Val Leu
            180                 185                 190

Thr Glu Arg Ala Cys Leu Lys Phe Ser Glu Glu His Gly Leu Asp Val
        195                 200                 205

Val Thr Ile Leu Pro Pro Leu Val Val Gly Pro Phe Ile Thr Pro His
    210                 215                 220

Pro Pro Pro Ser Val Ser Ile Ala Leu Ser Ile Ile Ser Gly Asp Val
225                 230                 235                 240

Ser Met Met Leu Gly Val Arg Leu Glu Asn Ala Val His Ile Asp Asp
                245                 250                 255

Val Ala Leu Ala His Ile Phe Val Phe Glu Cys Glu Lys Ala Lys Gly
            260                 265                 270

Arg His Ile Cys Ser Ser Val Asp Phe Pro Met His Asp Leu Pro Lys
        275                 280                 285

Phe Ile Ser Glu Asn Tyr Pro Glu Phe Asn Val Pro Thr Asp Leu Leu
    290                 295                 300

Lys Asp Ile Glu Glu Gln Glu Pro Val His Leu Ser Ser Asp Lys Leu
305                 310                 315                 320

Leu Ser Met Gly Phe Gln Phe Lys Tyr Asp Phe Ala Glu Ile Phe Gly
                325                 330                 335

Asp Ala Ile Arg Cys Ala Lys Glu Lys Gly Phe Leu
            340                 345


<210> SEQ ID NO 20
<211> LENGTH: 471
<212> TYPE: PRT
<213> ORGANISM: Papaver somniferum

<400> SEQUENCE: 20

Met Ala Thr Met Ser Ser Ala Ala Val Glu Val Ile Ser Lys Glu Thr
1               5                   10                  15

Ile Lys Pro Arg Asn Pro Thr Pro Tyr Gln Leu Arg Asn Tyr Asn Met
            20                  25                  30

Ser Leu Leu Asp Gln Tyr Ser Ser Leu Val Tyr Val Pro Ile Ile Leu
        35                  40                  45

Phe Tyr Pro Ala Ala Ser Asp Ala Asn Ser Thr Gly Ser Lys His His
    50                  55                  60

Asp Asp Leu His Leu Leu Lys Arg Ser Leu Ser Glu Thr Leu Val His
65                  70                  75                  80

Phe Tyr Pro Met Ala Gly Arg Met Lys Asp Asn Met Thr Val Asp Cys
                85                  90                  95

Asn Asp Glu Gly Ile Asp Phe Phe Glu Val Arg Ile Lys Gly Arg Met
            100                 105                 110
```

-continued

```
Cys Asp Phe Met Met Lys Ser Asp Ala His Leu Ser Leu Leu Leu Pro
        115                 120                 125

Ser Glu Val Ala Ser Thr Asn Phe Val Lys Glu Ala Gln Val Ile Val
    130                 135                 140

Gln Val Asn Met Phe Asp Cys Gly Gly Thr Ala Ile Cys Phe Cys Ile
145                 150                 155                 160

Ser Asn Lys Ile Ala Asp Ala Cys Thr Met Ile Thr Phe Ile Arg Ser
                165                 170                 175

Leu Ala Gly Thr Thr Asn Ile Ala Arg Arg Gly Ser Ser Ile Ala Ala
            180                 185                 190

Pro Thr Thr Asn Gln Asn Leu Val Pro Ser Phe Asp Ser Thr Ser Leu
        195                 200                 205

Phe Pro Pro Ser Glu Gln Leu Ala Ser Gln Val Ser Tyr Pro Thr Gln
    210                 215                 220

Asp Ser Thr Ser Val Asp Lys Leu Val Ser Lys Arg Phe Val Phe Asp
225                 230                 235                 240

Ala Ala Lys Ile Thr Ser Ala Arg Glu Lys Leu Gln Ser Leu Met His
                245                 250                 255

Asp Lys Tyr Lys Cys His Arg Pro Thr Arg Val Glu Val Val Ser Ala
            260                 265                 270

Leu Ile Trp Lys Ser Ala Val Lys Ser Ala Pro Pro Gly Ser Ile Ser
        275                 280                 285

Thr Val Thr His Ala Met Asn Phe Arg Lys Lys Met Asp Pro Pro Leu
    290                 295                 300

Gln Asp Ala Ser Phe Gly Asn Leu Cys Val Val Val Thr Ala Val Leu
305                 310                 315                 320

Pro Ala Thr Thr Ala Thr Thr Thr Asn Pro Ala Thr Lys Lys Val Ser
                325                 330                 335

Ser Thr Ser Asn Glu Glu Gln Val Ala Leu Asp Glu Leu Ser Asp Phe
            340                 345                 350

Val Ala Leu Leu Arg Arg Glu Ile Asp Lys Val Lys Gly Asp Lys Gly
        355                 360                 365

Cys Met Glu Lys Ile Ile Gln Lys Phe Ile Tyr Gly His Asp Ala Ser
    370                 375                 380

Val Ala Lys Asp Ser Asp Val Glu Asp Lys Val Thr Ala Leu Phe Met
385                 390                 395                 400

Thr Ser Trp Cys Lys Phe Gly Phe Tyr Glu Ala Asp Phe Gly Trp Gly
                405                 410                 415

Thr Pro Val Trp Val Thr Thr Val Pro Leu Ile Glu Pro Lys Tyr Lys
            420                 425                 430

Asn Met Val Phe Met Asn Asp Met Lys Cys Gly Glu Gly Ile Glu Val
        435                 440                 445

Trp Val Asn Phe Leu Glu Asp Asp Met Thr Lys Phe Glu His His Leu
    450                 455                 460

Arg Glu Ile Leu Gln Leu Phe
465                 470
```

<210> SEQ ID NO 21
<211> LENGTH: 350
<212> TYPE: DNA
<213> ORGANISM: Artificial Sequence
<220> FEATURE:
<223> OTHER INFORMATION: VIGS

<400> SEQUENCE: 21

```
tggtcataat catcaatcag ccacagtcac taaaatcact gcttctaatg aaagcagcaa     60

tggtgtctgt tatctttcag aaacggctaa cttggggaag ttaatatgca ttccaatggc    120

actaagagct gcgatggagc taaatgtgtt ccaacttatc tcaaagttcg gaactgacgc    180

aaaagtttcg gcttctgaaa ttgcctctaa aatgccaaac gcgaagaata atcctgaagc    240

agctatgtat ttggatagaa ttcttcgact gctcggggca agttctattc tttctgtttc    300

tactacaaaa aaatcaatca acagaggagg agatgatgta gtagtacatg               350


<210> SEQ ID NO 22
<211> LENGTH: 213
<212> TYPE: DNA
<213> ORGANISM: artificial sequence
<220> FEATURE:
<223> OTHER INFORMATION: VIGS

<400> SEQUENCE: 22

gtgtaactaa gccagcgcta atacaaggat gtggcaaaat cctgaacgga gttacatcgt     60

taattgatgt cggtggtggt cacggtgcca ctatggccta catagttgaa gcttttcctc    120

acataaaagg tgcggtaatc gatttaccac atgttgttga agccgctccg gagcgtccag    180

gtgttgagtt catcagcggt gatatattca agt                                 213


<210> SEQ ID NO 23
<211> LENGTH: 264
<212> TYPE: DNA
<213> ORGANISM: artificial sequence
<220> FEATURE:
<223> OTHER INFORMATION: VIGS

<400> SEQUENCE: 23

tttgagtaat ggtgaaaaga tggatgtgga ttacaaaggt cacaatcatg aattcatacc     60

atttgggata ggtcggagga tgtgcgctgg tatgctttgg gcatcggagg tgattcattt    120

ggtgctgccc cgtcttattc atgggtttga tatgaaagca gcaagtgcca atgggaaagt    180

agatatggca gaaatggcag gcatggtgat ttgttttaag aagacacctc ttgaagttat    240

ggtcaatcct cgagagtaga tgtt                                           264


<210> SEQ ID NO 24
<211> LENGTH: 119
<212> TYPE: DNA
<213> ORGANISM: artificial sequence
<220> FEATURE:
<223> OTHER INFORMATION: VIGS

<400> SEQUENCE: 24

atgatcatga gtaacttatg gattcttacg ctcatttcta ccatattagc agtctttgct     60

gctgtgttaa tcattttcag gagaagaata tcagcatcca caacggaatg gcctgttgg     119


<210> SEQ ID NO 25
<211> LENGTH: 196
<212> TYPE: DNA
<213> ORGANISM: artificial sequence
<220> FEATURE:
<223> OTHER INFORMATION: VIGS

<400> SEQUENCE: 25

taggagggta tgtccggcta tagtttcatc actgcagacg atgcattatg cgttggcgcg     60

tcttattcaa ggatatgaaa tgaaatcagc cagcctcgat gggaaggtga atatggaaga    120
```

-continued

```
aatgatagcc atgtcgtgcc acaagatgag ccctcttgaa gttattatca gtcctcggga    180

gccgaggcgg agttaa                                                    196


<210> SEQ ID NO 26
<211> LENGTH: 186
<212> TYPE: DNA
<213> ORGANISM: artificial sequence
<220> FEATURE:
<223> OTHER INFORMATION: VIGS

<400> SEQUENCE: 26

tcctatatat gctaattaat tagatgaata aaatctgtgg tcgagtaaat ctaattaatg     60

ctaatgaaca agatgaataa aaaattttct ttctgctttt gctttggtta gggttatttg    120

accctcattt ggttgtattc gttggcgcac aacttttgtg cttcttaata taattccttt    180

tggtgg                                                               186


<210> SEQ ID NO 27
<211> LENGTH: 204
<212> TYPE: DNA
<213> ORGANISM: artificial sequence
<220> FEATURE:
<223> OTHER INFORMATION: VIGS

<400> SEQUENCE: 27

tggcagatcc ttatgaattc ctaatgtgca ttcacaatcc tgaagaagat accctaacaa     60

gaaattttcc gattcctgct actcccttag atcaaaacac caaagacatt tctttaaatc    120

ctgataggaa aacctcactt cgaatctttc ggccaccaac caaagaacct cctgtaacaa    180

agaataagct gcttcctatc ataa                                           204


<210> SEQ ID NO 28
<211> LENGTH: 323
<212> TYPE: DNA
<213> ORGANISM: artificial sequence
<220> FEATURE:
<223> OTHER INFORMATION: VIGS

<400> SEQUENCE: 28

gaaattgacg agacaatatg gtcagaagtt gacaatttca ttagcaaacc ggaacaagtt     60

attcctggat tgccctcata tgtggtttca aaggtactga cagaaagagc ttgcctaaag    120

ttttctgaag aacatggttt ggatgttgtt actatacttc ctccgttggt tgttggacct    180

tttatcactc cccatcctcc tcccagtgta tctatagctc tttcgataat ttcaggtgat    240

gtgtcgatga tgcttggtgt tagacttgaa aatgcggtac atatagatga tgttgcttta    300

gcacacatat tcgtttttga atg                                            323


<210> SEQ ID NO 29
<211> LENGTH: 117
<212> TYPE: DNA
<213> ORGANISM: artificial sequence
<220> FEATURE:
<223> OTHER INFORMATION: VIGS

<400> SEQUENCE: 29

cctaagagag atcctccaac tgttttgatt ttcaaccgtt tccctaatag aggtcaattg     60

tcgtgtttgt ccatcttaac taccatcttt attctcttgt tttcatactt gtatttg       117


<210> SEQ ID NO 30
<211> LENGTH: 129
```

-continued

<212> TYPE: DNA
<213> ORGANISM: artificial sequence
<220> FEATURE:
<223> OTHER INFORMATION: VIGS

<400> SEQUENCE: 30
gatcatcttc tcttcagcag aagtcccctc ttaagcgtat acgctgacat gtcagtgaca 60
tgcaaggaat attatgaccc aaacaaatcc atgcttgagt tggtatttgc acccgctgag 120
gaatggatc 129

<210> SEQ ID NO 31
<211> LENGTH: 22
<212> TYPE: DNA
<213> ORGANISM: artificial sequence
<220> FEATURE:
<223> OTHER INFORMATION: Primer

<400> SEQUENCE: 31
gattcccgat ttactcctga tg 22

<210> SEQ ID NO 32
<211> LENGTH: 30
<212> TYPE: DNA
<213> ORGANISM: artificial sequence
<220> FEATURE:
<223> OTHER INFORMATION: Primer

<400> SEQUENCE: 32
aacacaaaat acgattactt acttttgtcc 30

<210> SEQ ID NO 33
<211> LENGTH: 23
<212> TYPE: DNA
<213> ORGANISM: artificial sequence
<220> FEATURE:
<223> OTHER INFORMATION: Primer

<400> SEQUENCE: 33
tgcctcatgt tatttctgtt gcc 23

<210> SEQ ID NO 34
<211> LENGTH: 26
<212> TYPE: DNA
<213> ORGANISM: artificial sequence
<220> FEATURE:
<223> OTHER INFORMATION: Primer

<400> SEQUENCE: 34
gcatgaaatg gatgtagtta tcttgg 26

<210> SEQ ID NO 35
<211> LENGTH: 22
<212> TYPE: DNA
<213> ORGANISM: artificial sequence
<220> FEATURE:
<223> OTHER INFORMATION: Primer

<400> SEQUENCE: 35
attgatgtcg gtggtggtca cg 22

<210> SEQ ID NO 36
<211> LENGTH: 24
<212> TYPE: DNA
<213> ORGANISM: artificial sequence
<220> FEATURE:

<223> OTHER INFORMATION: Primer

<400> SEQUENCE: 36
attcccgttc aagtaaacat gcgg 24

<210> SEQ ID NO 37
<211> LENGTH: 27
<212> TYPE: DNA
<213> ORGANISM: artificial sequence
<220> FEATURE:
<223> OTHER INFORMATION: Primer

<400> SEQUENCE: 37
gcaactgttt cattaacagg cacatcc 27

<210> SEQ ID NO 38
<211> LENGTH: 29
<212> TYPE: DNA
<213> ORGANISM: artificial sequence
<220> FEATURE:
<223> OTHER INFORMATION: Primer

<400> SEQUENCE: 38
cagtaaattc acacattccg tatcttccc 29

<210> SEQ ID NO 39
<211> LENGTH: 24
<212> TYPE: DNA
<213> ORGANISM: artificial sequence
<220> FEATURE:
<223> OTHER INFORMATION: Primer

<400> SEQUENCE: 39
gcttcagcat tggttaacga gtgc 24

<210> SEQ ID NO 40
<211> LENGTH: 26
<212> TYPE: DNA
<213> ORGANISM: artificial sequence
<220> FEATURE:
<223> OTHER INFORMATION: Primer

<400> SEQUENCE: 40
gagggtaagc ctcaataaca gactgg 26

<210> SEQ ID NO 41
<211> LENGTH: 23
<212> TYPE: DNA
<213> ORGANISM: artificial sequence
<220> FEATURE:
<223> OTHER INFORMATION: Primer

<400> SEQUENCE: 41
agaccgtttg taccgaattc tgc 23

<210> SEQ ID NO 42
<211> LENGTH: 22
<212> TYPE: DNA
<213> ORGANISM: artificial sequence
<220> FEATURE:
<223> OTHER INFORMATION: Primer

<400> SEQUENCE: 42
tcgttccatt cgtgaagaat gc 22

<210> SEQ ID NO 43
<211> LENGTH: 25
<212> TYPE: DNA
<213> ORGANISM: artificial sequence
<220> FEATURE:
<223> OTHER INFORMATION: Primer

<400> SEQUENCE: 43
gaaccattaa acacttgagt catgc 25

<210> SEQ ID NO 44
<211> LENGTH: 24
<212> TYPE: DNA
<213> ORGANISM: artificial sequence
<220> FEATURE:
<223> OTHER INFORMATION: Primer

<400> SEQUENCE: 44
tgcaattgaa tttagctcat ctcc 24

<210> SEQ ID NO 45
<211> LENGTH: 21
<212> TYPE: DNA
<213> ORGANISM: artificial sequence
<220> FEATURE:
<223> OTHER INFORMATION: Primer

<400> SEQUENCE: 45
ttgatgaacg acaaggaacc g 21

<210> SEQ ID NO 46
<211> LENGTH: 26
<212> TYPE: DNA
<213> ORGANISM: artificial sequence
<220> FEATURE:
<223> OTHER INFORMATION: Primer

<400> SEQUENCE: 46
attcatgatt gtgacctttg taatcc 26

<210> SEQ ID NO 47
<211> LENGTH: 24
<212> TYPE: DNA
<213> ORGANISM: artificial sequence
<220> FEATURE:
<223> OTHER INFORMATION: Primer

<400> SEQUENCE: 47
atgtggaaaa cggtaagcaa gtgg 24

<210> SEQ ID NO 48
<211> LENGTH: 25
<212> TYPE: DNA
<213> ORGANISM: artificial sequence
<220> FEATURE:
<223> OTHER INFORMATION: Primer

<400> SEQUENCE: 48
acgattctgt catcatcatt ttcgc 25

<210> SEQ ID NO 49
<211> LENGTH: 23
<212> TYPE: DNA
<213> ORGANISM: artificial sequence
<220> FEATURE:
<223> OTHER INFORMATION: Primer -continued

<400> SEQUENCE: 49
caacctcaat ctagctagag tcg 23

<210> SEQ ID NO 50
<211> LENGTH: 25
<212> TYPE: DNA
<213> ORGANISM: artificial sequence
<220> FEATURE:
<223> OTHER INFORMATION: Primer

<400> SEQUENCE: 50
cccaagattt tcatatcctt tacaa 25

<210> SEQ ID NO 51
<211> LENGTH: 31
<212> TYPE: DNA
<213> ORGANISM: artificial sequence
<220> FEATURE:
<223> OTHER INFORMATION: Primer

<400> SEQUENCE: 51
caataattga gtaatttcag ttcattcatg g 31

<210> SEQ ID NO 52
<211> LENGTH: 20
<212> TYPE: DNA
<213> ORGANISM: artificial sequence
<220> FEATURE:
<223> OTHER INFORMATION: Primer

<400> SEQUENCE: 52
gctccgtaag tgctcctgtg 20

<210> SEQ ID NO 53
<211> LENGTH: 26
<212> TYPE: DNA
<213> ORGANISM: artificial sequence
<220> FEATURE:
<223> OTHER INFORMATION: Primer

<400> SEQUENCE: 53
gaattgtggt aaaaaattag atgcag 26

<210> SEQ ID NO 54
<211> LENGTH: 22
<212> TYPE: DNA
<213> ORGANISM: artificial sequence
<220> FEATURE:
<223> OTHER INFORMATION: Primer

<400> SEQUENCE: 54
cccttcacat ctaccatccc tt 22

<210> SEQ ID NO 55
<211> LENGTH: 27
<212> TYPE: DNA
<213> ORGANISM: artificial sequence
<220> FEATURE:
<223> OTHER INFORMATION: Primer

<400> SEQUENCE: 55
caaagagtca atctgactca agctagc 27

<210> SEQ ID NO 56
<211> LENGTH: 18

-continued

<212> TYPE: DNA
<213> ORGANISM: artificial sequence
<220> FEATURE:
<223> OTHER INFORMATION: Primer

<400> SEQUENCE: 56
cgagtgccca tgcagtgg 18

<210> SEQ ID NO 57
<211> LENGTH: 28
<212> TYPE: DNA
<213> ORGANISM: artificial sequence
<220> FEATURE:
<223> OTHER INFORMATION: Primer

<400> SEQUENCE: 57
tcaaaccctg ctactaacac ttacttgc 28

<210> SEQ ID NO 58
<211> LENGTH: 23
<212> TYPE: DNA
<213> ORGANISM: artificial sequence
<220> FEATURE:
<223> OTHER INFORMATION: Primer

<400> SEQUENCE: 58
cactccatca gacacacaag acc 23

<210> SEQ ID NO 59
<211> LENGTH: 27
<212> TYPE: DNA
<213> ORGANISM: artificial sequence
<220> FEATURE:
<223> OTHER INFORMATION: Primer

<400> SEQUENCE: 59
ttttatcgac cttgaggaac aattagg 27

<210> SEQ ID NO 60
<211> LENGTH: 18
<212> TYPE: DNA
<213> ORGANISM: artificial sequence
<220> FEATURE:
<223> OTHER INFORMATION: Primer

<400> SEQUENCE: 60
aaatggcagt tccaccgc 18

<210> SEQ ID NO 61
<211> LENGTH: 25
<212> TYPE: DNA
<213> ORGANISM: artificial sequence
<220> FEATURE:
<223> OTHER INFORMATION: Primer

<400> SEQUENCE: 61
gacttcatga tgaaatcaga tgcac 25

<210> SEQ ID NO 62
<211> LENGTH: 24
<212> TYPE: DNA
<213> ORGANISM: artificial sequence
<220> FEATURE:
<223> OTHER INFORMATION: Primer

<400> SEQUENCE: 62

-continued cactgctgac ttccatatca aagc 24

<210> SEQ ID NO 63
<211> LENGTH: 24
<212> TYPE: DNA
<213> ORGANISM: artificial sequence
<220> FEATURE:
<223> OTHER INFORMATION: Primer

<400> SEQUENCE: 63
atgctgttga tgctttaaac tggg 24

<210> SEQ ID NO 64
<211> LENGTH: 26
<212> TYPE: DNA
<213> ORGANISM: artificial sequence
<220> FEATURE:
<223> OTHER INFORMATION: Primer

<400> SEQUENCE: 64
agctgaattt gtcgatcaat aagtgg 26

<210> SEQ ID NO 65
<211> LENGTH: 26
<212> TYPE: DNA
<213> ORGANISM: artificial sequence
<220> FEATURE:
<223> OTHER INFORMATION: Primer

<400> SEQUENCE: 65
aataaaaatc caacaatggc agatcc 26

<210> SEQ ID NO 66
<211> LENGTH: 24
<212> TYPE: DNA
<213> ORGANISM: artificial sequence
<220> FEATURE:
<223> OTHER INFORMATION: Primer

<400> SEQUENCE: 66
actggcatga tatgcaacat tagc 24

<210> SEQ ID NO 67
<211> LENGTH: 24
<212> TYPE: DNA
<213> ORGANISM: artificial sequence
<220> FEATURE:
<223> OTHER INFORMATION: Primer

<400> SEQUENCE: 67
ggaagatgtg agccacctta aagc 24

<210> SEQ ID NO 68
<211> LENGTH: 22
<212> TYPE: DNA
<213> ORGANISM: artificial sequence
<220> FEATURE:
<223> OTHER INFORMATION: Primer

<400> SEQUENCE: 68
gatacactgg gaggaggatg gg 22

<210> SEQ ID NO 69
<211> LENGTH: 26
<212> TYPE: DNA
<213> ORGANISM: artificial sequence
<220> FEATURE:
<223> OTHER INFORMATION: Primer

<400> SEQUENCE: 69
gagagtaacc acatctttgt tgtcgg 26

<210> SEQ ID NO 70
<211> LENGTH: 22
<212> TYPE: DNA
<213> ORGANISM: artificial sequence
<220> FEATURE:
<223> OTHER INFORMATION: Primer

<400> SEQUENCE: 70
cggcaaaatt cattccttga gc 22

<210> SEQ ID NO 71
<211> LENGTH: 19
<212> TYPE: DNA
<213> ORGANISM: artificial sequence
<220> FEATURE:
<223> OTHER INFORMATION: Primer

<400> SEQUENCE: 71
gtttactccc acgtgcatc 19

<210> SEQ ID NO 72
<211> LENGTH: 23
<212> TYPE: DNA
<213> ORGANISM: artificial sequence
<220> FEATURE:
<223> OTHER INFORMATION: Primer

<400> SEQUENCE: 72
cattcctcgt ctaattcatc tgc 23

<210> SEQ ID NO 73
<211> LENGTH: 19
<212> TYPE: DNA
<213> ORGANISM: artificial sequence
<220> FEATURE:
<223> OTHER INFORMATION: Primer

<400> SEQUENCE: 73
gtttactccc acgtgcatc 19

<210> SEQ ID NO 74
<211> LENGTH: 24
<212> TYPE: DNA
<213> ORGANISM: artificial sequence
<220> FEATURE:
<223> OTHER INFORMATION: Primer

<400> SEQUENCE: 74
gcttcactac ttcttcttga aaag 24

<210> SEQ ID NO 75
<211> LENGTH: 18
<212> TYPE: DNA
<213> ORGANISM: artificial sequence
<220> FEATURE:
<223> OTHER INFORMATION: Primer

<400> SEQUENCE: 75
aaacaatgct ggggttgc 18

<210> SEQ ID NO 76
<211> LENGTH: 26
<212> TYPE: DNA
<213> ORGANISM: artificial sequence
<220> FEATURE:
<223> OTHER INFORMATION: Primer

<400> SEQUENCE: 76
cattataatt tccaatgccg tagttc 26

<210> SEQ ID NO 77
<211> LENGTH: 20
<212> TYPE: DNA
<213> ORGANISM: artificial sequence
<220> FEATURE:
<223> OTHER INFORMATION: Primer

<400> SEQUENCE: 77
taagagaggg agaccacgag 20

<210> SEQ ID NO 78
<211> LENGTH: 23
<212> TYPE: DNA
<213> ORGANISM: artificial sequence
<220> FEATURE:
<223> OTHER INFORMATION: Primer

<400> SEQUENCE: 78
cattcgttgt tgttgctggt aag 23

<210> SEQ ID NO 79
<211> LENGTH: 26
<212> TYPE: DNA
<213> ORGANISM: artificial sequence
<220> FEATURE:
<223> OTHER INFORMATION: Primer

<400> SEQUENCE: 79
cttatgaagc taggtaatgg tatgga 26

<210> SEQ ID NO 80
<211> LENGTH: 20
<212> TYPE: DNA
<213> ORGANISM: artificial sequence
<220> FEATURE:
<223> OTHER INFORMATION: Primer

<400> SEQUENCE: 80
catcctcatt gcttgtgtcc 20

<210> SEQ ID NO 81
<211> LENGTH: 19
<212> TYPE: DNA
<213> ORGANISM: artificial sequence
<220> FEATURE:
<223> OTHER INFORMATION: Primer

<400> SEQUENCE: 81
ctctaaaatg ccaaacgcg 19

<210> SEQ ID NO 82
<211> LENGTH: 20
<212> TYPE: DNA
<213> ORGANISM: artificial sequence
<220> FEATURE:
<223> OTHER INFORMATION: Primer

<400> SEQUENCE: 82
gaccctttgg gacttcctcg                                               20

<210> SEQ ID NO 83
<211> LENGTH: 19
<212> TYPE: DNA
<213> ORGANISM: artificial sequence
<220> FEATURE:
<223> OTHER INFORMATION: Primer

<400> SEQUENCE: 83
cgtgttgttt ggtccctcg                                                19

<210> SEQ ID NO 84
<211> LENGTH: 23
<212> TYPE: DNA
<213> ORGANISM: artificial sequence
<220> FEATURE:
<223> OTHER INFORMATION: Primer

<400> SEQUENCE: 84
tgcctcatgt tatttctgtt gcc                                           23

<210> SEQ ID NO 85
<211> LENGTH: 23
<212> TYPE: DNA
<213> ORGANISM: artificial sequence
<220> FEATURE:
<223> OTHER INFORMATION: Primer

<400> SEQUENCE: 85
gattcccgat ttactcctga tgg                                           23

<210> SEQ ID NO 86
<211> LENGTH: 30
<212> TYPE: DNA
<213> ORGANISM: artificial sequence
<220> FEATURE:
<223> OTHER INFORMATION: Primer

<400> SEQUENCE: 86
aacacaaaat acgattactt acttttgtcc                                    30

<210> SEQ ID NO 87
<211> LENGTH: 23
<212> TYPE: DNA
<213> ORGANISM: artificial sequence
<220> FEATURE:
<223> OTHER INFORMATION: Primer

<400> SEQUENCE: 87
tgcctcatgt tatttctgtt gcc                                           23

<210> SEQ ID NO 88
<211> LENGTH: 26
<212> TYPE: DNA
<213> ORGANISM: artificial sequence
<220> FEATURE:
<223> OTHER INFORMATION: Primer

<400> SEQUENCE: 88
gcatgaaatg gatgtagtta tcttgg                                        26

<210> SEQ ID NO 89

<211> LENGTH: 21
<212> TYPE: DNA
<213> ORGANISM: artificial sequence
<220> FEATURE:
<223> OTHER INFORMATION: Primer

<400> SEQUENCE: 89
aaatcgttcg ctctttaccg c 21

<210> SEQ ID NO 90
<211> LENGTH: 22
<212> TYPE: DNA
<213> ORGANISM: artificial sequence
<220> FEATURE:
<223> OTHER INFORMATION: Primer

<400> SEQUENCE: 90
cacaccaaac ttgatcattg tc 22

<210> SEQ ID NO 91
<211> LENGTH: 27
<212> TYPE: DNA
<213> ORGANISM: artificial sequence
<220> FEATURE:
<223> OTHER INFORMATION: Primer

<400> SEQUENCE: 91
attgttgata ttgaatcaga aactttc 27

<210> SEQ ID NO 92
<211> LENGTH: 25
<212> TYPE: DNA
<213> ORGANISM: artificial sequence
<220> FEATURE:
<223> OTHER INFORMATION: Primer

<400> SEQUENCE: 92
tcaataccag tactgttagt ttccg 25

<210> SEQ ID NO 93
<211> LENGTH: 27
<212> TYPE: DNA
<213> ORGANISM: artificial sequence
<220> FEATURE:
<223> OTHER INFORMATION: Primer

<400> SEQUENCE: 93
gcaactgttt cattaacagg cacatcc 27

<210> SEQ ID NO 94
<211> LENGTH: 22
<212> TYPE: DNA
<213> ORGANISM: artificial sequence
<220> FEATURE:
<223> OTHER INFORMATION: Primer

<400> SEQUENCE: 94
attgatgtcg gtggtggtca cg 22

<210> SEQ ID NO 95
<211> LENGTH: 23
<212> TYPE: DNA
<213> ORGANISM: artificial sequence
<220> FEATURE:
<223> OTHER INFORMATION: Primer

<400> SEQUENCE: 95
gcacactgtc tttttcttcc acc 23

<210> SEQ ID NO 96
<211> LENGTH: 28
<212> TYPE: DNA
<213> ORGANISM: artificial sequence
<220> FEATURE:
<223> OTHER INFORMATION: Primer

<400> SEQUENCE: 96
accggaatga gaatgcataa agtaaagg 28

<210> SEQ ID NO 97
<211> LENGTH: 23
<212> TYPE: DNA
<213> ORGANISM: artificial sequence
<220> FEATURE:
<223> OTHER INFORMATION: Primer

<400> SEQUENCE: 97
ccaataccca atcaattaaa ctc 23

<210> SEQ ID NO 98
<211> LENGTH: 29
<212> TYPE: DNA
<213> ORGANISM: artificial sequence
<220> FEATURE:
<223> OTHER INFORMATION: Primer

<400> SEQUENCE: 98
cagtaaattc acacattccg tatcttccc 29

<210> SEQ ID NO 99
<211> LENGTH: 27
<212> TYPE: DNA
<213> ORGANISM: artificial sequence
<220> FEATURE:
<223> OTHER INFORMATION: Primer

<400> SEQUENCE: 99
attgtatagc caaagttgca ggtaggg 27

<210> SEQ ID NO 100
<211> LENGTH: 23
<212> TYPE: DNA
<213> ORGANISM: artificial sequence
<220> FEATURE:
<223> OTHER INFORMATION: Primer

<400> SEQUENCE: 100
agaccgtttg taccgaattc tgc 23

<210> SEQ ID NO 101
<211> LENGTH: 23
<212> TYPE: DNA
<213> ORGANISM: artificial sequence
<220> FEATURE:
<223> OTHER INFORMATION: Primer

<400> SEQUENCE: 101
gcagtgaaag ccatatccaa agc 23

<210> SEQ ID NO 102
<211> LENGTH: 21
<212> TYPE: DNA

<213> ORGANISM: artificial sequence
<220> FEATURE:
<223> OTHER INFORMATION: Primer

<400> SEQUENCE: 102
aaccgtcccc aagatgattc c 21

<210> SEQ ID NO 103
<211> LENGTH: 22
<212> TYPE: DNA
<213> ORGANISM: artificial sequence
<220> FEATURE:
<223> OTHER INFORMATION: Primer

<400> SEQUENCE: 103
tcgttccatt cgtgaagaat gc 22

<210> SEQ ID NO 104
<211> LENGTH: 26
<212> TYPE: DNA
<213> ORGANISM: artificial sequence
<220> FEATURE:
<223> OTHER INFORMATION: Primer

<400> SEQUENCE: 104
gagggtaagc ctcaataaca gactgg 26

<210> SEQ ID NO 105
<211> LENGTH: 25
<212> TYPE: DNA
<213> ORGANISM: artificial sequence
<220> FEATURE:
<223> OTHER INFORMATION: Primer

<400> SEQUENCE: 105
gaaccattaa acacttgagt catgc 25

<210> SEQ ID NO 106
<211> LENGTH: 21
<212> TYPE: DNA
<213> ORGANISM: artificial sequence
<220> FEATURE:
<223> OTHER INFORMATION: Primer

<400> SEQUENCE: 106
ttgatgaacg acaaggaacc g 21

<210> SEQ ID NO 107
<211> LENGTH: 19
<212> TYPE: DNA
<213> ORGANISM: artificial sequence
<220> FEATURE:
<223> OTHER INFORMATION: Primer

<400> SEQUENCE: 107
tcgacagcgc ttacgaacg 19

<210> SEQ ID NO 108
<211> LENGTH: 21
<212> TYPE: DNA
<213> ORGANISM: artificial sequence
<220> FEATURE:
<223> OTHER INFORMATION: Primer

<400> SEQUENCE: 108
caattatcaa agaatcaatg c 21

<210> SEQ ID NO 109
<211> LENGTH: 22
<212> TYPE: DNA
<213> ORGANISM: artificial sequence
<220> FEATURE:
<223> OTHER INFORMATION: Primer

<400> SEQUENCE: 109
tgcaattgaa tttagctcat ct 22

<210> SEQ ID NO 110
<211> LENGTH: 26
<212> TYPE: DNA
<213> ORGANISM: artificial sequence
<220> FEATURE:
<223> OTHER INFORMATION: Primer

<400> SEQUENCE: 110
attcatgatt gtgacctttg taatcc 26

<210> SEQ ID NO 111
<211> LENGTH: 21
<212> TYPE: DNA
<213> ORGANISM: artificial sequence
<220> FEATURE:
<223> OTHER INFORMATION: Primer

<400> SEQUENCE: 111
gacagagggc ccaagttaag g 21

<210> SEQ ID NO 112
<211> LENGTH: 20
<212> TYPE: DNA
<213> ORGANISM: artificial sequence
<220> FEATURE:
<223> OTHER INFORMATION: Primer

<400> SEQUENCE: 112
agcaaaccat tcgtccatcc 20

<210> SEQ ID NO 113
<211> LENGTH: 21
<212> TYPE: DNA
<213> ORGANISM: artificial sequence
<220> FEATURE:
<223> OTHER INFORMATION: Primer

<400> SEQUENCE: 113
tacgacaggt tgctagcttg g 21

<210> SEQ ID NO 114
<211> LENGTH: 24
<212> TYPE: DNA
<213> ORGANISM: artificial sequence
<220> FEATURE:
<223> OTHER INFORMATION: Primer

<400> SEQUENCE: 114
aataatggat cagtcacggc ttcc 24

<210> SEQ ID NO 115
<211> LENGTH: 27
<212> TYPE: DNA
<213> ORGANISM: artificial sequence
<220> FEATURE:

<223> OTHER INFORMATION: Primer

<400> SEQUENCE: 115
aatccatcag attttcaacc agagagg 27

<210> SEQ ID NO 116
<211> LENGTH: 28
<212> TYPE: DNA
<213> ORGANISM: artificial sequence
<220> FEATURE:
<223> OTHER INFORMATION: Primer

<400> SEQUENCE: 116
tgtcagccaa ccattcgtcc atcctaac 28

<210> SEQ ID NO 117
<211> LENGTH: 28
<212> TYPE: DNA
<213> ORGANISM: artificial sequence
<220> FEATURE:
<223> OTHER INFORMATION: Primer

<400> SEQUENCE: 117
ggcttcccgg agatgaccca gattttat 28

<210> SEQ ID NO 118
<211> LENGTH: 38
<212> TYPE: DNA
<213> ORGANISM: artificial sequence
<220> FEATURE:
<223> OTHER INFORMATION: Primer

<400> SEQUENCE: 118
ttgttatttt catgactatt accaccagct tcctctta 38

<210> SEQ ID NO 119
<211> LENGTH: 30
<212> TYPE: DNA
<213> ORGANISM: artificial sequence
<220> FEATURE:
<223> OTHER INFORMATION: Primer

<400> SEQUENCE: 119
agtggaggag gcacaaaagt taggatggac 30

<210> SEQ ID NO 120
<211> LENGTH: 29
<212> TYPE: DNA
<213> ORGANISM: artificial sequence
<220> FEATURE:
<223> OTHER INFORMATION: Primer

<400> SEQUENCE: 120
ccatgtctga taaatacggg tcggtgttc 29

<210> SEQ ID NO 121
<211> LENGTH: 36
<212> TYPE: DNA
<213> ORGANISM: artificial sequence
<220> FEATURE:
<223> OTHER INFORMATION: Primer

<400> SEQUENCE: 121
ttgttgataa ggacgactaa gaataagcag aagata 36

<210> SEQ ID NO 122
<211> LENGTH: 25
<212> TYPE: DNA
<213> ORGANISM: artificial sequence
<220> FEATURE:
<223> OTHER INFORMATION: Primer

<400> SEQUENCE: 122
acgattctgt catcatcatt ttcgc 25

<210> SEQ ID NO 123
<211> LENGTH: 24
<212> TYPE: DNA
<213> ORGANISM: artificial sequence
<220> FEATURE:
<223> OTHER INFORMATION: Primer

<400> SEQUENCE: 123
agtcgtgtat cgttcgctta atgc 24

<210> SEQ ID NO 124
<211> LENGTH: 29
<212> TYPE: DNA
<213> ORGANISM: artificial sequence
<220> FEATURE:
<223> OTHER INFORMATION: Primer

<400> SEQUENCE: 124
catgcctatc tatttcctcc cttgccctc 29

<210> SEQ ID NO 125
<211> LENGTH: 28
<212> TYPE: DNA
<213> ORGANISM: artificial sequence
<220> FEATURE:
<223> OTHER INFORMATION: Primer

<400> SEQUENCE: 125
tgtcagccaa ccattcgtcc atcctaac 28

<210> SEQ ID NO 126
<211> LENGTH: 31
<212> TYPE: DNA
<213> ORGANISM: artificial sequence
<220> FEATURE:
<223> OTHER INFORMATION: Primer

<400> SEQUENCE: 126
tgttcgatca cgttgtctct ttttgccata a 31

<210> SEQ ID NO 127
<211> LENGTH: 38
<212> TYPE: DNA
<213> ORGANISM: artificial sequence
<220> FEATURE:
<223> OTHER INFORMATION: Primer

<400> SEQUENCE: 127
taacaataaa agtactgata atggtggtcg aaggagaa 38

<210> SEQ ID NO 128
<211> LENGTH: 20
<212> TYPE: DNA
<213> ORGANISM: artificial sequence
<220> FEATURE:
<223> OTHER INFORMATION: Primer

<400> SEQUENCE: 128
tattgatgtg gaccagtacc 20

<210> SEQ ID NO 129
<211> LENGTH: 20
<212> TYPE: DNA
<213> ORGANISM: artificial sequence
<220> FEATURE:
<223> OTHER INFORMATION: Primer

<400> SEQUENCE: 129
tgtaactctt ggtcacatgg 20

<210> SEQ ID NO 130
<211> LENGTH: 20
<212> TYPE: DNA
<213> ORGANISM: artificial sequence
<220> FEATURE:
<223> OTHER INFORMATION: Primer

<400> SEQUENCE: 130
cgcgtacttg acatttaacg 20

<210> SEQ ID NO 131
<211> LENGTH: 20
<212> TYPE: DNA
<213> ORGANISM: artificial sequence
<220> FEATURE:
<223> OTHER INFORMATION: Primer

<400> SEQUENCE: 131
ggatcatcgc caaaagaaac 20

<210> SEQ ID NO 132
<211> LENGTH: 27
<212> TYPE: DNA
<213> ORGANISM: artificial sequence
<220> FEATURE:
<223> OTHER INFORMATION: Primer

<400> SEQUENCE: 132
caaagagtca atctgactca agctagc 27

<210> SEQ ID NO 133
<211> LENGTH: 26
<212> TYPE: DNA
<213> ORGANISM: artificial sequence
<220> FEATURE:
<223> OTHER INFORMATION: Primer

<400> SEQUENCE: 133
tgaaatgcct gagatcacta aaatcg 26

<210> SEQ ID NO 134
<211> LENGTH: 28
<212> TYPE: DNA
<213> ORGANISM: artificial sequence
<220> FEATURE:
<223> OTHER INFORMATION: Primer

<400> SEQUENCE: 134
tcaaaccctg ctactaacac ttacttgc 28

<210> SEQ ID NO 135
<211> LENGTH: 24

<212> TYPE: DNA
<213> ORGANISM: artificial sequence
<220> FEATURE:
<223> OTHER INFORMATION: Primer

<400> SEQUENCE: 135
tgtaaagaca cttcattgat gggc 24

<210> SEQ ID NO 136
<211> LENGTH: 31
<212> TYPE: DNA
<213> ORGANISM: artificial sequence
<220> FEATURE:
<223> OTHER INFORMATION: Primer

<400> SEQUENCE: 136
ttcgatttgt gtaaacatta atgatatttg g 31

<210> SEQ ID NO 137
<211> LENGTH: 27
<212> TYPE: DNA
<213> ORGANISM: artificial sequence
<220> FEATURE:
<223> OTHER INFORMATION: Primer

<400> SEQUENCE: 137
gagatgatca agtggtttaa ccattcc 27

<210> SEQ ID NO 138
<211> LENGTH: 18
<212> TYPE: DNA
<213> ORGANISM: artificial sequence
<220> FEATURE:
<223> OTHER INFORMATION: Primer

<400> SEQUENCE: 138
cgagtgccca tgcagtgg 18

<210> SEQ ID NO 139
<211> LENGTH: 26
<212> TYPE: DNA
<213> ORGANISM: artificial sequence
<220> FEATURE:
<223> OTHER INFORMATION: Primer

<400> SEQUENCE: 139
aataaaaatc caacaatggc agatcc 26

<210> SEQ ID NO 140
<211> LENGTH: 24
<212> TYPE: DNA
<213> ORGANISM: artificial sequence
<220> FEATURE:
<223> OTHER INFORMATION: Primer

<400> SEQUENCE: 140
atgctgttga tgctttaaac tggg 24

<210> SEQ ID NO 141
<211> LENGTH: 28
<212> TYPE: DNA
<213> ORGANISM: artificial sequence
<220> FEATURE:
<223> OTHER INFORMATION: Primer

<400> SEQUENCE: 141

-continued ggttaatcga gagatgtttt gtggtagg 28

<210> SEQ ID NO 142
<211> LENGTH: 23
<212> TYPE: DNA
<213> ORGANISM: artificial sequence
<220> FEATURE:
<223> OTHER INFORMATION: Primer

<400> SEQUENCE: 142
cgatgacaca gagcaagaac gac 23

<210> SEQ ID NO 143
<211> LENGTH: 23
<212> TYPE: DNA
<213> ORGANISM: artificial sequence
<220> FEATURE:
<223> OTHER INFORMATION: Primer

<400> SEQUENCE: 143
cgcgggtata tgtgtagcaa tcg 23

<210> SEQ ID NO 144
<211> LENGTH: 17
<212> TYPE: DNA
<213> ORGANISM: artificial sequence
<220> FEATURE:
<223> OTHER INFORMATION: Primer

<400> SEQUENCE: 144
cggcaacgcc agttccc 17

<210> SEQ ID NO 145
<211> LENGTH: 26
<212> TYPE: DNA
<213> ORGANISM: artificial sequence
<220> FEATURE:
<223> OTHER INFORMATION: Primer

<400> SEQUENCE: 145
ctaacaggca aacaataaca ggttgc 26

<210> SEQ ID NO 146
<211> LENGTH: 24
<212> TYPE: DNA
<213> ORGANISM: artificial sequence
<220> FEATURE:
<223> OTHER INFORMATION: Primer

<400> SEQUENCE: 146
ggaagatgtg agccacctta aagc 24

<210> SEQ ID NO 147
<211> LENGTH: 26
<212> TYPE: DNA
<213> ORGANISM: artificial sequence
<220> FEATURE:
<223> OTHER INFORMATION: Primer

<400> SEQUENCE: 147
aaaggtactg acagaaagag cttgcc 26

<210> SEQ ID NO 148
<211> LENGTH: 23
<212> TYPE: DNA
<213> ORGANISM: artificial sequence
<220> FEATURE:
<223> OTHER INFORMATION: Primer

<400> SEQUENCE: 148
agatacactg ggaggaggat ggg 23

<210> SEQ ID NO 149
<211> LENGTH: 22
<212> TYPE: DNA
<213> ORGANISM: artificial sequence
<220> FEATURE:
<223> OTHER INFORMATION: Primer

<400> SEQUENCE: 149
cggcaaaatt cattccttga gc 22

<210> SEQ ID NO 150
<211> LENGTH: 24
<212> TYPE: DNA
<213> ORGANISM: artificial sequence
<220> FEATURE:
<223> OTHER INFORMATION: Primer

<400> SEQUENCE: 150
aacatatagc caaaggactc ttcg 24

<210> SEQ ID NO 151
<211> LENGTH: 20
<212> TYPE: DNA
<213> ORGANISM: artificial sequence
<220> FEATURE:
<223> OTHER INFORMATION: Primer

<400> SEQUENCE: 151
aggatacaca atgacccaac 20

<210> SEQ ID NO 152
<211> LENGTH: 27
<212> TYPE: DNA
<213> ORGANISM: artificial sequence
<220> FEATURE:
<223> OTHER INFORMATION: Primer

<400> SEQUENCE: 152
ttttatcgac cttgaggaac aattagg 27

<210> SEQ ID NO 153
<211> LENGTH: 20
<212> TYPE: DNA
<213> ORGANISM: artificial sequence
<220> FEATURE:
<223> OTHER INFORMATION: Primer

<400> SEQUENCE: 153
tgttcactag gtggaaagag 20

<210> SEQ ID NO 154
<211> LENGTH: 26
<212> TYPE: DNA
<213> ORGANISM: artificial sequence
<220> FEATURE:
<223> OTHER INFORMATION: Primer

<400> SEQUENCE: 154
agtacaatac cgagaaatcc gacaag 26

<210> SEQ ID NO 155
<211> LENGTH: 27
<212> TYPE: DNA
<213> ORGANISM: artificial sequence
<220> FEATURE:
<223> OTHER INFORMATION: Primer

<400> SEQUENCE: 155
gctcaattaa tggaacagta gttaccc 27

<210> SEQ ID NO 156
<211> LENGTH: 19
<212> TYPE: DNA
<213> ORGANISM: artificial sequence
<220> FEATURE:
<223> OTHER INFORMATION: Primer

<400> SEQUENCE: 156
cgtgttgttt ggtccctcg 19

<210> SEQ ID NO 157
<211> LENGTH: 23
<212> TYPE: DNA
<213> ORGANISM: Artificial Sequence
<220> FEATURE:
<223> OTHER INFORMATION: Primer

<400> SEQUENCE: 157
gcacactgtc tttttcttcc acc 23

<210> SEQ ID NO 158
<211> LENGTH: 27
<212> TYPE: DNA
<213> ORGANISM: Artificial Sequence
<220> FEATURE:
<223> OTHER INFORMATION: Primer

<400> SEQUENCE: 158
gcaactgttt cattaacagg cacatcc 27

<210> SEQ ID NO 159
<211> LENGTH: 24
<212> TYPE: DNA
<213> ORGANISM: artificial sequence
<220> FEATURE:
<223> OTHER INFORMATION: Primer

<400> SEQUENCE: 159
gccagcgcta atacaaggat gtgg 24

<210> SEQ ID NO 160
<211> LENGTH: 23
<212> TYPE: DNA
<213> ORGANISM: artificial sequence
<220> FEATURE:
<223> OTHER INFORMATION: Primer

<400> SEQUENCE: 160
gcagtgaaag ccatatccaa agc 23

<210> SEQ ID NO 161
<211> LENGTH: 22
<212> TYPE: DNA
<213> ORGANISM: artificial sequence
<220> FEATURE:
<223> OTHER INFORMATION: Primer

<400> SEQUENCE: 161
tcgttccatt cgtgaagaat gc 22

<210> SEQ ID NO 162
<211> LENGTH: 23
<212> TYPE: DNA
<213> ORGANISM: artificial sequence
<220> FEATURE:
<223> OTHER INFORMATION: Primer

<400> SEQUENCE: 162
gctacgaaag ataatggtgc agc 23

<210> SEQ ID NO 163
<211> LENGTH: 20
<212> TYPE: DNA
<213> ORGANISM: artificial sequence
<220> FEATURE:
<223> OTHER INFORMATION: Primer

<400> SEQUENCE: 163
agcaaaccat tcgtccatcc 20

<210> SEQ ID NO 164
<211> LENGTH: 24
<212> TYPE: DNA
<213> ORGANISM: artificial sequence
<220> FEATURE:
<223> OTHER INFORMATION: Primer

<400> SEQUENCE: 164
atgtggaaaa cggtaagcaa gtgg 24

<210> SEQ ID NO 165
<211> LENGTH: 25
<212> TYPE: DNA
<213> ORGANISM: artificial sequence
<220> FEATURE:
<223> OTHER INFORMATION: Primer

<400> SEQUENCE: 165
acgattctgt catcatcatt ttcgc 25

<210> SEQ ID NO 166
<211> LENGTH: 26
<212> TYPE: DNA
<213> ORGANISM: artificial sequence
<220> FEATURE:
<223> OTHER INFORMATION: Primer

<400> SEQUENCE: 166
tgaaatgcct gagatcacta aaatcg 26

<210> SEQ ID NO 167
<211> LENGTH: 27
<212> TYPE: DNA
<213> ORGANISM: artificial sequence
<220> FEATURE:
<223> OTHER INFORMATION: Primer

<400> SEQUENCE: 167
ggaatggtta aaccacttga tcatctc 27

<210> SEQ ID NO 168

<211> LENGTH: 27
<212> TYPE: DNA
<213> ORGANISM: artificial sequence
<220> FEATURE:
<223> OTHER INFORMATION: Primer

<400> SEQUENCE: 168
atgccagttt aagagcaata gaaatgg 27

<210> SEQ ID NO 169
<211> LENGTH: 17
<212> TYPE: DNA
<213> ORGANISM: artificial sequence
<220> FEATURE:
<223> OTHER INFORMATION: Primer

<400> SEQUENCE: 169
gggaactggc gttgccg 17

<210> SEQ ID NO 170
<211> LENGTH: 23
<212> TYPE: DNA
<213> ORGANISM: artificial sequence
<220> FEATURE:
<223> OTHER INFORMATION: Primer

<400> SEQUENCE: 170
gaagatgtga gccaccttaa agc 23

<210> SEQ ID NO 171
<211> LENGTH: 22
<212> TYPE: DNA
<213> ORGANISM: artificial sequence
<220> FEATURE:
<223> OTHER INFORMATION: Primer

<400> SEQUENCE: 171
gctcaaggaa tgaattttgc cg 22

<210> SEQ ID NO 172
<211> LENGTH: 21
<212> TYPE: DNA
<213> ORGANISM: artificial sequence
<220> FEATURE:
<223> OTHER INFORMATION: Primer

<400> SEQUENCE: 172
gttgacgcag gaagcttttg c 21

<210> SEQ ID NO 173
<211> LENGTH: 25
<212> TYPE: DNA
<213> ORGANISM: artificial sequence
<220> FEATURE:
<223> OTHER INFORMATION: Primer

<400> SEQUENCE: 173
ggaacataag atttaactcc gcctc 25

<210> SEQ ID NO 174
<211> LENGTH: 34
<212> TYPE: DNA
<213> ORGANISM: artificial sequence
<220> FEATURE:
<223> OTHER INFORMATION: Primer

<400> SEQUENCE: 174
aaactcgaga agcttggtca taatcatcaa tcag 34

<210> SEQ ID NO 175
<211> LENGTH: 31
<212> TYPE: DNA
<213> ORGANISM: artificial sequence
<220> FEATURE:
<223> OTHER INFORMATION: Primer

<400> SEQUENCE: 175
aaaggtaccc atgtactact acatcatctc c 31

<210> SEQ ID NO 176
<211> LENGTH: 33
<212> TYPE: DNA
<213> ORGANISM: artificial sequence
<220> FEATURE:
<223> OTHER INFORMATION: Primer

<400> SEQUENCE: 176
aaactcgaga agcttgtgta actaagccag cgc 33

<210> SEQ ID NO 177
<211> LENGTH: 27
<212> TYPE: DNA
<213> ORGANISM: artificial sequence
<220> FEATURE:
<223> OTHER INFORMATION: Primer

<400> SEQUENCE: 177
aaaggtacca cttgaatata tcaccgc 27

<210> SEQ ID NO 178
<211> LENGTH: 29
<212> TYPE: DNA
<213> ORGANISM: artificial sequence
<220> FEATURE:
<223> OTHER INFORMATION: Primer

<400> SEQUENCE: 178
aaaggatcct ttgagtaatg gtgaaaaga 29

<210> SEQ ID NO 179
<211> LENGTH: 30
<212> TYPE: DNA
<213> ORGANISM: artificial sequence
<220> FEATURE:
<223> OTHER INFORMATION: Primer

<400> SEQUENCE: 179
aaaggtacca acatctactc tcgaggattg 30

<210> SEQ ID NO 180
<211> LENGTH: 33
<212> TYPE: DNA
<213> ORGANISM: artificial sequence
<220> FEATURE:
<223> OTHER INFORMATION: Primer

<400> SEQUENCE: 180
aaactcgaga agctttagga gggtatgtcc ggc 33

<210> SEQ ID NO 181
<211> LENGTH: 28
<212> TYPE: DNA

<213> ORGANISM: artificial sequence
<220> FEATURE:
<223> OTHER INFORMATION: Primer

<400> SEQUENCE: 181
aaaggtacct taactccgcc tcggctcc 28

<210> SEQ ID NO 182
<211> LENGTH: 27
<212> TYPE: DNA
<213> ORGANISM: artificial sequence
<220> FEATURE:
<223> OTHER INFORMATION: Primer

<400> SEQUENCE: 182
aaaggatcct tcagttcatt catggcg 27

<210> SEQ ID NO 183
<211> LENGTH: 33
<212> TYPE: DNA
<213> ORGANISM: artificial sequence
<220> FEATURE:
<223> OTHER INFORMATION: Primer

<400> SEQUENCE: 183
aaaggtaccg ttcatagtaa ataataacag gcg 33

<210> SEQ ID NO 184
<211> LENGTH: 37
<212> TYPE: DNA
<213> ORGANISM: artificial sequence
<220> FEATURE:
<223> OTHER INFORMATION: Primer

<400> SEQUENCE: 184
aaactcgaga agcttatgat catgagtaac ttatgga 37

<210> SEQ ID NO 185
<211> LENGTH: 28
<212> TYPE: DNA
<213> ORGANISM: artificial sequence
<220> FEATURE:
<223> OTHER INFORMATION: Primer

<400> SEQUENCE: 185
aaaggtaccc caacaggcca ttccgttg 28

<210> SEQ ID NO 186
<211> LENGTH: 30
<212> TYPE: DNA
<213> ORGANISM: artificial sequence
<220> FEATURE:
<223> OTHER INFORMATION: Primer

<400> SEQUENCE: 186
aaaggatcct ggcagatcct tatgaattcc 30

<210> SEQ ID NO 187
<211> LENGTH: 32
<212> TYPE: DNA
<213> ORGANISM: artificial sequence
<220> FEATURE:
<223> OTHER INFORMATION: Primer

<400> SEQUENCE: 187
aaaggtacct tatgatagga agcagcttat tc 32

<210> SEQ ID NO 188
<211> LENGTH: 30
<212> TYPE: DNA
<213> ORGANISM: artificial sequence
<220> FEATURE:
<223> OTHER INFORMATION: Primer

<400> SEQUENCE: 188
aaaggatccg aaattgacga gacaatatgg 30

<210> SEQ ID NO 189
<211> LENGTH: 32
<212> TYPE: DNA
<213> ORGANISM: artificial sequence
<220> FEATURE:
<223> OTHER INFORMATION: Primer

<400> SEQUENCE: 189
aaaggtaccc attcaaaaac gaatatgtgt gc 32

<210> SEQ ID NO 190
<211> LENGTH: 31
<212> TYPE: DNA
<213> ORGANISM: artificial sequence
<220> FEATURE:
<223> OTHER INFORMATION: Primer

<400> SEQUENCE: 190
aaaggatccc ctaagagaga tcctccaact g 31

<210> SEQ ID NO 191
<211> LENGTH: 36
<212> TYPE: DNA
<213> ORGANISM: artificial sequence
<220> FEATURE:
<223> OTHER INFORMATION: Primer

<400> SEQUENCE: 191
aaaggtacca atacaagtat gaaaacaaga gaataa 36

<210> SEQ ID NO 192
<211> LENGTH: 22
<212> TYPE: DNA
<213> ORGANISM: artificial sequence
<220> FEATURE:
<223> OTHER INFORMATION: Primer

<400> SEQUENCE: 192
gaggtgttca ttgccatgtc aa 22

<210> SEQ ID NO 193
<211> LENGTH: 22
<212> TYPE: DNA
<213> ORGANISM: artificial sequence
<220> FEATURE:
<223> OTHER INFORMATION: Primer

<400> SEQUENCE: 193
gtttcgcaag ctcctgcata gt 22

<210> SEQ ID NO 194
<211> LENGTH: 39
<212> TYPE: DNA
<213> ORGANISM: Artificial Sequence
<220> FEATURE:

```
<223> OTHER INFORMATION: Primer
<220> FEATURE:
<221> NAME/KEY: misc_feature
<222> LOCATION: (12)..(12)
<223> OTHER INFORMATION: R = A or G;
<220> FEATURE:
<221> NAME/KEY: misc_feature
<222> LOCATION: (38)..(38)
<223> OTHER INFORMATION: V = A,  C or G
<220> FEATURE:
<221> NAME/KEY: misc_feature
<222> LOCATION: (39)..(39)
<223> OTHER INFORMATION: N = A/T or C/G

<400> SEQUENCE: 194

attctagatc cracatgttt tttttttttt tttttttvn                                    39
```

BIOSYNTHESIS OF OPIATE ALKALOIDS

CROSS REFERENCE TO RELATED APPLICATIONS

This is the U.S. National Stage of International Application No. PCT/GB2013/050599, filed Mar. 12, 2013, which was published in English under PCT Article 21(2), which in turn claims the benefit of Great Britain Patent Application No. 1204407.09, filed Mar. 13, 2012.

INTRODUCTION

This disclosure relates to the isolation and sequencing of a nucleic acid molecule that includes a gene cluster comprising 10 genes from a noscapine producing *Papaver somniferum* [opium poppy] cultivar; transgenic cells transformed with said nucleic acid molecule, sequence variants of the genes; the use of said genes/proteins in the production of opiate alkaloids; and the use of the genes as a marker of *P. somniferum* plants that synthesize opiate alkaloids, in particular noscapine.

BACKGROUND TO DISCLOSURE

Noscapine belongs to the phthalideisoquinoline subclass of the structurally diverse isoquinoline alkaloids whereas codeine, morphine, thebaine and oripavine belong to the morphinan subclass. While the biosynthesis of morphinans has been elucidated at the molecular level our knowledge of noscapine biosynthesis has not advanced significantly since the demonstration using isotope labeling in the 1960s, that it is derived from scoulerine. Understanding the biochemical genetics underpinning noscapine biosynthesis should enable improved production of noscapine and related molecules both in poppy and other expression systems.

*P. somniferum* is the plant from which opium is extracted. The opium poppy is the only commercially exploited poppy of the family Papaveraceae and is the principal source of natural opiates. The opium is extracted from latex harvested from the green seed pods. A further source of opiate alkaloids is the poppy straw which is the dried mature plant. *P. somniferum* is a source of clinically useful opiate alkaloids such as morphine, codeine, thebaine, noscapine [also known as narcotine] and papaverine. The clinical application of these opiate alkaloids and their derivates is broad having use as analgesics, cough suppressants and anti-spasmodics. Although not used as a pharmacological agent in its own right, thebaine is a particularly useful opiate which can be converted into a range of compounds such as hydrocodone, oxycodone, oxymorphone, nalbuphine naltrexone, buprenorphine and etorphine. These intermediates also have broad pharmaceutical applications. For example, oxycodone, oxymorphone and etorphine are widely used as an analgesic for moderate to severe pain and are often combined with other analgesics such as ibuprofen. Buprenorphine is used in the treatment of heroin addiction and chronic pain. Naltrexone is used in the treatment of alcohol and opiate addiction.

This disclosure relates to transcriptomic analysis of *P. somniferum* noscapine producing cultivars compared to *P. somniferum* cultivars that are non-noscapine producing. The analysis has revealed the exclusive expression of a group of mostly cytochrome P450 and methyltransferase genes in a poppy variety that produces noscapine. These genes are surprisingly absent from the genomes of two non-noscapine producing varieties. Analysis of an F2 mapping population indicated the genes are tightly linked in the noscapine variety and bacterial artificial chromosome sequencing confirmed they exist as a novel gene cluster for the biosynthesis of opiate alkaloids.

STATEMENTS OF INVENTION

According to an aspect of the invention there is provided an isolated nucleic acid molecule that encodes at least two polypeptides wherein the two polypeptides are selected from the group consisting of a nucleic acid molecule comprising or consisting of a nucleotide sequence selected from:

i) a nucleotide sequence as represented by the sequence in SEQ ID NO: 1, 2, 3, 4, 5, 6, 7, 8, 9 or 10;

ii) a nucleotide sequence wherein said sequence is degenerate as a result of the genetic code to the nucleotide sequence defined in (i);

iii) a nucleic acid molecule the complementary strand of which hybridizes under stringent hybridization conditions to the sequence in SEQ ID NO: 1, 2, 3, 4, 5, 6, 7, 8, 9 or 10 wherein said nucleic acid molecule encodes polypeptides involved in the biosynthesis of *P. somniferum* opiate alkaloids or intermediates in the biosynthesis of opiate alkaloids;

iv) a nucleotide sequence that encodes a polypeptide comprising an amino acid sequence as represented in SEQ ID NO: 11, 12, 13, 14, 15, 16, 17, 18, 19 or 20;

v) a nucleotide sequence that encodes a polypeptide comprising an amino acid sequence wherein said amino acid sequence is modified by addition deletion or substitution of at least one amino acid residue as represented in iv) above and which has retained or enhanced opiate alkaloid biosynthetic activity.

According to a further aspect of the invention there is provided an isolated nucleic acid molecule that comprises a gene cluster that encodes two or more polypeptides involved in the biosynthesis of opiate alkaloids or intermediates, wherein one of said two genes comprises a nucleotide sequence selected from the group consisting of:

i) a nucleotide sequence as set forth in SEQ ID NO: 8;

ii) a nucleotide sequence wherein said sequence is degenerate as a result of the genetic code to the nucleotide sequence defined in (i);

iii) a nucleic acid molecule the complementary strand of which hybridizes under stringent hybridization conditions to the nucleotide sequence in SEQ ID NO: 8 and which encodes a polypeptide that has carboxylesterase activity; and iv) a nucleotide sequence that encodes a polypeptide comprising an amino acid sequence as set forth in SEQ ID NO: 18 or a nucleotide sequence that encodes a polypeptide that has 46% amino acid sequence identity across the full length amino acid sequence set forth in SEQ ID NO: 18 wherein said polypeptide has carboxylesterase activity.

According to a further aspect or embodiment of the invention there is provided an isolated nucleic acid molecule that comprises a gene cluster that encodes two or more polypeptides involved in the biosynthesis of opiate alkaloids or intermediates, wherein one of said two genes comprises a nucleotide sequence selected from the group consisting of;

i) a nucleotide sequence as set forth in SEQ ID NO: 9;

ii) a nucleotide sequence wherein said sequence is degenerate as a result of the genetic code to the nucleotide sequence defined in (i);

iii) a nucleic acid molecule the complementary strand of which hybridizes under stringent hybridization conditions to the sequence in SEQ ID NO: 9 and which encodes a polypeptide that has short-chain dehydrogenase/reductase activity; and iv) a nucleotide sequence that encodes a polypeptide comprising an amino acid sequence as set forth in SEQ ID NO: 19 or a nucleotide sequence that encodes a polypeptide that has is 46% amino acid sequence identity across the full length amino acid sequence set forth in SEQ ID NO: 19 wherein said polypeptide has short-chain dehydrogenase/reductase activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Allows Sequences that Share at Least 80% Identity to Hybridize)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Allows Sequences that Share at Least 50% Identity to Hybridize)

Hybridization: 6×SSC at RT to 55° C. for 16-20 hours

Wash at least twice: 2×-3×SSC at RT to 55° C. for 20-30 minutes each.

In a preferred embodiment of the invention said nucleic acid molecule comprises or consists of a nucleotide sequence as represented SEQ ID NO: 1 wherein said nucleic acid molecule encodes a polypeptide with methyl transferase activity.

In a preferred embodiment of the invention said nucleic acid molecule comprises or consists of a nucleotide sequence as represented SEQ ID NO: 2 wherein said nucleic acid molecule encodes a polypeptide with methyl transferase activity.

In a preferred embodiment of the invention said nucleic acid molecule comprises or consists of a nucleotide sequence as represented SEQ ID NO: 3 wherein said nucleic acid molecule encodes a polypeptide with methyl transferase activity.

In a preferred embodiment of the invention said nucleic acid molecule comprises or consists of a nucleotide sequence as represented SEQ ID NO: 4 wherein said nucleic acid molecule encodes a polypeptide with cytochrome P450 activity.

In a preferred embodiment of the invention said nucleic acid molecule comprises or consists of a nucleotide sequence as represented SEQ ID NO: 5 wherein said nucleic acid molecule encodes a polypeptide with cytochrome P450 activity.

In a preferred embodiment of the invention said nucleic acid molecule comprises or consists of a nucleotide sequence as represented SEQ ID NO: 6 wherein said nucleic acid molecule encodes a polypeptide with cytochrome P450 activity.

In a preferred aspect or embodiment of the invention said nucleic acid molecule comprises or consists of a nucleotide sequence as represented SEQ ID NO: 7 wherein said nucleic acid molecule encodes a polypeptide with cytochrome P450 activity.

In a preferred aspect or embodiment of the invention said nucleic acid molecule comprises or consists of a nucleotide sequence as represented SEQ ID NO: 8 wherein said nucleic acid molecule encodes a polypeptide with carboxylesterase activity.

In a preferred aspect or embodiment of the invention said nucleic acid molecule comprises or consists of a nucleotide sequence as represented SEQ ID NO: 9 wherein said nucleic acid molecule encodes a polypeptide with short-chain dehydrogenase/reductase activity.

In a preferred aspect or embodiment of the invention said nucleic acid molecule comprises or consists of a nucleotide sequence as represented SEQ ID NO: 10 wherein said nucleic acid molecule encodes a polypeptide with acetyltransferase activity.

In a preferred embodiment of the invention said nucleic acid molecule includes SEQ ID NO: 1 and further includes one or more nucleotide sequences selected from the group consisting of: SEQ ID NO: 2, 3, 4, 5, 6, 7, 8, 9 or 10.

In a preferred embodiment of the invention said nucleic acid molecule includes 3, 4, 5, 6, 7, 8 or 9 nucleotide sequences selected from the group consisting of: SEQ ID NO: 1, 2, 3, 4, 5, 6, 7, 8, 9 or 10.

In a preferred embodiment of the invention said nucleic acid molecule includes each of the nucleotide sequences as represented in SEQ ID NO: 1, 2, 3, 4, 5, 6, 7, 8, 9 and 10.

According to a further aspect of the invention there is provided an isolated polypeptide selected from the group consisting of:

i) a polypeptide comprising or consisting of an amino acid sequence as represented in SEQ ID NO: 17; or ii) a modified polypeptide comprising or consisting of a modified amino acid sequence wherein said polypeptide is modified by addition deletion or substitution of at least one amino acid residue of the sequence presented in SEQ ID NO: 17 and which has retained or enhanced cytochrome P450 activity.

In a preferred embodiment of the invention said polypeptide comprises or consists of an amino acid sequence that is at least 55% identical to the full length amino acid sequence in SEQ ID NO: 17 and which encodes a polypeptide with cytochrome P450 activity.

According to a further aspect of the invention there is provided an isolated polypeptide selected from the group consisting of:

i) a polypeptide comprising or consisting of an amino acid sequence as represented in SEQ ID NO:18; or ii) a modified polypeptide comprising or consisting of a modified amino acid sequence wherein said polypeptide is modified by addition deletion or substitution of at least one amino acid residue of the sequence presented in SEQ ID NO: 18 and which has retained or enhanced carboxylesterase activity.

In a preferred embodiment of the invention said polypeptide comprises or consists of an amino acid sequence that is at least 46% identical to the full length amino acid sequence in SEQ ID NO: 18 and which encodes a polypeptide with carboxylesterase activity.

According to a further aspect of the invention there is provided an isolated polypeptide selected from the group consisting of:

i) a polypeptide comprising or consisting of an amino acid sequence as represented in SEQ ID NO: 19; or ii) a modified polypeptide comprising or consisting of a modified amino acid sequence wherein said polypeptide is modified by addition deletion or substitution of at least one amino acid residue of the sequence presented in SEQ ID NO: 19 and which has retained or enhanced short-chain dehydrogenase/reductase activity.

In a preferred embodiment of the invention said polypeptide comprises or consists of an amino acid sequence that is at least 47% identical to the full length amino acid sequence in SEQ ID NO: 19 and which encodes a polypeptide with short-chain dehydrogenase/reductase activity.

According to a further aspect of the invention there is provided an isolated polypeptide selected from the group consisting of:

i) a polypeptide comprising or consisting of an amino acid sequence as represented in SEQ ID NO: 20; or ii) a modified polypeptide comprising or consisting of a modified amino acid sequence wherein said polypeptide is modified by addition deletion or substitution of at least one amino acid residue of the sequence presented in SEQ ID NO: 20 and which has retained or enhanced acetyltransferase activity.

In a preferred embodiment of the invention said polypeptide comprises or consists of an amino acid sequence that is at least 67% identical to the full length amino acid sequence in SEQ ID NO: 20 and which encodes a polypeptide with acetyltransferase activity.

A modified polypeptide as herein disclosed may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In one embodiment, the variant polypeptides have at least 39% to 50% identity, even more preferably at least 55% identity, still more preferably at least 60%, 65%, 70%, 75%, 80%, 85%, 90%, 95% identity, and at least 99% identity with most or the full length amino acid sequence illustrated herein.

According to an aspect of the invention there is provided an isolated nucleic acid molecule comprising or consisting of a nucleotide sequence selected from the group consisting of:

i) a nucleotide sequence as represented by the sequence in SEQ ID NO: 7, 8, 9 or 10;

ii) a nucleotide sequence wherein said sequence is degenerate as a result of the genetic code to the nucleotide sequence defined in (i);

iii) a nucleic acid molecule the complementary strand of which hybridizes under stringent hybridization conditions to the sequence in SEQ ID NO: 7, 8, 9 or 10 wherein said nucleic acid molecule encodes polypeptides involved in the biosynthesis of *P. somniferum* opiate alkaloids or intermediates in the biosynthesis of opiate alkaloids;

iv) a nucleotide sequence that encodes a polypeptide comprising an amino acid sequence as represented in SEQ ID NO: 17, 18, 19 or 20;

v) a nucleotide sequence that encodes a polypeptide comprising an amino acid sequence wherein said amino acid sequence is modified by addition deletion or substitution of at least one amino acid residue as represented in iv) above and which has retained or enhanced opiate alkaloid biosynthetic activity.

According to a further aspect of the invention there is provided a vector comprising a nucleic acid molecule according to the invention.

Preferably the nucleic acid molecule in the vector is under the control of, and operably linked to, an appropriate promoter or other regulatory elements for transcription in a host cell such as a microbial, (e.g. bacterial, yeast), or plant cell. The vector may be a bi -functional expression vector which functions in multiple hosts. In the case of genomic DNA this may contain its own promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18 (675-689); pEMU (Last et al. (1991) Theor Appl. Genet. 81: 581-588); MAS (Velten et al. (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142, each of which is incorporated by reference.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc.

Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is a tissue specific promoter, an inducible promoter or a developmentally regulated promoter.

Particular of interest in the present context are nucleic acid constructs which operate as plant vectors. Specific procedures and vectors previously used with wide success in plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP194809). If desired, selectable genetic markers may be included in the construct, such as those that confer selectable phenotypes such as resistance to herbicides (e.g. kanamycin, hygromycin, phosphinotricin, chlorsulfuron, methotrexate, gentamycin, spectinomycin, imidazolinones and glyphosate).

In a preferred embodiment of the invention said vector is a bacterial artificial chromosome [BACS].

According to a further aspect of the invention there is provided a transgenic cell transformed or transfected with a nucleic acid molecule or vector according to the invention.

In a preferred embodiment of the invention said cell is a plant cell.

In a preferred embodiment of the invention said plant cell is from the genus *Papaver.*

In a preferred embodiment of the invention said plant cell is a *Papaver somniferum* cell.

According to a further aspect of the invention there is provided a plant comprising a plant cell according to the invention.

In a preferred embodiment of the invention said plant is from the genus *Papaver*; preferably *Papaver somniferum.*

In an alternative preferred embodiment of the invention said cell is a microbial cell; preferably a bacterial or fungal cell [e.g. yeast, *Saccharomyces cerevisae].*

In a preferred embodiment of the invention said cell is adapted such that the nucleic acid molecule encoding one or more polypeptides according to the invention is over-expressed when compared to a non-transgenic cell of the same species.

According to a further aspect of the invention there is provided a nucleic acid molecule comprising a transcription cassette wherein said cassette includes a nucleotide sequence designed with reference to a nucleotide sequence selected from the group: SEQ ID NO: 1, 2, 3, 4, 5, 6, 7, 8, 9 or 10, and is adapted for expression by provision of at least one promoter operably linked to said nucleotide sequence such that both sense and antisense molecules are transcribed from said cassette.

In a preferred embodiment of the invention said cassette is adapted such that both sense and antisense ribonucleic acid molecules are transcribed from said cassette wherein said sense and antisense nucleic acid molecules are adapted to anneal over at least part or all of their length to form a inhibitory RNA or short hairpin RNA.

In a preferred embodiment of the invention said cassette is provided with at least two promoters adapted to transcribe both sense and antisense strands of said ribonucleic acid molecule.

In an alternative preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces an ribonucleic acid molecule which forms a double stranded region by complementary base pairing of said first and second parts thereby forming an short hairpin RNA.

A technique to specifically ablate gene function is through the introduction of double stranded RNA, also referred to as small inhibitory/interfering RNA (siRNA) or short hairpin RNA [shRNA], into a cell which results in the destruction of mRNA complementary to the sequence included in the siRNA/shRNA molecule. The siRNA molecule comprises two complementary strands of RNA (a sense strand and an antisense strand) annealed to each other to form a double stranded RNA molecule. The siRNA molecule is typically derived from exons of the gene which is to be ablated. The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

In a preferred embodiment of the invention said nucleic acid molecule is part of a vector adapted for expression in a plant cell.

According to a further aspect of the invention there is provided a plant cell transfected with a nucleic acid molecule or vector according to the invention wherein said cell has reduced expression of a polypeptide according to the invention.

According to an aspect of the invention there is provided a process for the modification of one or more opiate alkaloids comprising:

i) providing a transgenic plant cell according to the invention;

ii) cultivating said plant cell to produce a transgenic plant; and optionally i) harvesting said transgenic plant, or part thereof.

In a preferred method of the invention said harvested plant material is dried and opiate alkaloid is extracted.

According to an alternative aspect of the invention there is provided a process for the modification of one or more opiate alkaloids or opiate alkaloid intermediate metabolites comprising:

i) providing a transgenic microbial cell according to the invention that expresses one or more nucleic acid molecules according to the invention in culture with at least one opiate alkaloid or opiate alkaloid intermediate metabolite;

ii) cultivating the microbial cell under conditions that modify one or more opitate alkaloid or opiate alkaloid intermediate; and optionally iii) isolating said opiate alkaloid or opiate alkaloid intermediate from the microbial cell or cell culture.

In a preferred method of the invention said microbial cell is a bacterial cell or fungal/yeast cell.

If microbial cells are used as organisms in the process according to the invention they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The methylated opiate alkaloids produced can be isolated from the organisms as described above by processes known to the skilled worker, for example by extraction, distillation, crystallization, if appropriate precipitation with salt, and/or chromatography. To this end, the organisms can advantageously be disrupted beforehand. In this process, the pH value is advantageously kept between pH 4 and 12, preferably between pH 6 and 9, especially preferably between pH 7 and 8.

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassium hydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the opiate alkaloids present therein.

According to a further aspect of the invention there is provided the use of a gene encoded by a nucleic acid molecule as represented by the nucleic acid sequence in SEQ ID NO: 1, 2, 3, 4, 5, 6, 7, 8, 9 or 10, or a nucleic acid molecule that hybridizes under stringent hybridization conditions to the nucleotide sequence in SEQ ID NO: 1, 2, 3, 4, 5, 6, 7, 8, 9 or 10 and encodes a polypeptide with opiate alkaloid biosynthetic activity as a means to identify a locus wherein said locus is associated with altered expression or activity of said opiate alkaloid biosynthetic activity.

Mutagenesis as a means to induce phenotypic changes in organisms is well known in the art and includes but is not limited to the use of mutagenic agents such as chemical mutagens [e.g. base analogues, deaminating agents, DNA intercalating agents, alkylating agents, transposons, bromine, sodium azide] and physical mutagens [e.g. ionizing radiation, psoralen exposure combined with UV irradiation].

According to a further aspect of the invention there is provided a method to produce a *P. somniferum* plant that has altered expression of a polypeptide according to the invention comprising the steps of:

- i) mutagenesis of wild-type seed from a *P. somniferum* plant that does express said polypeptide;
- ii) cultivation of the seed in i) to produce first and subsequent generations of plants;
- iii) obtaining seed from the first generation plant and subsequent generations of plants;
- iv) determining if the seed from said first and subsequent generations of plants has altered nucleotide sequence and/or altered expression of said polypeptide;
- v) obtaining a sample and analysing the nucleic acid sequence of a nucleic acid molecule selected from the group consisting of:
  - a) a nucleic acid molecule comprising a nucleotide sequence as represented in 1, 2, 3, 4, 5, 6, 7, 8, 9 or 10;
  - b) a nucleic acid molecule that hybridises to the nucleic acid molecule in a) under stringent hybridisation conditions and that encodes a polypeptide with opiate alkaloid biosynthsynthetic activity; and optionally
- vi) comparing the nucleotide sequence of the nucleic acid molecule in said sample to a nucleotide sequence of a nucleic acid molecule of the original wild-type plant.

In a preferred method of the invention said nucleic acid molecule is analysed by a method comprising the steps of:

- i) extracting nucleic acid from said mutated plants;
- ii) amplification of a part of said nucleic acid molecule by a polymerase chain reaction;
- iii) forming a preparation comprising the amplified nucleic acid and nucleic acid extracted from wild-type seed to form heteroduplex nucleic acid;
- iv) incubating said preparation with a single stranded nuclease that cuts at a region of heteroduplex nucleic acid to identify the mismatch in said heteroduplex; and
- v) determining the site of the mismatch in said nucleic acid heteroduplex.

In a preferred method of the invention said *P. somniferum* plant has enhanced opiate alkaloid biosynthetic activity.

In an alternative preferred method of the invention said *P. somniferum* plant has reduced or abrogated opiate alkaloid biosynthetic activity.

According to a further aspect of the invention there is provided a *P. somniferum* plant obtained by the method according to the invention.

According to an aspect of the invention there is provided a *P. somniferum* plant wherein said plant comprises a viral vector that includes all or part of a gene comprising a nucleic acid molecule according to the invention.

In a preferred embodiment of the invention said gene or part is encoded by a nucleic acid molecule comprising a nucleic acid sequence selected from the group consisting of:

- i) a nucleic acid molecule comprising a nucleotide sequence as represented in 1, 2, 3, 4, 5, 6, 7, 8, 9 or 10;
- ii) a nucleic acid molecule comprising a nucleotide sequence that hybridises under stringent hybridisation conditions to a nucleic acid molecule in (i) and which encodes a polypeptide opiate alkaloid biosynthetic activity.

In a preferred embodiment of the invention said nucleic acid molecule comprises or consists of a nucleotide sequence as represented in SEQ ID NO: 21.

In a preferred embodiment of the invention said nucleic acid molecule comprises or consists of a nucleotide sequence as represented in SEQ ID NO: 22.

In a preferred embodiment of the invention said nucleic acid molecule comprises or consists of a nucleotide sequence as represented in SEQ ID NO: 23.

In a preferred embodiment of the invention said nucleic acid molecule comprises or consists of a nucleotide sequence as represented in SEQ ID NO: 24.

In a preferred embodiment of the invention said nucleic acid molecule comprises or consists of a nucleotide sequence as represented in SEQ ID NO: 25.

In a preferred embodiment of the invention said nucleic acid molecule comprises or consists of a nucleotide sequence as represented in SEQ ID NO: 26.

In a preferred embodiment of the invention said nucleic acid molecule comprises or consists of a nucleotide sequence as represented in SEQ ID NO: 27.

In a preferred embodiment of the invention said nucleic acid molecule comprises or consists of a nucleotide sequence as represented in SEQ ID NO: 28.

In a preferred embodiment of the invention said nucleic acid molecule comprises or consists of a nucleotide sequence as represented in SEQ ID NO: 29.

In a preferred embodiment of the invention said nucleic acid molecule comprises or consists of a nucleotide sequence as represented in SEQ ID NO: 30.

According to a further aspect of the invention there is provided a viral vector comprising all or part of a nucleic acid molecule according to the invention.

According to an aspect of the invention there is provided the use of a viral vector according to the invention in viral induced gene silencing in a *P. somniferum* plant.

Virus induced gene silencing [VIGS] is known in the art and exploits a RNA mediated antiviral defence mechanism. Plants that are infected with an unmodified virus induces a mechanism that specifically targets the viral genome. However, viral vectors which are engineered to include nucleic acid molecules derived from host plant genes also induce specific inhibition of viral vector expression and additionally target host mRNA. This allows gene specific gene silencing without genetic modification of the plant genome and is essentially a non-transgenic modification.

Throughout the description and claims of this specification, the words “comprise” and “contain” and variations of the words, for example “comprising” and “comprises”, means “including but not limited to”, and is not intended to (and does not) exclude other moieties, additives, components, integers or steps. “Consisting essentially” means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPITION OF THE FIGURES

Figure 1B:
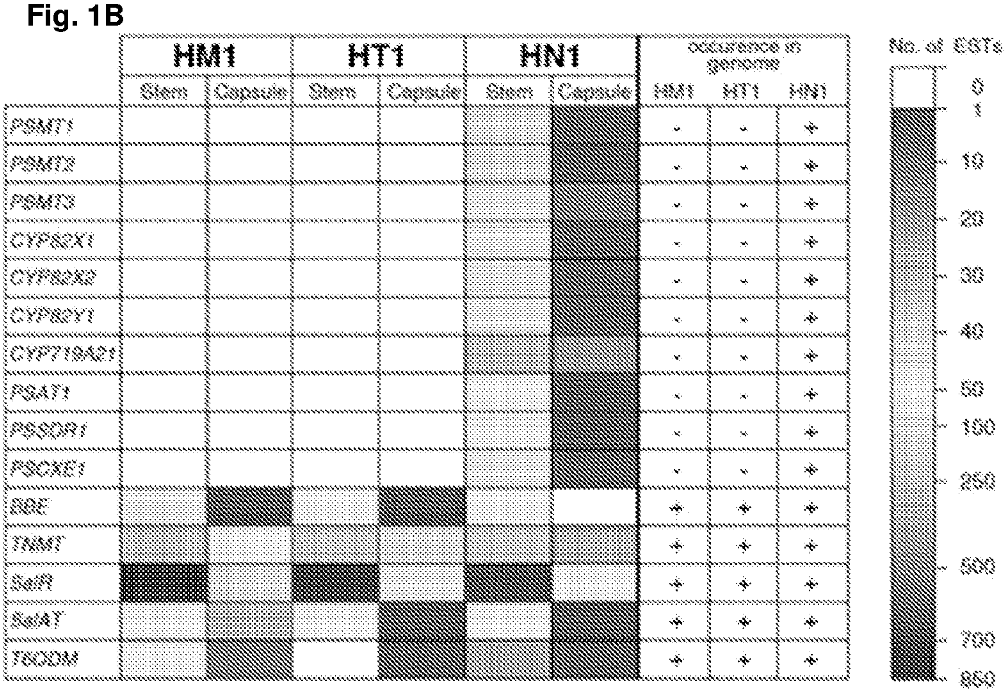
Figures 2A, 2B:
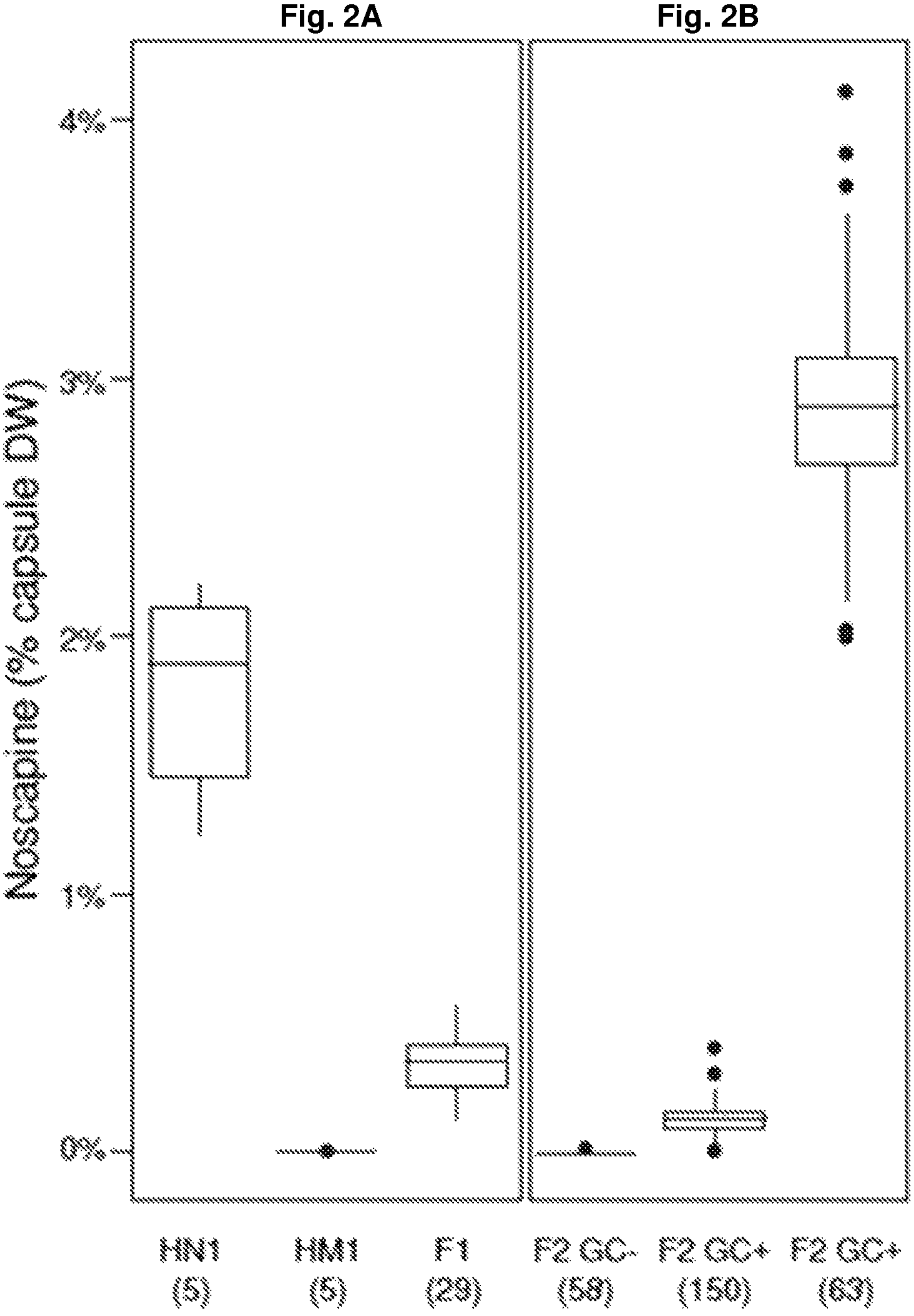
Figure 3:
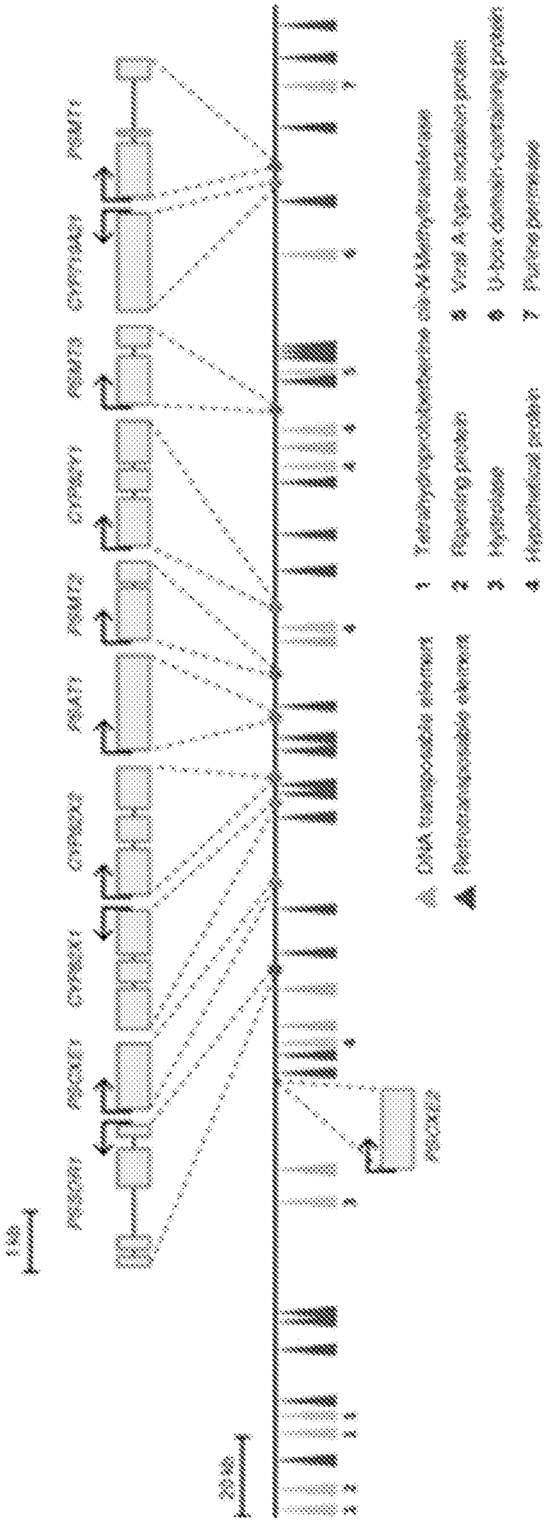
Figure 5A:
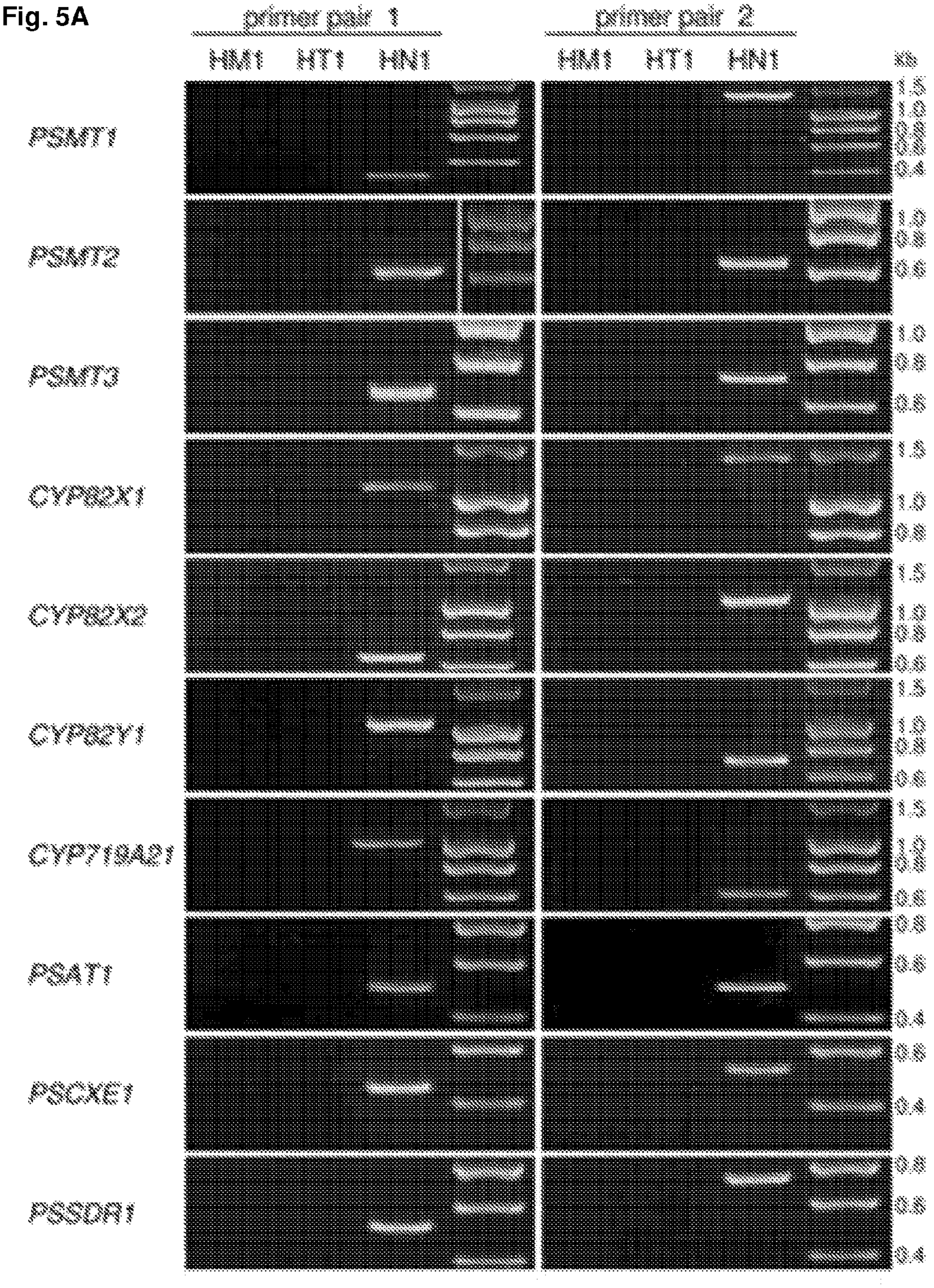
Figure 5B:
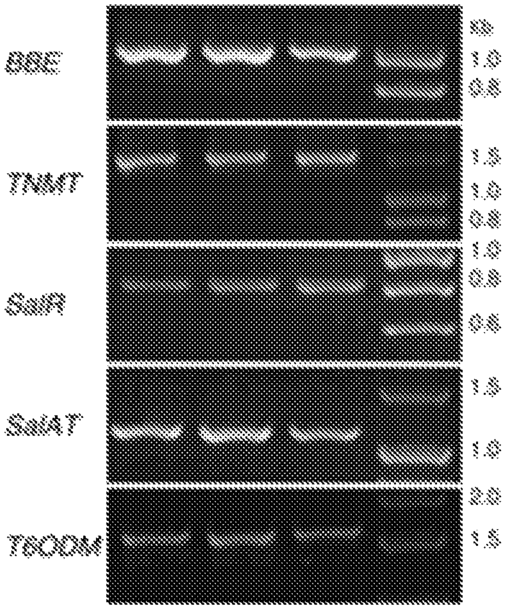

An embodiment of the invention will now be described by example only and with reference to the following figures:

FIGS. 1A-1B: Identification of genes exclusively present in the genome of a noscapine producing poppy variety, HN1 (High Noscapine 1). (A) Relative abundance of the major alkaloids extracted from the capsules of three commercial varieties of poppy, HM1 (High Morphine 1), HT1 (High Thebaine 1) and HN1. M=morphine, C=codeine, T=thebaine, O=oripavine and N=Noscapine. (B) EST libraries from stem and capsule were generated by pyrosequencing and unique contiguous sequences assembled as described in material and methods. Ten genes (PSMT1, PSMT2, PSMT3, CYP82X1, CYP82X2, CYP82Y1, CYP719A21, PSAT1, PSSDR1 and PSCXE1) as defined in the text, were represented only in EST libraries from the HN1 variety. EST abundance of five other functionally characterized *P. somniferum* genes (BBE, TNMT, SalR, SalAT and T6DM) show them to be expressed in all three varieties and at consistently higher levels in stem compared to capsule as is also the case for the HN1 specific genes as shown in colour code (FIG. 1). PCR on genomic DNA from all three varieties revealed that the ten HN1 specific genes are absent from the genomes of the HM1 and HT1 varieties (FIG. 5A);

FIGS. 2A-2B: Segregation analysis of noscapine content in an F2 mapping population demonstrates requirement for the noscapine gene cluster. (A) Box plot depiction of noscapine levels as percentage dry weight (DW) in glasshouse grown parental lines HN1 and HM1 and the F1 generation. (B) The field grown F2 generation segregated into three classes of zero, low and high noscapine. F2 GC− and F2 GC+ indicate the absence and presence respectively of the noscapine gene cluster. Numbers in brackets indicate number of individuals in each class;

FIG. 3: The HN1 gene cluster. The structure and position of the ten HN1 specific genes expressed in stems and capsule tissues is shown above the central black line which represents 401 Kb of genomic sequence. Exons are represented by filled grey boxes and introns by fine black lines. Arrows indicate the 5' to 3' orientation of each gene. Additional open reading frames depicted below the central black line are as defined by the key. None of these ORFs are represented in the stem and capsule EST libraries;

FIGS. 4A-4I: Functional characterisation using virus induced gene silencing of 6 genes from the HN1 gene cluster. (A-F) Results from both leaf latex and capsules are consistent with each of these genes encoding enzymes involved in noscapine biosynthesis. All compounds that accumulate, apart from scoulerine, have been putatively identified on the basis of mass spectra as detailed in FIG. 6A-6F. The mass-to-charge (m/z) value (M) followed by retention time (T) in seconds is shown for each compound on the horizontal axis. (G-I) Proposed pathway for noscapine biosynthesis based on VIGS data. Solid arrows depict steps supported by VIGS data, dotted arrows depict additional proposed steps. For the secoberbine intermediates, R1=H or OH, R2=H or OH and R3=CH2OH or CHO or COOH (FIGS. 6A-F). The noscapine structure is numbered according to the IUPAC convention;

FIGS. 5A-B: The ten genes exclusively expressed in the HN1 variety occur in the genome of HN1 but are absent from that of varieties HT1 and HM1. (A) Amplification of fragments from the ten genes exclusively expressed in HN1 using two different primer pairs. (B) Amplification of fragments of genes from the protoberberine and morphinan branch pathways that are expressed in all three varieties. Primers used are detailed in Table 3; HyperLadder I (Bioline Reagents, London, UK) was used as molecular size standard;

FIGS. 6A-6F. Evidence for putative identities of intermediates from VIGS experiments. All panels show the mass spectra of the pseudomolecular parent ion at the chromatographic peak apex in black and corresponding MS2 fragmentation spectra in red, scaled to relative abundance. MS2 spectra were generated by targeting the parent ion with an isolation width of 3 m/z and using collisional isolation dissociation energy set to 35%. All mass spectra were obtained at a resolution setting of 7500. Text printed above selected diagnostic ions indicate the exact monoisotopic mass of the ion, the calculated formula within limits C=1:100, O=0:200, N=0:3 and H=1:200, and the number/total number of formulae returned within a 5 ppm error window. Fragments were reconciled against theoretical fragments generated by submitting candidate parent structures to Mass Frontier software (version 5.01.2; HighChem, Bratislava, Slovakia). Candidate parent structures were derived from PubChem searches and the comprehensive review of *Papaver* spp. alkaloids (Sariyar (2002) *Pure Appl. Chem.* 74, 557-574). (A) Tetrahydrocolumbamine; this compound was characterized from a peak eluting at 174s from VIGS-silenced CYP719A21. Eight out of ten observed MS2 fragments were calculated as feasible by Mass Frontier; only the two most abundant diagnostic fragments are shown. (B) Secoberbine intermediate 1 (C21H25NO6); this compound was characterized from a peak eluting at 147s from VIGS-silenced CYP82X2. If R1=OH, R2=H, and R3=CH2OH, then this compound is narcotolinol which is consistent with both annotated fragments. Another candidate formula fit would be demethoxylated narcotindiol (R1=H, R2=OH, R3=CH2OH); however this structure would not form the observed fragment at 206.0816. (C) Secoberbine intermediate 2 ($C21H23NO6$); this compound was characterized from a peak eluting at 103s from VIGS-silenced CYP82X2. If R1=OH, R2=H, and R3=CHO, then this compound would be a desmethylated derivative of macrantaldehyde. (D) Papaveroxine; this compound was characterized from a peak eluting at 214s from VIGS-silenced PSCXE1. The 398.1600 fragment observed is consistent with deacetylation. (E) Narcotinehemiacetal; this compound was characterized from a peak eluting at 121s from VIGS-silenced PSSDR1. (F) Narcotoline (4'-desmethylnoscapine); this compound was characterized from a peak eluting at 208s from VIGS-silenced PSMT2. Other isobaric possibilities were 6- or 7-desmethylnoscapine. However, the 206.0816 fragment observed is consistent with a hydroxylated 4' position. Alternative structures could be discounted by comparing the candidate fragmentation spectra with that from synthetic 7-desmethylnoscapine, which eluted at a different retention time and lacked the characteristic 206.0816 fragment;

FIGS. 7A-7M are sequences of (A) PSMT1 nucleic acid sequence, SEQ ID NO: 1; (B) PSMT2 nucleic acid sequence, SEQ ID NO: 2; (C) PSMT3 nucleic acid sequence, SEQ ID NO: 3; (D) CYP82X1 nucleic acid sequence, SEQ ID NO: 4; (E) CYP719A21 nucleic acid sequence, SEQ ID NO: 5; (F) CYP82X2 nucleic acid sequence, SEQ ID NO: 6; (G) CYP82Y1 nucleic acid sequence, SEQ ID NO: 7; (H) PSCXE1 nucleic acid sequence, SEQ ID NO: 8; (I) PSSDR1 nucleic acid sequence, SEQ ID NO: 9; (J) PSAT1 nucleic acid sequence, SEQ ID NO: 10; PSMT1 protein sequence, SEQ ID NO: 11; PSMT2 protein sequence, SEQ ID NO: 12; (K) PSMT3 protein sequence, SEQ ID NO: 13; CYP82X1 protein sequence, SEQ ID NO: 14; CYP719A21 protein sequence, SEQ ID NO: 15; CYP82X2 protein sequence, SEQ ID NO: 16; CYP82Y1 protein sequence, SEQ ID NO: 17; (L) PSCXE1 protein sequence, SEQ ID NO: 18; PSSDR1 protein sequence, SEQ ID NO: 19; PSAT1 protein sequence, SEQ ID NO: 20; VIGS PSMT1 protein sequence, SEQ ID NO: 21; VIGS PSMT2 protein sequence, SEQ ID NO: 22; and VIGS CYP82X1 protein sequence, SEQ ID NO: 23; (M) VIGS CYP719A21 protein sequence, SEQ ID NO: 24; VIGS CYP82X2 protein sequence, SEQ ID NO: 25; VIGS CYP82Y1 protein sequence, SEQ ID NO: 26; VIGS PSCXE1 protein sequence, SEQ ID NO: 27; VIGS PSSDR1 protein sequence, SEQ ID NO: 28; VIGS PSAT1 protein sequence, SEQ ID NO: 29; and VIGS PSPDS protein sequence, SEQ ID NO: 30.

Table 1 Illustrates the % identity of CYP82Y1, PSCXE1, PSDFR1 and PSAT1 (SEQ ID 17-20) with their respective closest functionally characterised homologues. Accession numbers given are from GenBank, Swiss-Prot or PDB databases;

Table 2. Genotyping of F3 families derived from two F2 phenotypic classes: low noscapine and high noscapine. The observed versus expected segregation ratios strongly support the hypothesis that individuals in the low noscapine F2 class are heterozygous for the HN1 gene cluster and individuals in the high noscapine class are homozygous;

Table 3. Primer sequences and associated information.

TABLE 1

| Protein | % Identity | Accession number | Annotation |
|---|---|---|---|
| CYP82Y1 (SEQ ID NO 17) | 54 | | CYP82X1 from *Papaver somniferum* |
| | 48 | | CYP82X2 from *Papaver somniferum* |
| | 39 | ABM46919.1 | CYP82E3, nicotine demethylase from *Nicotiana tomentosiformis* |
| PSCXE1 (SEQ ID NO 18) | 45 | 2O7R_A | AeCXE1, Carboxyl esterase from *Actinidia eriantha* |
| PSSDR1 (SEQ ID NO 19) | 46 | AAB41550.1 | Vestitone reductase from *Medicago sativa* |
| | 45 | ABQ97018.1 | Dihydroflavonol 4-reductase from *Saussurea medusa* |
| PSAT1 (SEQ ID NO 20) | 66 | Q94FT4.1 | Salutaridinol 7-O-acetyltransferase from *Papaver somniferum* |

TABLE 2

| Noscapine class and genotyping result of F2 individual | F3 seed family (obtained through self-pollination of F2 individual) | Number of F3 individuals genotyped | Observed segregation of gene cluster in F3 progeny GC+ | GC− | Expected segregation in F3 if F2 low noscapine class is heterozygous and the high noscapine class is homozygous GC+ | GC− | Chi-Square X-squared | p-value |
|---|---|---|---|---|---|---|---|---|
| low noscapine/GC+ | S-111809 | 28 | 18 | 10 | 21 | 7 | 1.714 | 0.190 |
| low noscapine/GC+ | S-111835 | 26 | 18 | 8 | 19.5 | 6.5 | 0.462 | 0.497 |
| high noscapine/GC− | S-111714 | 28 | 28 | | 28 | | | |
| high noscapine/GC− | S-111854 | 54 | 54 | | 54 | | | |

TABLE 3

| Gene | Primer sequences (5'- to 3'-) Forward | SEQ ID NO | Reverse | SEQ ID NO | Notes | Application |
|---|---|---|---|---|---|---|
| PSMT1 | GATTCCCGATTTACTCC TGATG | 31 | AACACAAAATACGATTACTT ACTTTTGTCC | 32 | primer pair 1 | Primersfor the amplification |

TABLE 3-continued

| Gene | Primer sequences (5'- to 3'-) Forward | SEQ ID NO | Reverse | SEQ ID NO | Notes | Application |
|---|---|---|---|---|---|---|
| PSMT1 | TGCCTCATGTTATTTCT GTTGCC | 33 | GCATGAAATGGATGTAGTTA TCTTGG | 34 | primer pair 2 | of fragments from genomic |
| PSMT2 | ATTGATGTCGGTGGTGG TCACG | 35 | ATTCCCGTTCAAGTAAACAT GCGG | 36 | primer pair 1 | DNA of HM1,HT1 and HN1 as shown |
| PSMT2 | GCAACTGTTTCATTAAC AGGCACATCC | 37 | CAGTAAATTCACACATTCCG TATCTTCCC | 38 | primer pair 2 | in FIG. 5 |
| PSMT3 | GCTTCAGCATTGGTTAA CGAGTGC | 39 | GAGGGTAAGCCTCAATAACA GACTGG | 40 | primer pair 1 | |
| PSMT3 | AGACCGTTTGTACCGAA TTCTGC | 41 | TCGTTCCATTCGTGAAGAAT GC | 42 | primer pair 2 | |
| CYP82X1 | GAACCATTAAACACTTG AGTCATGC | 43 | TGCAATTGAATTTAGCTCAT CTCC | 44 | primer pair 1 | |
| CYP82X1 | TTGATGAACGACAAGGA ACCG | 45 | ATTCATGATTGTGACCTTTG TAATCC | 46 | primer pair 2 | |
| CYP82X2 | ATGTGGAAAACGGTAAG CAAGTGG | 47 | ACGATTCTGTCATCATCATT TTCGC | 48 | primer pair 1 | |
| CYP82X2 | CAACCTCAATCTAGCTA GAGTCG | 49 | CCCAAGATTTTCATATCCTT TACAA | 50 | primer pair 2 | |
| CYP82Y1 | CAATAATTGAGTAATTT CAGTTCATTCATGG | 51 | GCTCCGTAAGTGCTCCTGTG | 52 | primer pair 1 | |
| CYP82Y1 | GAATTGTGGTAAAAAAT TAGATGCAG | 53 | CCCTTCACATCTACCATCC CTT | 54 | primer pair 2 | |
| CYP719A21 | CAAAGAGTCAATCTGAC TCAAGCTAGC | 55 | CGAGTGCCCATGCAGTGG | 56 | primer pair 1 | |
| CYP719A21 | TCAAACCCTGCTACTAA CACTTACTTGC | 57 | CACTCCATCAGACACACAAG ACC | 58 | primer pair 2 | |
| PSAT1 | TTTTATCGACCTTGAGG AACAATTAGG | 59 | AAATGGCAGTTCCACCGC | 60 | primer pair 1 | |
| PSAT1 | GACTTCATGATGAAATC AGATGCAC | 61 | CACTGCTGACTTCCATATC AAAGC | 62 | primer pair 2 | |
| PSCXE1 | ATGCTGTTGATGCTTTA AACTGGG | 63 | AGCTGAATTTGTCGATCAA TAAGTGG | 64 | primer pair 1 | |
| PSCXE1 | AATAAAAATCCAACAAT GGCAGATCC | 65 | ACTGGCATGATATGCAACA TTAGC | 66 | primer pair 2 | |
| PSSDR1 | GGAAGATGTGAGCCACC TTAAAGC | 67 | GATACACTGGGAGGAGGAT GGG | 68 | primer pair 1 | |
| PSSDR1 | GAGAGTAACCACATCTT TGTTGTCGG | 69 | CGGCAAAATTCATTCCTTG AGC | 70 | primer pair 2 | |
| | | 71 | | 72 | | |
| BBE | GTTTACTCCCACGTGCA TC | 71 | CATTCCTCGTCTAATTCATC TGC | 72 | | |
| TNMT | GTTTACTCCCACGTGCA TC | 73 | GCTTCACTACTTCTTCTTG AAAAG | 74 | | |
| SalR | AAACAATGCTGGGGTTGC | 75 | CATTATAATTTCCAATGCCGT AGTTC | 76 | | |
| SalAT | TAAGAGAGGGAGACCAC GAG | 77 | CATTCGTTGTTGTTGCTG GTAAG | 78 | | |
| T6ODM | CTTATGAAGCTAGGTAA TGGTATGGA | 79 | CATCCTCATTGCTTGTGT CC | 80 | | |
| PSMT1 | CTCTAAAATGCCAAACG CG | 81 | | | sequencing primer | Primers used as sequencing primers |
| PSMT1 | GACCCTTTGGGACTTCC TCG | 82 | | | sequencing primer | to obtain genomic DNA sequence from |
| PSMT1 | CGTGTTGTTTGGTCCCT CG | 83 | | | sequencing primer | HN1 |
| PSMT1 | TGCCTCATGTTATTTCT GTTGCC | 84 | | | sequencing primer | |
| PSMT1 | GATTCCCGATTTACTCC TGATGG | 85 | | | sequencing primer | |
| PSMT1 | AACACAAAATACGATTA CTTACTTTTGTCC | 86 | | | sequencing primer | |
| PSMT1 | TGCCTCATGTTATTTCT GTTGCC | 87 | | | sequencing primer | |
| PSMT1 | GCATGAAATGGATGTAG TTATCTTGG | 88 | | | sequencing primer | |

TABLE 3-continued

| Gene | Primer sequences (5'- to 3'-) Forward | SEQ ID NO | Reverse | SEQ ID NO | Notes | Application |
|---|---|---|---|---|---|---|
| PSMT1 | AAATCGTTCGCTCTTTA CCGC | 89 | | | sequenc- ing primer | |
| PSMT1 | CACACCAAACTTGATCA TTGTC | 90 | | | sequenc- ing primer | |
| PSMT2 | ATTGTTGATATTGAATC AGAAACTTTC | 91 | | | sequenc- ing primer | |
| PSMT2 | TCAATACCAGTACTGTT AGTTTCCG | 92 | | | sequenc- ing primer | |
| PSMT2 | GCAACTGTTTCATTAAC AGGCACATCC | 93 | | | sequenc- ing primer | |
| PSMT2 | ATTGATGTCGGTGGTGG TCACG | 94 | | | sequenc- ing primer | |
| PSMT2 | GCACACTGTCTTTTTCT TCCACC | 95 | | | sequenc- ing primer | |
| PSMT2 | ACCGGAATGAGAATGCA TAAAGTAAAGG | 96 | | | sequenc- ing primer | |
| PSMT2 | CCAATACCCAATCAATT AAACTC | 97 | | | sequenc- ing primer | |
| PSMT2 | CAGTAAATTCACACATT CCGTATCTTCCC | 98 | | | sequenc- ing primer | |
| PSMT3 | ATTGTATAGCCAAAGTT GCAGGTAGGG | 99 | | | sequenc- ing primer | |
| PSMT3 | AGACCGTTTGTACCGAA TTCTGC | 100 | | | sequenc- ing primer | |
| PSMT3 | GCAGTGAAAGCCATATC CAAAGC | 101 | | | sequenc- ing primer | |
| PSMT3 | AACCGTCCCCAAGATGA TTCC | 102 | | | sequenc- ing primer | |
| PSMT3 | TCGTTCCATTCGTGAAG AATGC | 103 | | | sequenc- ing primer | |
| PSMT3 | GAGGGTAAGCCTCAATA ACAGACTGG | 104 | | | sequenc- ing primer | |
| CYP82X1 | GAACCATTAAACACTTG AGTCATGC | 105 | | | sequenc- ing primer | |
| CYP82X1 | TTGATGAACGACAAGGA ACCG | 106 | | | sequenc- ing primer | |
| CYP82X1 | TCGACAGCGGTTACGAA CG | 107 | | | sequenc- ing primer | |
| CYP82X1 | CAATTATCAAAGAATCA ATGC | 108 | | | sequenc- ing primer | |
| CYP82X1 | TGCAATTGAATTTAGCT CATCT | 109 | | | sequenc- ing primer | |
| CYP82X1 | ATTCATGATTGTGACCT TTGTAATCC | 110 | | | sequenc- ing primer | |
| CYP82X1 | GACAGAGGGCCCAAGTT AAGG | 111 | | | sequenc- ing primer | |
| CYP82X1 | AGCAAACCATTCGTCCA TCC | 112 | | | sequenc- ing primer | |
| CYP82X1 | TACGACAGGTTGCTAGC TTGG | 113 | | | sequenc- ing primer | |
| CYP82X2 | AATAATGGATCAGTCAC GGCTTCC | 114 | | | sequenc- ing primer | |

TABLE 3-continued

| Gene | Primer sequences (5'- to 3'-) Forward | SEQ ID NO | Reverse | SEQ ID NO | Notes | Application |
|---|---|---|---|---|---|---|
| CYP82X2 | AATCCATCAGATTTTCA ACCAGAGAGG | 115 | | | sequenc-ing primer | |
| CYP82X2 | TGTCAGCCAACCATTCG TCCATCCTAAC | 116 | | | sequenc-ing primer | |
| CYP82X2 | GGCTTCCCGGAGATGAC CCAGATTTTAT | 117 | | | sequenc-ing primer | |
| CYP82X2 | TTGTTATTTTCATGACT ATTACCACCAGCTTCCT CTTA | 118 | | | sequenc-ing primer | |
| CYP82X2 | AGTGGAGGAGGCACAAA AGTTAGGATGGAC | 119 | | | sequenc-ing primer | |
| CYP82X2 | CCATGTCTGATAAATAC GGGTCGGTGTTC | 120 | | | sequenc-ing primer | |
| CYP82X2 | TTGTTGATAAGGACGAC TAAGAATAAGCAGAAGA TA | 121 | | | sequenc-ing primer | |
| CYP82X2 | ACGATTCTGTCATCATC ATTTTCGC | 122 | | | sequenc-ing primer | |
| CYP82X2 | AGTCGTGTATCGTTCGC TTAATGC | 123 | | | sequenc-ing primer | |
| CYP82X2 | CATGCCTATCTATTTCC TCCCTTGCCCTC | 124 | | | sequenc-ing primer | |
| CYP82X2 | TGTCAGCCAACCATTCG TCCATCCTAAC | 125 | | | sequenc-ing primer | |
| CYP82X2 | TGTTCGATCACGTTGTC TCTTTTTGCCATAA | 126 | | | sequenc-ing primer | |
| CYP82X2 | TAACAATAAAAGTACTG ATAATGGTGGTCGAAGG AGAA | 127 | | | sequenc-ing primer | |
| CYP82Y1 | TATTGATGTGGACCAGT ACC | 128 | | | sequenc-ing primer | |
| CYP82Y1 | TGTAACTCTTGGTCACA TGG | 129 | | | sequenc-ing primer | |
| CYP82Y1 | CGCGTACTTGACATTTA ACG | 130 | | | sequenc-ing primer | |
| CYP82Y1 | GGATCATCGCCAAAAGA AAC | 131 | | | sequenc-ing primer | |
| CYP719A21 | CAAAGAGTCAATCTGAC TCAAGCTAGC | 132 | | | sequenc-ing primer | |
| CYP719A21 | TGAAATGCCTGAGATCA CTAAAATCG | 133 | | | sequenc-ing primer | |
| CYP719A21 | TCAAACCCTGCTACTAA CACTTACTTGC | 134 | | | sequenc-ing primer | |
| CYP719A21 | TGTAAAGACACTTCATT GATGGGC | 135 | | | sequenc-ing primer | |
| CYP719A21 | TTCGATTTGTGTAAACA TTAATGATATTTGG | 136 | | | sequenc-ing primer | |
| CYP719A21 | GAGATGATCAAGTGGTT TAACCATTCC | 137 | | | sequenc-ing primer | |
| CYP719A21 | CGAGTGCCCATGCAGTGG | 138 | | | sequenc-ing primer | |
| PSCXE1 | AATAAAAATCCAACAAT GGCAGATCC | 139 | | | sequenc-ing primer | |
| PSCXE1 | ATGCTGTTGATGCTTTA AACTGGG | 140 | | | sequenc-ing primer | |

TABLE 3-continued

| Gene | Primer sequences (5'- to 3'-) Forward | SEQ ID NO | Reverse | SEQ ID NO | Notes | Application |
|---|---|---|---|---|---|---|
| PSCXE1 | GGTTAATCGAGAGATGT TTTGTGGTAGG | 141 | | | sequencing primer | |
| PSCXE1 | CGATGACACAGAGCAAG AACGAC | 142 | | | sequencing primer | |
| PSCXE1 | CGCGGGTATATGTGTAG CAATCG | 143 | | | sequencing primer | |
| PSCXE1 | CGGCAACGCCAGTTCCC | 144 | | | sequencing primer | |
| PSSDR1 | CTAACAGGCAAACAATA ACAGGTTGC | 145 | | | sequencing primer | |
| PSSDR1 | GGAAGATGTGAGCCACC TTAAAGC | 146 | | | sequencing primer | |
| PSSDR1 | AAAGGTACTGACAGAAA GAGCTTGCC | 147 | | | sequencing primer | |
| PSSDR1 | AGATACACTGGGAGGAG GATGGG | 148 | | | sequencing primer | |
| PSSDR1 | CGGCAAAATTCATTCCT TGAGC | 149 | | | sequencing primer | |
| PSSDR1 | AACATATAGCCAAAGGA CTCTTCG | 150 | | | sequencing primer | |
| PSAT1 | AGGATACACAATGACCC AAC | 151 | | | sequencing primer | |
| PSAT1 | TTTTATCGACCTTGAGG AACAATTAGG | 152 | | | sequencing primer | |
| PSAT1 | TGTTCACTAGGTGGAAA GAG | 153 | | | sequencing primer | |
| PSAT1 | AGTACAATACCGAGAAA TCCGACAAG | 154 | | | sequencing primer | |
| PSAT1 | GCTCAATTAATGGAACA GTAGTTACCC | 155 | | | sequencing primer | |
| | | | | | specific PCR conditions: | |
| PsMT1 | VIC®-CGTGTTGTTTGG TCCCTCG | 156 | GCACACTGTCTTTTTCTTC CACC | 157 | 30 cylces, 20 s extension at 72° | Primer pairs for genotyping of the F2 mapping population |
| PsMT2 | VIC®-GCAACTGITTCA TTAACAGGCACATCC | 158 | GCCAGCGCTAATACAAGGA TGTGG | 159 | 36 cylces, 50 s extension at 72° | |
| PsMT3 | VIC®-GCAGTGAAAGCC ATATCCAAAGC | 160 | TCGTTCCATTCGTGAAGAA TGC | 161 | 30 cylces, 30 s extension at 72° | |
| CYP82X1 | VIC®-GCTACGAAAGAT AATGGTGCAGC | 162 | AGCAAACCATTCGTCCATCC | 163 | 30 cylces, 30 s extension at 72° | |
| CYP82X2 | VIC®-ATGTGGAAAACG GTAAGCAAGTGG | 164 | ACGATTCTGTCATCATCAT TTTCGC | 165 | 30 cylces, 50 s extension at 72° | |
| CYP719A21 | VIC®-TGAAATGCCTGA GATCACTAAAATCG | 166 | GGAATGGTTAAACCACTTG ATCATCTC | 167 | 30 cylces, 30 s extension at 72° | |
| PSCXE1 | VIC®-ATGCCAGTTTAA GAGCAATAGAAATGG | 168 | GGGAACTGGCGTTGCCG | 169 | 30 cylces, 30 s extension at 72° | |
| PSSDR1 | VIC®-GAAGATGTGAGC CACCTTAAAGC | 170 | GCTCAAGGAATGAATTTTG CCG | 171 | 30 cylces, 30 s extension at 72° | |
| CYP82X2 | GTTGACGCAGGAAGCTT TTGC | 172 | GGAACATAAGATTTAACTC CGCCTC | 173 | Primer pair for PCR amplification of the BAC library screening probe | |
| PSMT1 | aaactcgagaagctTGG TCATAATCATCAATCAG | 174 | aaaggtaccCATGTACTAC TACATCATCTCC | 175 | | Primer pairs for the amplification and cloning of fragments selected for VIGS |
| PSMT2 | aaactcgagaagcttGT GTAACTAAGCCAGCGC | 176 | aaaggtaccACTTGAATAT ATCACCGC | 177 | | |
| CYP82X1 | aaaggatccTTTGAGTA ATGGTGAAAAGA | 178 | aaaggtaccAACATCTACT CTCGAGGATTG | 179 | | |
| CYP82X2 | aaactcgagaagcttTA GGAGGGTATGTCCGGC | 180 | aaaggtaccTTAACTCCGC CTCGGCTCC | 181 | | |
| CYP82Y1 | aaaggatccTTCAGTT CATTCATGGCG | 182 | aaaggtaccGTTCATAGTAA ATAATAACAGGCG | 183 | | |
| CYP719A21 | aaactcgagaagcttAT GATCATGAGTAACTTAT GGA | 184 | aaaggtaccCCAACAGGCCA TTCCGTTG | 185 | | |

TABLE 3-continued

| Gene | Primer sequences (5'- to 3'-) Forward | SEQ ID NO | Reverse | SEQ ID NO | Notes | Application |
|---|---|---|---|---|---|---|
| PSCXE1 | aaaggatccTGGCAGATCCTTATGAATTCC | 186 | aaaggtaccTTATGATAGGAAGCAGCTTATTC | 187 | | |
| PSSDR1 | aaaggatccGAAATTGACGAGACAATATGG | 188 | aaaggtaccCATTCAAAAACGAATATGTGTGC | 189 | | |
| PSAT1 | aaaggatccCCTAAGAGAGATCCTCCAACTG | 190 | aaaggtaccAATACAAGTATGAAAACAAGAGAATAA | 191 | | |
| PSPDS | GAGGTGTTCATTGCCATGTCAA | 192 | GTTTCGCAAGCTCCTGCATAGT | 193 | | |

Materials and Methods

Plant Material Three GSK Australia poppy varieties that predominantly accumulate either noscapine (High Noscapine, HN1), morphine (High Morphine, HM1) or thebaine (High Thebaine HT1), were grown in Maxi (Fleet) Rootrainers™ (Haxnicks, Mere, UK) under glass in 16 hour days at the University of York horticulture facilities. The growth substrate consisted of 4 parts John Innes No. 2, 1 part Perlite and 2 parts Vermiculite. The HM1×HN1 F2 mapping population was grown at the GlaxoSmithKline Australia field-trial site, Latrobe, Tasmania from September 2009 to February 2010.

Crossing and Selfing Crosses were carried out between HN1 and HM1 individuals to generate F1 hybrid seed. At the hook stage of inflorescence development, immature stamens were removed from selected HN1 flower buds. HN1 stigmas were fertilized with pollen from synchronously developing HM1 flowers shortly after onset of anthesis. To prevent contaminating pollen from reaching the receptive stigmas, emasculated flowers were covered with a muslin bag for four days after pollination. Both the F1 and F2 generations were self-pollinated to produce F2 and F3 seed, respectively. Self -pollination was ensured by covering the flowers shortly before onset of anthesis with a muslin bag.

RNA Isolation and cDNA Synthesis Upper stems (defined as the 2 cm section Immediately underneath the capsule) and whole capsules were harvested at two developmental stages represented by 1-3 days and 4-6 days, after petal fall. Five plants were used per developmental stage and cultivar. The material was ground to a fine powder in liquid nitrogen using a mortar and pestle. RNA was isolated from the powder using a CTAB-based extraction method (Chang et al (1993) Plant Mol. Biol. Rep. 11 113-116) with small modifications: (i) three sequential extractions with chloroform:isoamylalcohol (24:1) were performed and (ii) the RNA was precipitated overnight with lithium chloride at 4° C. After spectrophotometric quantification, equal amounts of RNA were pooled from five plants per cultivar, development stage and organ. The pooled samples underwent a final purification step using an RNeasy Plus MicroKit (Qiagen, Crawley, UK). RNA was typically eluted in 30-100 μl water. cDNA was prepared with the SMART cDNA Library Construction Kit (Clontech, Saint-Germainen-Laye, France) according to the manufacturer's instructions but using SuperScript II Reverse Transcriptase (Invitrogen, Paisley, UK) for first strand synthesis. The CDSIII/3'PCR primer was modified to: 5' ATT CTA GAT CCR ACA TGT TTT TTT TTT TTT TTT TTT TVN 3' where R=A or G, V=A, C or G; N=A/T or C/G. SEQ ID NO 194). Following digestion with MmeI (New England Biolabs, Hitchin, UK) the cDNA was finally purified using a QIAquick PCR Purification kit (Qiagen, Crawley, UK).

cDNA Pyrosequencing: Pyrosequencing was performed on the Roche 454 GS-FLX sequencing platform (Branford, Conn.) using cDNA prepared from the following four samples of each of the three varieties:

i. upper stem, 1-3 days after petal fall ii. upper stem, 4-6 days after petal fall iii. capsule, 1-3 days after petal fall iv. capsule, 4-6 days after petal fall Raw Sequence Analysis, Contiguous Sequence Assembly and Annotation The raw sequence datasets were derived from parallel tagged sequencing on the 454 sequencing platform (Meyer et al (2008) Nature Prot. 3, 267-78). Primer and tag sequences were first removed from all individual sequence reads. Contiguous sequence assembly was only performed on sequences longer than 40 nucleotides and containing less than 3% unknown (N) residues. Those high quality Expressed Sequence Tag (EST) sequences were assembled into unique contiguous sequences with the CAPS Sequence Assembly Program (Huang and Madan (1999) Genome Res. 9, 868-877), and the resulting contigs were annotated locally using the BLAST2 program (Altschul et al. (1997) Nucleic Acids Res. 25, 3389-3402) against the non-redundant peptide database downloaded from the NCBI.

Expression profiling: The number of ESTs associated with a specific consensus sequence representing each of the candidate genes detailed in FIG. 1B was counted for each EST library. EST numbers were normalised on the basis of total number of ESTs obtained per library. For each variety, EST counts were combined for the two developmental stages from both stems and capsules. Differences in candidate gene expression levels between organs and varieties were visualised as a heat map using Microsoft Excel.

Preparation of Genomic DNA from Glasshouse Grown Plants In order to amplify and obtain genomic sequences of the candidate genes 30-50 mgs of leaf material was collected from 4-6 week old glasshouse-grown seedlings from each of the three varieties. Genomic DNA was extracted using the BioSprint 96 Plant kit on the BioSprint 96 Workstation (Qiagen, Crawley, UK) according to the manufacturer's protocol. Extracted DNA was quantified using Hoescht 33258 and normalized to 10 ng/ul.

Amplification and Sequencing of Candidate Genes from Genomic DNA Primers for amplification and Sanger-sequencing of the candidate genes from genomic DNA were based on the respective contiguous sequences assembled from the ESTs or on BAC sequences. The primer sequences are shown in Table 3. PCR amplifications were performed on pools of genomic DNA comprising DNA from four individuals. Amplification was typically carried out on 10 ng genomic DNA in 1× Phusion High Fidelity Buffer supplemented with 200 nM forward and reverse primers, 0.2 mM dNTPs, 0.02 units/μl Phusion Hot Start DNA Polymerase (Finnzymes, Vantaa, Finnland). Standard PCR conditions were used throughout with annealing temperatures and times dependent on primers and PCR equipment.

DNA Extraction from the Field-Grown F2 Mapping Population 40-50 mg of leaf tissue was harvested from F2 plants at the 'small rosette' growth stage (~10 leaves present on each plant) into 1.2 ml sample tubes. A 3 mm tungsten carbide bead was added to each tube and samples were kept at −80° C. for a minimum of two hours prior to freeze-drying for 18 hours. Following freeze drying, samples were powdered by bead-milling (Model TissueLyser, Qiagen, Hilden, Germany) at 30 Hz for two 60 s cycles separated by plate inversion. DNA extraction was performed with the Nucleospin Plant II kit (Macherey-Nagel, Duren, Germany) using the supplied Buffer Set PL2/3 following the manufacturer's protocol for centrifugal extraction. DNA was quantified by UV-spectroscopy.

Genotyping of the HN1×HM1 F2 Mapping Population for the Presence or Absence of the HN1-Specific Candidate Genes Plants of the F2 mapping population were genotyped for the presence or absence of eight candidate genes. The gene primer pairs (Table 3) were designed with fluorescent tags (5'-VIC®-labeled) for use on the ABI 3730xl capillary apparatus (Applied Biosystems, Foster City, Calif.). PCR amplifications were typically carried out on 10 ng genomic DNA in 1×GoTaq buffer supplemented with 1 mM $MgCl_2$, 500 nM forward and reverse primer, 0.125 mM dNTPs, 0.1 U GoTaq (Promega, Southampton, UK). The amplification conditions were: 1 min 94° C., 30-36 cycles of 30 s denaturation at 94° C., 30 s annealing at 62° C. and 20-50 s extension at 72° C., followed by a final extension for 5 min at 72° C. Cycle number and extension times depended on the candidate gene (Table 3). Amplification products were diluted 1:20 in $H_2O$ and fractionated on an ABI 3730xl capillary sequencer (Applied Biosystems, Foster City, Calif.). Data were scored using GeneMarker™ software (Softgenetics, State College, Pa.).

Poppy Straw Analysis from Field Grown F2 Plants Poppy capsules were harvested by hand from the mapping population once capsules had dried to approximately 10% moisture on the plant. After manually separating the seed from the capsule, the capsule straw samples (Poppy Straw) were then ground in a ball mill (Model MM04, Retsch, Haan, Germany) into a fine powder. Samples of ground poppy straw were then weighed accurately to 2±0.003 g and extracted in 50 ml of a 10% acetic acid solution. The extraction suspension was shaken on an orbital shaker at 200 rpm for a minimum of 10 min, then filtered to provide a clear filtrate. The final filtrate was passed through a 0.22 μm filter prior to analysis. The loss on drying (LOD) of the straw was determined by drying in an oven at 105° C. for 3 hours.

All solutions were analysed using a Waters Acquity UPLC system (Waters Ltd., Elstree, UK). fitted with a Waters Acquity BEH C18 column, 2.1 mm×100 mm with 1.7 micron packing. The mobile phase used a gradient profile with eluent A consisting of 10 mM ammonium bicarbonate of pH 10.2 and eluent B methanol. The mobile phase gradient conditions used are as listed in the table below with a linear gradient. The flow rate was 0.5 ml per minute and the column maintained at 60° C. The injection volume was 2 μl and eluted peaks were ionised in positive APCI mode and detected within 5 ppm mass accuracy using a Thermo LTQ-Orbitrap. The runs were controlled by Thermo Xcalibur software (Thermo Fisher Scientific Inc., Hemel Hempstead, UK).

Gradient Flow Program:

| TIME (minutes) | % Eluent A | % Eluent B | Flow (ml/min) |
|---|---|---|---|
| 0.0 | 98. | 2.0 | 0.50 |
| 0.2 | 98.0 | 2.0 | 0.50 |
| 0.5 | 60.0 | 40 | 0.50 |
| 4.0 | 20.0 | 80.0 | 0.50 |
| 4.5 | 20.0 | 80.0 | 0.50 |

Mass spectra were collected over the 150-900 m/z range at a resolution setting of 7500. All data analysis was carried out in the R programming language in a 64-bit Linux environment (R 2.11). Peak-picking was performed using the Bioconductor package, XCMS (Smith et al (2006) Anal. Chem. 78, 779-787), employing the centWave algorithm (Tautenhahn et al (2008) BMC Bioinformatics 9, 504). Redundancy in peak lists was reduced using the CAMERA package (Kuhl et al (2012) Anal. Chem. 84, 283-289). Alkaloids were identified by comparing exact mass and retention time values to those of standards and quantified by their pseudomolecular ion areas using custom R scripts.

Bacterial Artificial Chromosome (BAC) Library Construction The HN1 BAC library was constructed from high molecular weight (HMW) genomic DNA processed at Amplicon Express, Inc. (Pullman, Wash.) from four week old seedlings using the method described (Tao et al (2002) Theor. Appl. Genet. 105, 1058-1066). The HMW DNA was partially digested with the restriction enzyme HindIII and size selected prior to ligation of fragments into the pCC1BAC vector (Epicentre Biotechnologies, Madison, Wis.) and transformation of DH10B *E. coli* cells, which were then plated on Luria-Bertani (LB) agar with chloramphenicol, X-gal and IPTG at appropriate concentrations. Clones were robotically picked with a Genetix QPIX (Molecular Devices, Sunnyvale, Calif.) into 240 384-well plates containing LB freezing media. Plates were incubated for 16 hours, replicated and then frozen at −80° C. The replicated copy was used as a source plate for nylon filters that were made and used for screening using the PCR DIG Probe Synthesis Kit (Roche Applied Science, Indianapolis, Ind.). To estimate insert sizes, DNA aliquots of 10 BAC minipreps were digested with 5 U of NotI enzyme for 3 hours at 37° C. The digestion products were separated by pulsed-field gel electrophoresis (CHEF-DRIII system, Bio-Rad, Hercules, Calif.) in a 1% agarose gel in TBE. Insert sizes were compared to those of the Lambda Ladder MidRange I PFG Marker (New England Biolabs, Ipswich, Mass.). Electrophoresis was carried out for 18 hours at 14° C. with an initial switch time of 5 s, a final switch time of 15 s, in a voltage gradient of 6 V/cm. The average BAC clone size for the library was found to be 150 Kb.

Filter Construction and Screening Filter design and screening was carried out at Amplicon Express, Inc. (Pullman, Wash.). Bioassay dishes containing LB agar plate media and 12.5 μg/mL chloramphenicol were prepared. Positively charged nylon Amersham Hybond-$N^+$ membrane (GE Healthcare Bio-Sciences, Piscataway, N.J.) was applied to the media surface and the GeneMachines G3 (Genomics Solutions, Bath, UK) was used to robotically grid 18,432 clones in duplicate on filters. The filters were incubated at 37° C. for 12 to 14 hours. The filters were processed using the nylon filter lysis method (Sambrook et al., Molecular Cloning: A Laboratory Manual (Cold Spring Harbor Laboratory Press, Cold Spring Harbor, N.Y., 2001, ed. 3, vol. 1, chap. 1) with slight modifications. Following processing, the DNA was linked to the hybridization membrane filters according to the Hybond N+ manual by baking at 80° C. for 2 hours. To screen the library a 643 bp digoxigenin (DIG)-labeled probe representing position 2161-2803 in the genomic sequence of CYP82X2 (SEQ ID NO 6) was generated from 1.5 ng gDNA by PCR reaction using the primers shown in Table 3 and the PCR DIG synthesis kit (Roche Applied Science, Indianapolis, Ind.) according to the manufacturer's instructions. A non-labeled probe was amplified, diluted and spotted to each filter in the following dilutions of 2 ng, 1 ng, 0.1 ng and 0.0 ng as a positive control. The controls were baked at 80° C. for 30 min. Following a 30 min prehybridizing wash in DIG EasyHyb solution at 45° C. approximately 0.5 μl of denatured DIG labeled PCR product was added per ml of hybridization solution with the nylon filters and incubated with gentle shaking overnight at 45° C. The nylon filters were washed twice in a 2× standard sodium citrate (SSC), 0.1% sodium dodecyl sulfate (SDS) buffer at room temperature for 5 min each, and twice with a 0.5×SSC, 0.1% SDS buffer at 65° C. for 15 minutes each. The hybridized probe was detected using NBT/BCIP stock solution according to the manufacturer's instructions (Roche Applied Science, Indianapolis, Ind.) and was found to hybridize to six BAC clones.

BAC sequencing and automated sequence assembly: The six positive BAC clones from the BAC library were sequenced at Amplicon Express, Inc. (Pullman, Wash.) by Focused Genome Sequencing (FGS) with an average depth of 100× coverage. FGS is a Next Generation Sequencing (NGS) method developed at Amplicon Express that allows very high quality assembly of BAC clone sequence data using the Illumina HiSeq platform (Illumina, Inc, San Diego, Calif.). The proprietary FGS process makes NGS tagged libraries of BAC clones and generates a consensus sequence of the BAC clones with all reads assembled at 80 bp overlap and 98% identity. The gapped contiguous sequences were ordered and orientated manually based on mate pair sequences from four libraries of insert size 5000, 2000, 500 and 170 bp. Overlapping BAC clones, PS_BAC193L09, PS_BAC179L19, PS_BAC150A23 and PS_BAC164F07, which together encoded all 10 genes from the HN1 cluster, were selected for further sequence assembly. Where possible, gaps and ambiguous regions on both BAC clones were covered by primer walking with traditional Sanger sequencing to validate the assembly. Combination of the four overlapping BAC sequences gave a single continuous consensus sequence assembly of 401 Kb. The sequences of the 10 genes from the HN1 cluster were determined independently by Sanger sequencing and the 100% agreement of the Sanger determined gene sequences with the assembly from FGS provided quality assurance for the whole assembly.

Annotation of the assembled sequence: The sequences of the four BAC clones were annotated with an automated gene prediction program FGENESH (Salamov and Solovyev (2002) Genome Res. 10, 516-522). The gene structure including exon-intron arrangement for the 10 genes in the HN1 cluster was validated by comparison with cDNA sequence for each gene. cDNA sequence was not available for any of the remaining ORFs detailed in FIG. 3 since they are not represented in any of the EST libraries. The predicted function of all ORFs was evaluated by BLAST analysis (Altschul et al (1997) Nucleic Acids Res. 25, 3389-3402) and those ORFs with significant hits (e-value less than $1e^{-8}$) were included in FIG. 3.

Generation of Plasmid Constructs for Virus Induced Gene Silencing (VIGS) The tobacco rattle virus (TRV) based gene silencing system (Liu et al (2002) Plant J. 30, 415-422) was used to investigate the gene function of PSMT1, PSMT2, CYP719A21, CYP82X2, PSSDR1 and PSCXE1. DNA fragments selected for silencing were amplified by PCR and cloned into the silencing vector pTRV2 (GenBank accession no: AF406991). They were linked to a 129 bp-long fragment (SEQ ID NO: 30) of the *P. somniferum* PHYTOENE DESATURASE gene (PSPDS) in order to simultaneously silence the respective candidate genes and PSPDS. Plants displaying the photo-bleaching phenotype resulting from PSPDS silencing (Hileman et al (2005) Plant J. 44, 334-341) were identified as plants successfully infected with the respective silencing constructs and selected for further analysis.

Generation of the pTRV2:PDS construct: A 622 bp fragment of PSPDS was amplified from cDNA prepared from HN1 using primers shown in Table 3. Sau3Al digestion of the 622 bp PCR product yielded among others a fragment of 129 bp (SEQ ID NO: 30) which was cloned into the BamHI site of the pTRV2 vector. The orientation and fidelity was confirmed by sequencing and the resulting pTRV2:PDS vector was used in the generation of the VIGS construct for each candidate gene. The pTRV2:PDS construct also served as the control in the VIGS experiments.

DNA fragments selected for silencing the respective candidate genes were amplified from either HN1 genomic or cDNA. Primers used for amplification as well as the positions of the selected sequences within the respective open reading frames are shown in Table 3. The PSMT1, CYP719A21 and CYP82X2 fragments were first cloned into pTV00 (Ratcliff et al (2001) Plant J., 237-245) using HindIII and KpnI and then subcloned into pTRV2:PDS using BamHI and KpnI. PSMT2, PSCXE1 and PSSDR1 fragments were cloned directly into pTRV2:PDS using BamHI and KpnI. The orientation and fidelity of all constructs was confirmed by sequencing.

Transformation of *Agrobacterium tumefaciens* with VIGS constructs: VIGS constructs were propagated in *E. coli* strain DH5α and transformed into electrocompetent *Agrobacterium tumefaciens* (strain GV3101) by electroporation.

Infiltration of plants: Separate overnight liquid cultures of *A. tumefaciens* containing individual VIGS constructs (each consisting of a selected DNA fragment from the target gene linked to the 129 bp-long fragment from the *P. somniferum* PHYTOENE DESATURASE gene) were used to inoculate LB medium containing 10 mM MES, 20 μM acetosyringone and 50 μg/ml kanamycin. Cultures were maintained at 28° C. for 24 hours, harvested by centrifugation at 3000×g for 20 min, and resuspended in infiltration solution (10 mM MES, 200 μM acetosyringone, 10 mM $MgCl_2$) to an $OD_{600}$ of 2.5. *A. tumefaciens* harbouring the individual VIGS constructs including the control, pTRV2:PDS, were each mixed 1:1 (v/v) with *A. tumefaciens* containing pTRV1 (GenBank accession no: AF406990), and incubated for two hours at 22° C. prior to infiltration. Two week old seedlings of HN1 grown under standard greenhouse conditions (22° C., 16 h photoperiod), with emerging first leaves, were infiltrated as described (Hagel and Facchini (2010) Nat. Chem. Biol. 6, 273-275).

Latex and capsule analysis of silenced plants: Leaf latex of infiltrated plants displaying photo-bleaching as a visual marker for successful infection and silencing was analyzed when the first flower buds emerged (~7 week old plants). Latex was collected from cut petioles, with a single drop dispersed into 500 μl of 10% acetic acid. This was diluted 10× in 1% acetic acid to give an alkaloid solution in 2% acetic acid for further analysis. Capsules were harvested from the same plants used for latex analysis and single capsules were ground to a fine powder in a ball mill (Model MM04, Retsch, Haan, Germany). Samples of ground poppy straw were then weighed accurately to 10±0.1 mg and extracted in 0.5 ml of a 10% acetic acid solution with gentle shaking for 1 h at room temperature. Samples were then clarified by centrifugation and a 50 μl subsample diluted 10× in 1% acetic acid to give an alkaloid solution in 2% acetic acid for further analysis. All solutions were analyzed as described for the poppy straw analysis from field grown F2 plants. Likewise, all data analysis was carried out using the R programming language. Putative alkaloid peaks were quantified by their pseudomolecular ion areas using custom scripts. Peak lists were compiled and any peak-wise significant differences between samples were identified using 1-way ANOVA with p-values adjusted using the Bonferroni correction for the number of unique peaks in the data set. For any peak-wise comparisons with adjusted p-values <0.05, Tukey's HSD test was used to identify peaks that were significantly different between any given sample and the control. Alkaloids were identified by comparing exact mass and retention time values to those of standards. Where standards were not available, the Bioconductor rcdk package (Smith et al (2006) Anal. Chem. 78, 779-787) was used to generate pseudomolecular formulae from exact masses within elemental constraints C=1 100, H=1 200, O=0 200, N=0 3 and mass accuracy <5 ppm. The hit with the lowest ppm error within these constraints was used to assign a putative formula.

EXAMPLE 1

Transcriptomic Analysis Reveals the Exclusive Expression of 10 Genes Encoding Five Distinct Enzyme Classes in a High Noscapine Producing Poppy Variety, HN1. These Genes are Absent from the Genome of Two Noscapine Non-Producing Varieties Capsule extract from three opium poppy varieties developed in Tasmania for alkaloid production designated as High Morphine 1 (HM1), High Thebaine 1 (HT1) and High Noscapine 1 (HN1) on the basis of the most abundant alkaloid in each case (FIG. 1A) underwent metabolite profiling. Noscapine was found to be unique to HN1 relative to HM1 and HT1. Roche 454 pyrosequencing was performed on cDNA libraries derived from stem and capsule tissue from all three varieties. Analysis of Expressed Sequence Tag (EST) abundance led to the discovery of a number of previously uncharacterized genes that are expressed in the HN1 variety but are completely absent from the HM1 and HT1 EST libraries (FIG. 1B). The corresponding genes were putatively identified as three O-methyltransferases (PSMT1, PSMT2, PSMT3), four cytochrome P450s (CYP82X1, CYP82X2, CYP82X3 and CYP719A21), an acetyltransferase (PSAT1), a carboxylesterase (PSCXE1) and a short-chain dehydrogenase/reductase (PSSDR1). In contrast a number of other functionally characterized genes associated with benzylisoquinoline alkaloid synthesis, including Berberine Bridge Enzyme (BBE), Tetrahydroprotoberberine cis-N-MethylTransferase (TNMT), Salutaridine Reductase (SalR), Salutaridinol 7-O-AcetylTransferase (SalAT) and Thebaine 6-O-demethylase (T6ODM) were expressed in all three varieties (FIG. 1B). PCR analysis on genomic DNA from all three varieties revealed that the genes exclusively expressed in the HN1 variety are present as expected in the genome of HN1 but absent from the genomes of the HM1 and HT1 varieties (FIG. 1B and FIGS. 5A-5B).

EXAMPLE 2

Analysis of an F2 Mapping Population Shows the Genes are Tightly Linked in HN1 and their Presence is Associated with the Production of Noscapine An F2 mapping population of 271 individuals was generated using HN1 and HM1 as parents. Genotyping of the field grown F2 population revealed that the HN1 specific genes are tightly linked and associated with the presence of noscapine suggesting they occur as a gene cluster involved in noscapine biosynthesis (FIG. 2B). Analysis of noscapine levels in field grown F2 capsules revealed that individuals containing this putative gene cluster fall into two classes. The first class containing 150 individuals, have relatively low levels of noscapine and the second class containing 63 individuals exhibit the high noscapine trait of the parental HN1 variety (FIG. 2B). The 58 F2 individuals that lack the putative gene cluster contain undetectable levels of noscapine (FIG. 2B). F3 family analysis confirmed that F2 individuals exhibiting the high noscapine trait were homozygous for the gene cluster while those exhibiting the low noscapine trait were heterozygous (Table 2). Noscapine levels in both the F1 population (FIG. 2A) and the heterozygous F2 class are much lower than the intermediate levels expected for a semi-dominant trait, suggesting involvement of some form of repression. The step change to high noscapine in homozygous F2 class suggests this trait is linked to the gene cluster locus rather than spread quantitatively among other loci.

EXAMPLE 3

Bacterial Artificial Chromosome Sequencing Confirms that the 10 Genes Exist as a Complex Gene Cluster To Further Characterize the Putative Noscapine Gene Cluster, a Bacterial Artificial Chromosome (BAC) Library was Prepared from Genomic DNA Isolated from HN1 and Six Overlapping BACs Containing Genes from the Cluster were Identified.

Next generation and Sanger sequencing was used to generate a high quality assembly of 401 Kb confirming the arrangement of the 10 genes in a cluster spanning 221 Kb (FIG. 3). Only one other homologous gene, a carboxylesterase (PSCXE2), was found in the genomic sequence flanking the gene cluster (FIG. 3) but PSCXE2 was not represented in any of our EST libraries. Interspersed among the ten genes are both retrotransposon and DNA transposable element (TE) sequences (FIG. 3), which may have some function in gene rearrangement for cluster formation as thought to be the case for the thalianol and marneral clusters from *A. thaliana* (Field et al (2011) PNAS 108, 16116-16121).

EXAMPLE 4

Figure 4E:
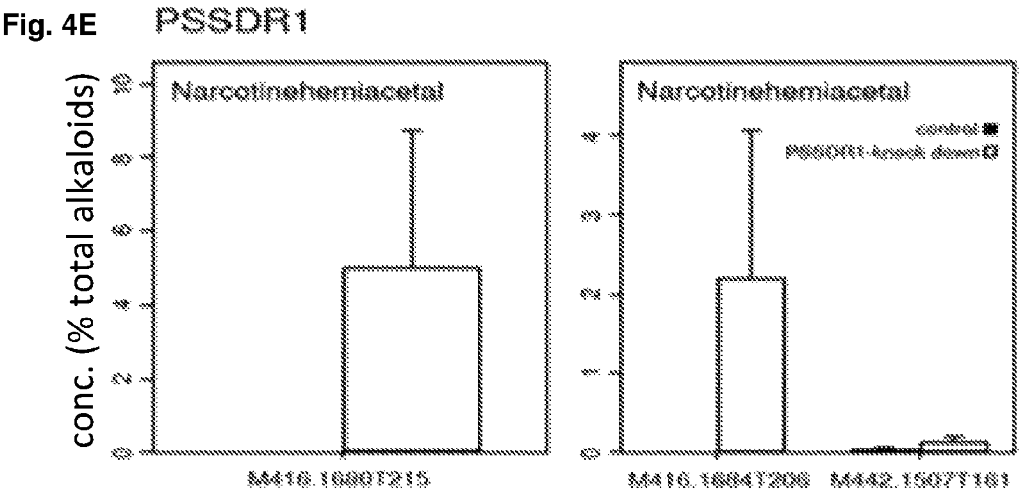
Figure 4F:
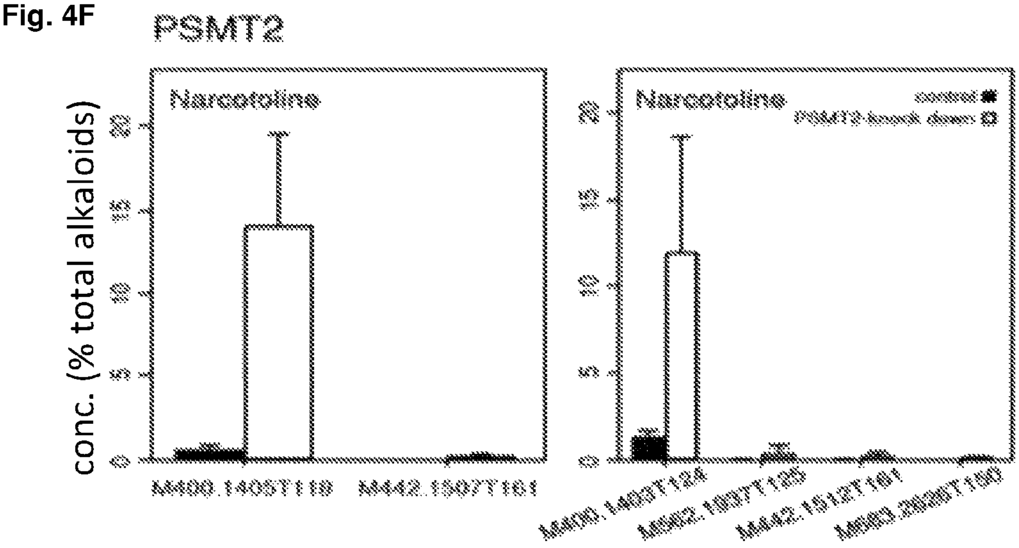
Figure 4G:
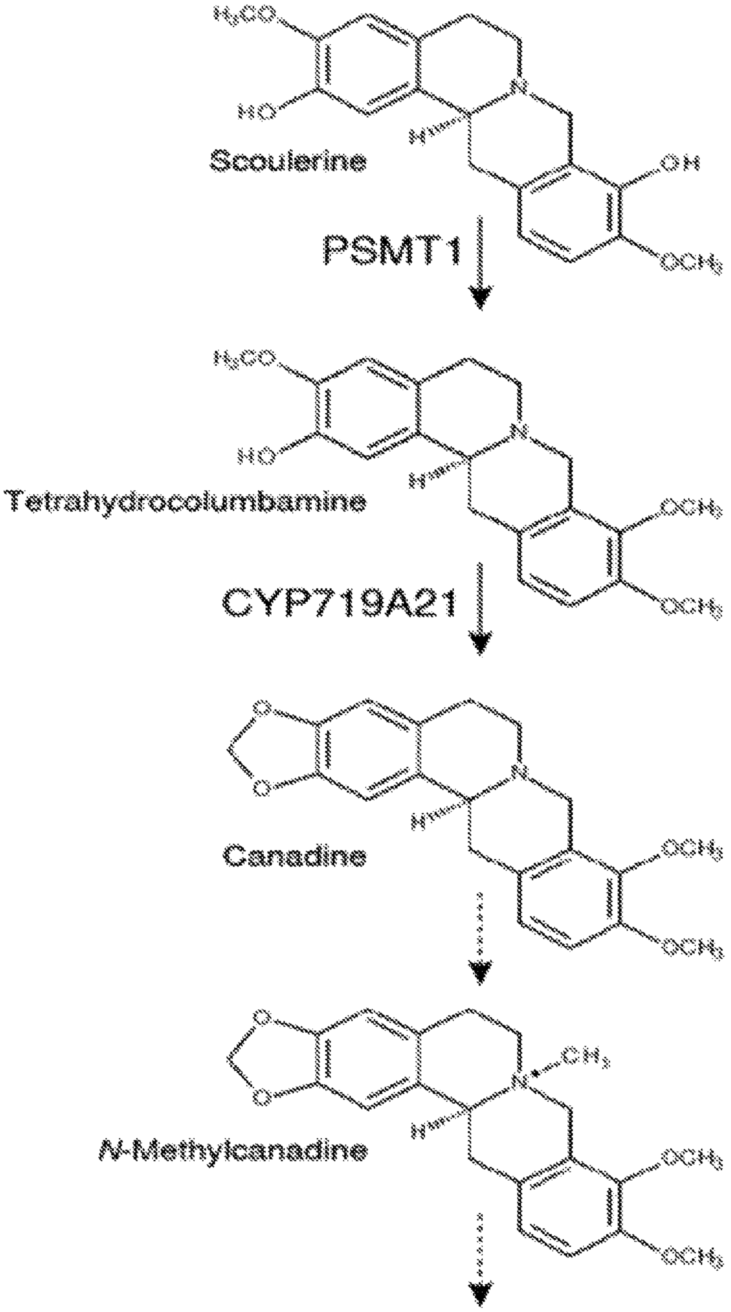
Figure 4H:
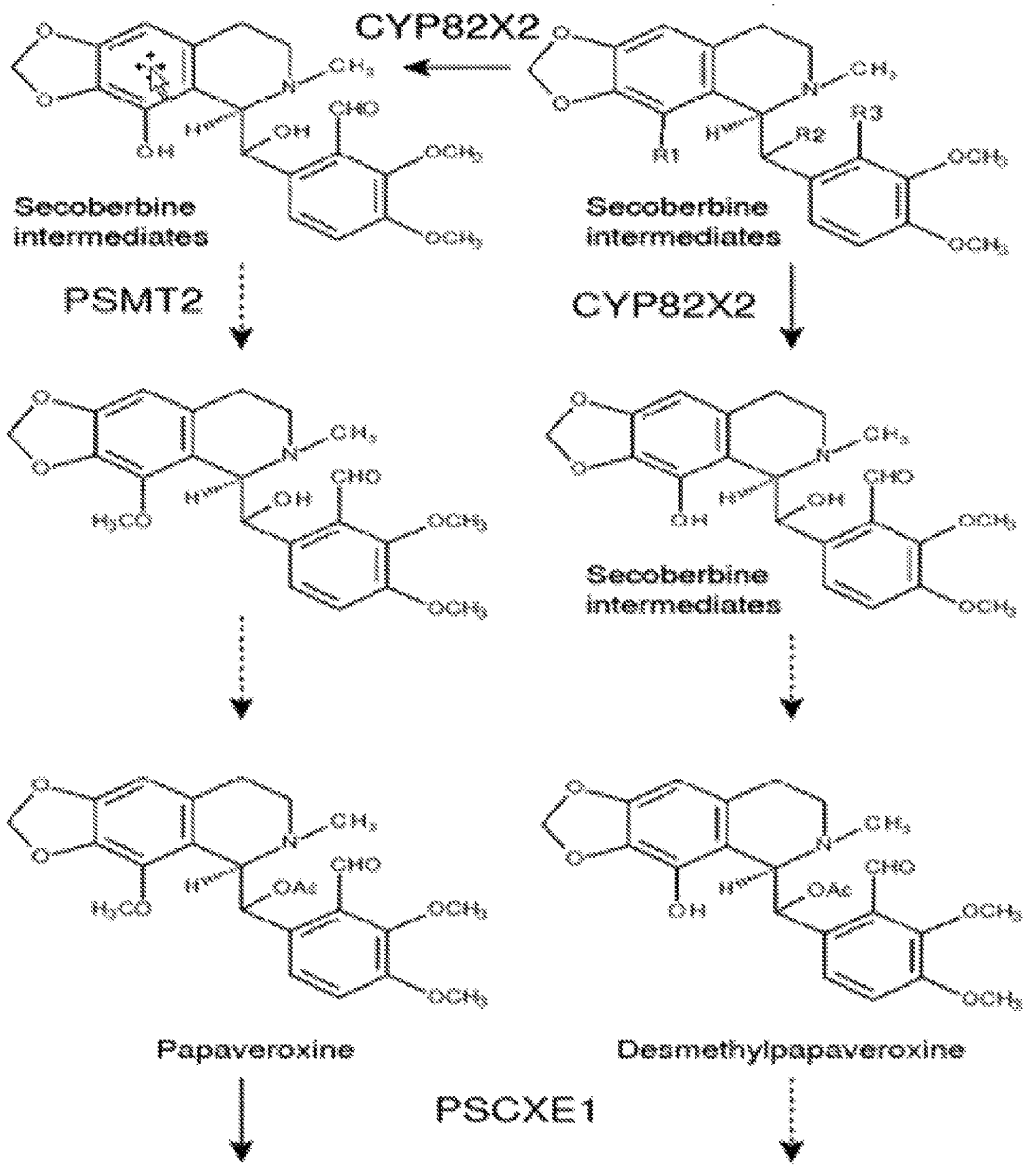
Figure 4I:
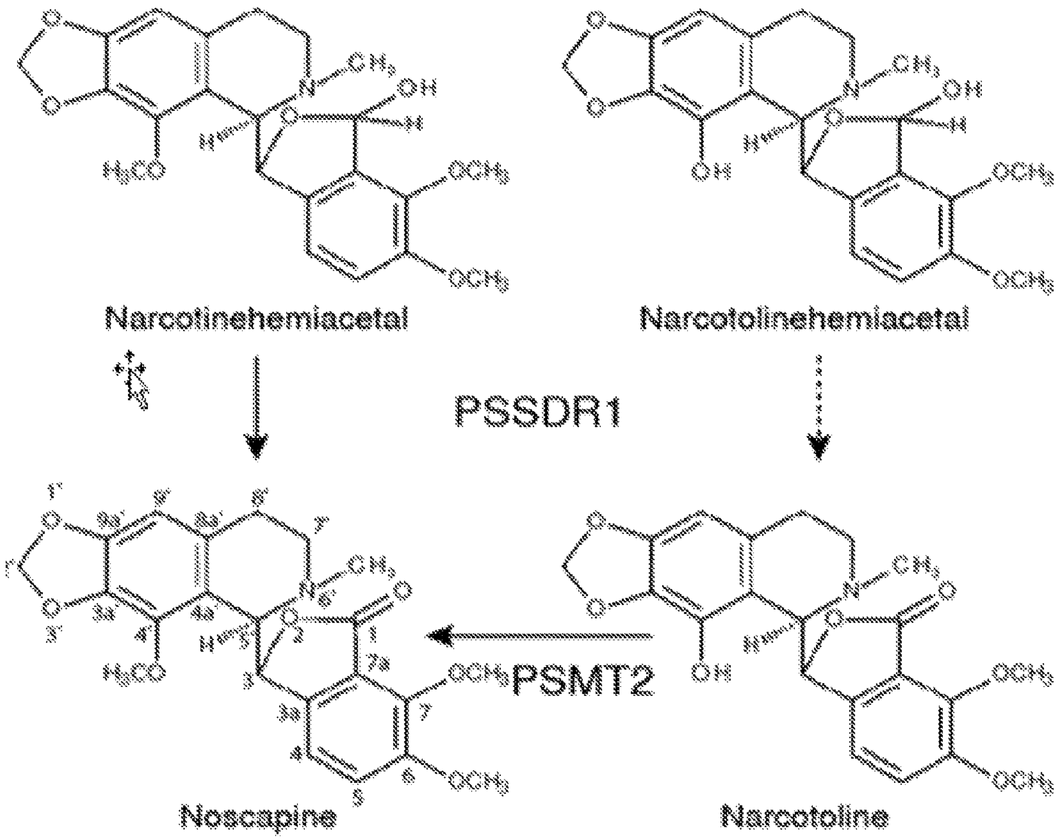
Figure 6A:
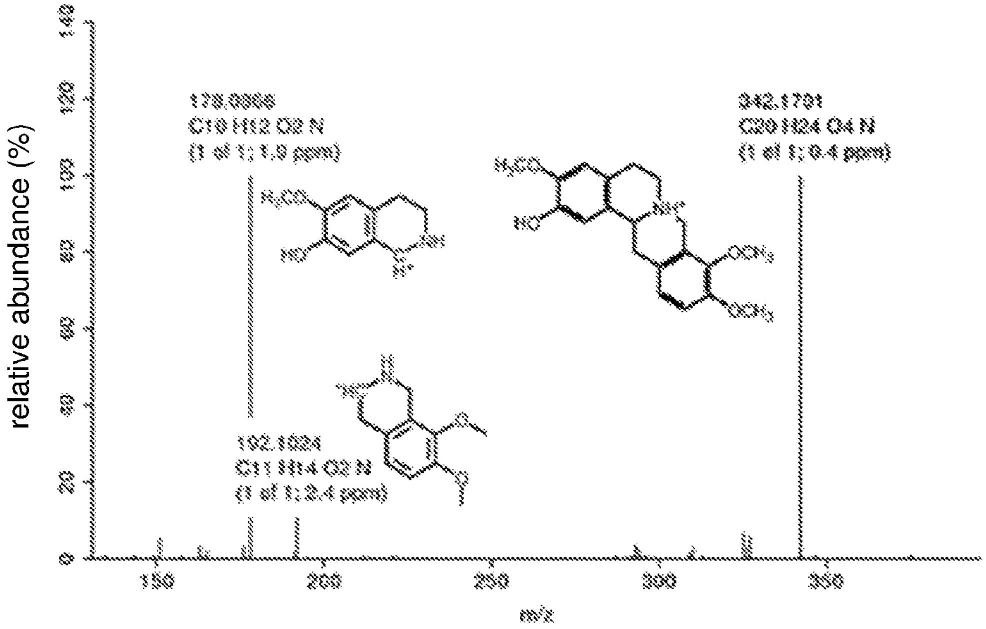
Figure 6B:
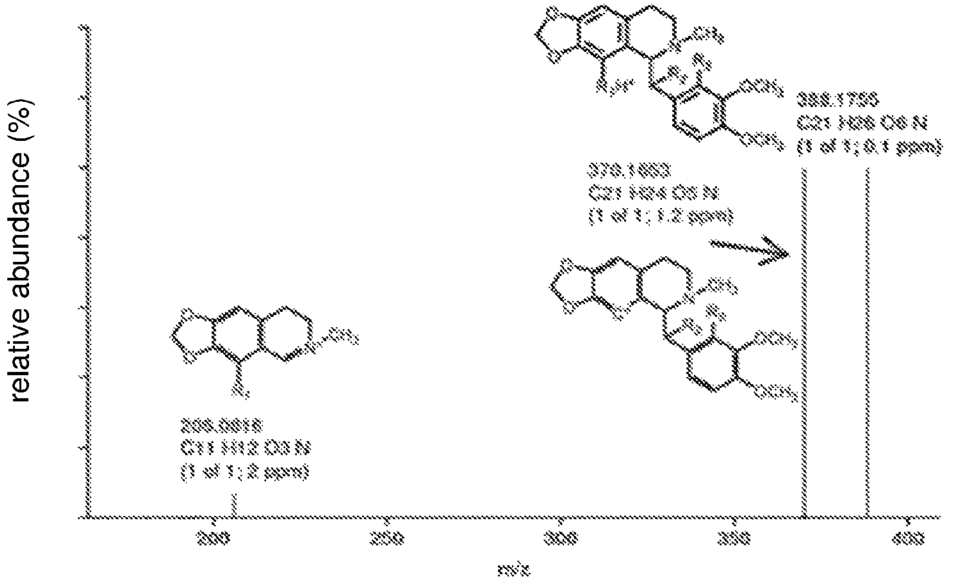
Figure 6C:
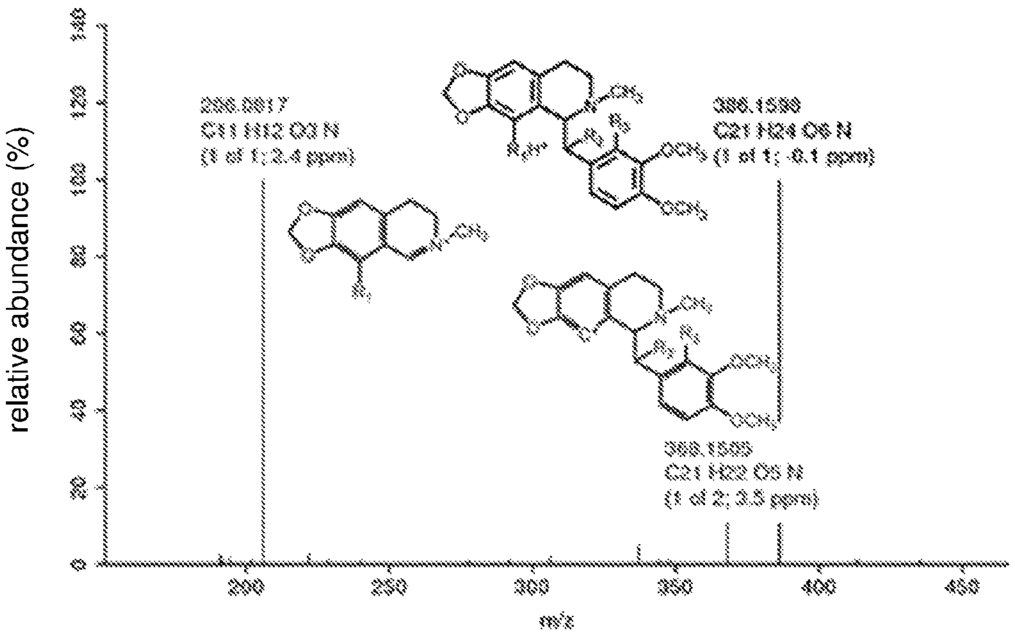
Figure 6D:
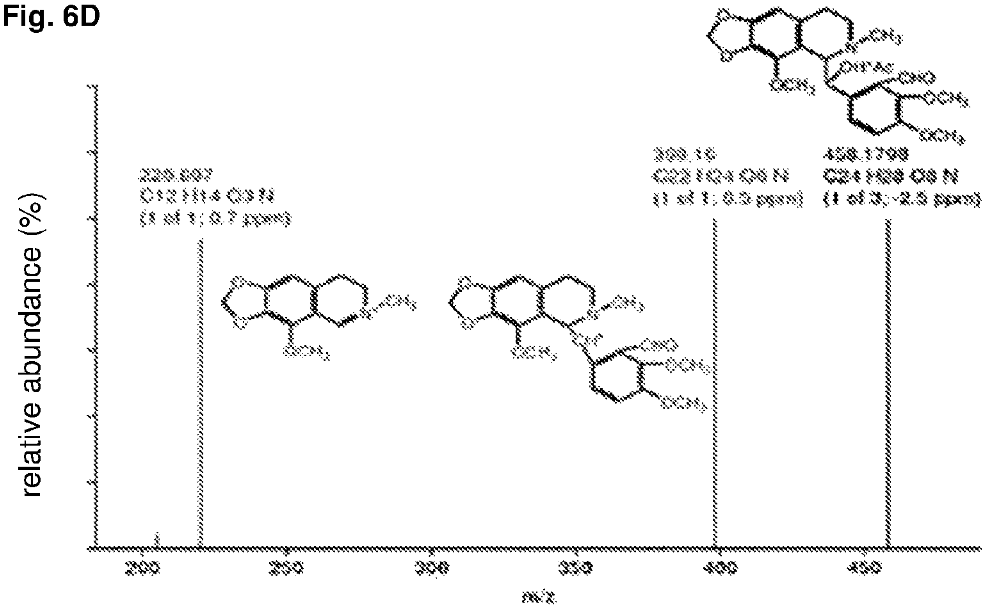
Figure 6E:
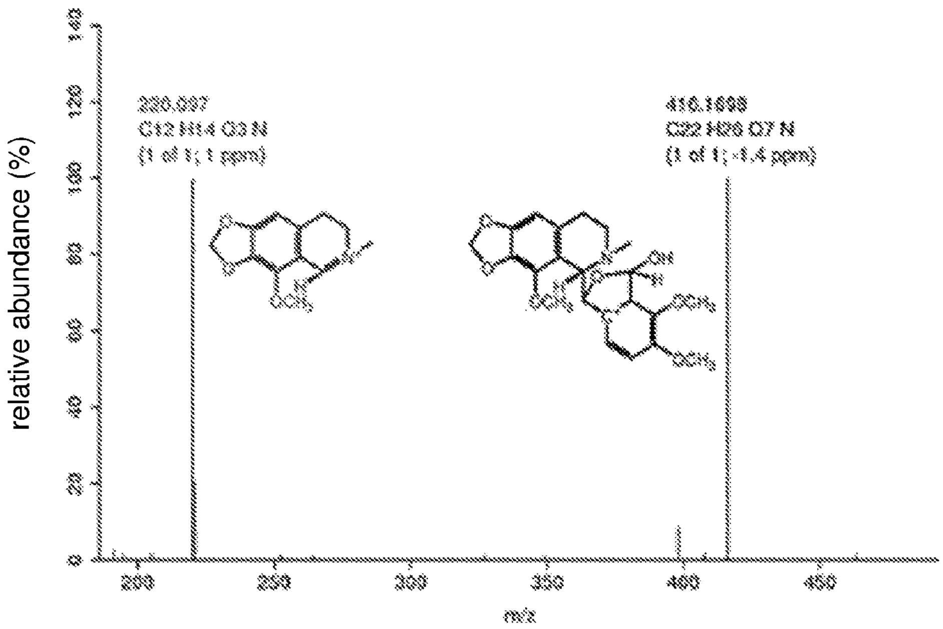
Figure 6F:
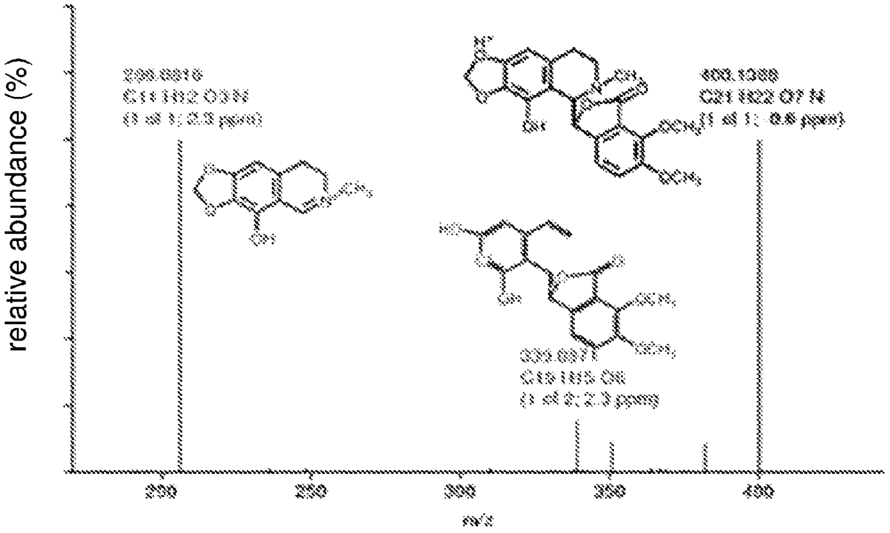

Virus Induced Gene Silencing Results in Accumulation of Pathway Intermediates Allowing Gene Function to be Linked to Noscapine Synthesis and a Novel Bifurcated Biosynthetic Pathway to be Proposed In order to functionally characterize the genes in the HN1 cluster Virus Induced Gene Silencing (VIGS) was performed on poppy seedlings. VIGS in poppy seedlings persists through to mature plant stages (Hileman et al (2005) Plant J. 44, 334-341), and therefore both leaf latex and capsule extracts were routinely assayed (FIGS. 4A-4F). Silencing PSMT1 resulted in accumulation of scoulerine in capsules and also low levels of reticuline in latex, indicating that this gene product is responsible for the first committed step in the pathway to noscapine synthesis (FIG. 4A). The predicted product of PSMT1 is tetrahydrocolumbamine (FIG. 6A), which accumulated in seedlings and capsules that were silenced for CYP719A21 (FIG. 4B). CYP719A21 shows high homology to cytochrome P450 oxidases that act as methylenedioxy bridge-forming enzymes (Diaz Chavez et al (2011) Arch. Biochem. Biophys. 507, 186193; Ikezawa et al (2009) Plant Cell Rep. 28, 123-133). Therefore CYP719A21 may encode a canadine synthase. FIG. 6). Silencing of a second cytochrome P450 gene, CYP82X2, resulted in accumulation of several secoberbine intermediates some of which may represent side products to the main synthetic pathway (FIG. 4C, FIGS. 6B-6C). Silencing of the carboxylesterase gene PSCXE1 resulted in accumulation of up to 20% total alkaloid content of putative papaveroxine (FIG. 6D) implying acetylation of a secoberbine intermediate as depicted in FIGS. 4G-4I. The PSAT1 gene from the HN1 cluster is an obvious candidate for this reaction. Silencing of PSSDR1 resulted in accumulation of what was putatively identified as narcotinehemiacetal (FIG. 6E), an immediate precursor of noscapine (FIGS. 4G-4I). These data support a biosynthetic route to noscapine that involves early O-methylation of a secoberbine intermediate at the position equivalent to the C4' hydroxyl group of noscapine (FIGS. 4G-4I). However, silencing PSMT2, resulted in accumulation of up to 20% narcotoline, indicating that O-methylation at the C4' hydroxyl group can also occur as a final step in noscapine production (FIG. 4F). These results imply bifurcation of the main pathway at the secoberbine intermediate stage with PSMT2 being responsible for both the O-methylation of a secoberbine intermediate and narcotoline. Silencing PSMT2 results in accumulation of high levels of narcotoline as flux is directed down the desmethyl branch of the pathway (FIG. 4F and FIG. 6F).

The invention claimed is:

1. A method to produce a *P. somniferum* plant that has altered expression of a polypeptide, comprising:
   i) mutagenizing a wild-type seed from a wild-type *P. somniferum* plant that expresses said polypeptide, thereby generating mutagenized seed;
   ii) cultivating the mutagenized seed to produce first and subsequent generations of mutagenized plants;
   iii) obtaining seed from the first and subsequent generations of mutagenized plants;
   iv) determining if the plants from the seed from said first and subsequent generations of mutagenized plants have an altered nucleotide sequence, altered expression of said polypeptide or both, an altered nucleotide sequence and altered expression of said polypeptide by obtaining a nucleic acid sample from the plant of said first or subsequent generation of mutagenized plants and analysing the nucleic acid sample for presence of a nucleic acid molecule comprising a nucleotide sequence having at least 90% sequence identity to the sequence of SEQ ID NO: 7, 8, 9 or 10 and that encodes a polypeptide with opiate alkaloid biosynthetic activity; and optionally
   v) comparing the nucleotide sequence of the nucleic acid molecule in said sample to a nucleotide sequence of a nucleic acid molecule of the wild-type plant.

2. The method according to claim 1 wherein said nucleic acid sample obtained from the mutagenized seed or plant is analysed by a method comprising:
   i) extracting nucleic acid molecules from said first and subsequent generations of mutagenized plants;
   ii) amplifying a part of said extracted nucleic acid molecules by a polymerase chain reaction, thereby generating amplified nucleic acid comprising a part of a nucleic acid molecule comprising a nucleotide sequence having at least 90% sequence identity to the sequence of SEQ ID NO: 7, 8, 9 or 10;
   iii) forming a preparation comprising the amplified nucleic acid and nucleic acid extracted from wild-type plants to form heteroduplex nucleic acid;
   iv) incubating said preparation with a single stranded nuclease that cuts at a region of heteroduplex nucleic acid to identify a mismatch in said heteroduplex; and
   v) determining the site of the mismatch in said nucleic acid heteroduplex.

3. The method according to claim 1, wherein said *P. somniferum* plant has enhanced opiate alkaloid biosynthetic activity.

4. The method according to claim 1, wherein said *P. somniferum* plant has reduced or abrogated opiate alkaloid biosynthetic activity.

5. A *P. somniferum* plant obtained by the method of claim 1.

6. The method of claim 1, wherein the nucleic acid sample is analysed for the presence of a nucleic acid molecule comprising the nucleotide sequence of SEQ ID NO: 7, 8, 9 or 10.

* * * * *